(12) United States Patent
Hosoguchi et al.

(10) Patent No.: US 12,421,322 B2
(45) Date of Patent: Sep. 23, 2025

(54) ANTIBODY VARIANT AND ISOFORM WITH LOWERED BIOLOGICAL ACTIVITY

(71) Applicant: Chugai Seiyaku Kabushiki Kaisha, Tokyo (JP)

(72) Inventors: Kensaku Hosoguchi, Tokyo (JP); Maki Kuwayama, Tokyo (JP); Chifumi Seida, Tokyo (JP); Yosuke Watanabe, Tokyo (JP); Nobuyuki Tanaka, Tokyo (JP); Satoshi Saitoh, Tokyo (JP); Masakazu Fukuda, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 200 days.

(21) Appl. No.: 16/758,128

(22) PCT Filed: Oct. 31, 2018

(86) PCT No.: PCT/JP2018/040436
§ 371 (c)(1),
(2) Date: Apr. 22, 2020

(87) PCT Pub. No.: WO2019/088143
PCT Pub. Date: May 9, 2019

(65) Prior Publication Data
US 2020/0283544 A1   Sep. 10, 2020

(30) Foreign Application Priority Data

Nov. 1, 2017   (JP) ................. 2017-212179

(51) Int. Cl.
*C07K 16/46* (2006.01)
*G01N 33/68* (2006.01)
*A61K 39/00* (2006.01)

(52) U.S. Cl.
CPC ....... *C07K 16/468* (2013.01); *G01N 33/6854* (2013.01); *A61K 2039/505* (2013.01); *C07K 2317/31* (2013.01); *C07K 2317/51* (2013.01); *C07K 2317/565* (2013.01); *C07K 2317/71* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,208,479 A | 6/1980 | Zuk et al. |
| 4,444,878 A | 4/1984 | Paulus |
| 4,474,893 A | 10/1984 | Reading |
| 5,322,678 A | 6/1994 | Morgan et al. |
| 5,496,549 A | 3/1996 | Yamazaki et al. |
| 5,591,828 A | 1/1997 | Bosslet et al. |
| 5,639,641 A | 6/1997 | Pedersen et al. |
| 5,693,762 A | 12/1997 | Queen et al. |
| 5,744,446 A | 4/1998 | Lollar et al. |
| 5,795,965 A | 8/1998 | Tsuchiya et al. |
| 5,859,205 A | 1/1999 | Adair et al. |
| 5,945,311 A | 8/1999 | Lindhofer et al. |
| 5,990,286 A | 11/1999 | Khawli et al. |
| 6,005,091 A | 12/1999 | Blackburn et al. |
| 6,010,902 A | 1/2000 | Ledbetter et al. |
| 6,126,980 A | 10/2000 | Smith et al. |
| 6,129,914 A | 10/2000 | Weiner |
| 6,329,511 B1 | 12/2001 | Vasquez et al. |
| 6,485,943 B2 | 11/2002 | Stevens et al. |
| 6,677,436 B1 | 1/2004 | Sato et al. |
| 6,737,056 B1 | 5/2004 | Presta |
| 6,884,879 B1 | 4/2005 | Baca et al. |
| 6,913,747 B1 | 7/2005 | Co et al. |
| 7,033,590 B1 | 4/2006 | Scheiflinger et al. |
| 7,052,873 B2 | 5/2006 | Tsuchiya |
| 7,615,213 B2 | 11/2009 | Kasaian et al. |
| 8,062,635 B2 | 11/2011 | Hattori et al. |
| 8,592,562 B2 | 11/2013 | Kannan et al. |
| 8,597,911 B2 | 12/2013 | Miyazaki et al. |
| 8,765,124 B2 | 7/2014 | Saito et al. |
| 9,096,651 B2 | 8/2015 | Igawa et al. |
| 9,334,331 B2 | 5/2016 | Igawa et al. |
| 9,527,926 B2 | 12/2016 | Ho et al. |
| 9,556,279 B2 | 1/2017 | Niwa et al. |
| 9,637,557 B2 | 5/2017 | Scheer et al. |
| 9,670,269 B2 | 6/2017 | Igawa et al. |
| 9,828,429 B2 | 11/2017 | Igawa et al. |

(Continued)

FOREIGN PATENT DOCUMENTS

| | | |
|---|---|---|
| AU | 2009290162 | 4/2010 |
| CA | 2 019 559 | 12/1990 |

(Continued)

OTHER PUBLICATIONS

Janeway, Charles A. "Immunobiology: The Immune System in Health and Disease." 2001 (Year: 2001).*
Sela-Culang et al. Frontiers in Immunology 4 (2013):302 (Year: 2013).*
Colman, Research in Immunology 145.1 (1994): 33-36 (Year: 1994).*

(Continued)

*Primary Examiner* — Zachariah Lucas
*Assistant Examiner* — Lia E Taylor
(74) *Attorney, Agent, or Firm* — Fish & Richardson P.C.

(57) ABSTRACT

As antibody variants and isoforms having reduced FVIII mimetic activity than Emicizumab, the antibody variants having some specific amino acid residues in the variable region cleaved out and missing (Q-CDR-Clipped Variants) and the antibody isoforms having inter-heavy chain disulfide bonds less susceptible to reduction under mild reducing conditions (Protected Disulfide Isoforms) are provided.

7 Claims, 12 Drawing Sheets
Specification includes a Sequence Listing.

(56) References Cited

U.S. PATENT DOCUMENTS

| | | |
|---|---|---|
| 10,011,858 B2 | 7/2018 | Igawa et al. |
| 10,022,319 B2 | 7/2018 | Igawa et al. |
| 10,450,381 B2 | 10/2019 | Igawa et al. |
| 10,759,870 B2 | 9/2020 | Teranishi et al. |
| 10,934,344 B2 | 3/2021 | Igawa et al. |
| 11,046,784 B2 | 6/2021 | Igawa et al. |
| 11,124,576 B2 | 9/2021 | Igawa et al. |
| 11,142,587 B2 | 10/2021 | Igawa et al. |
| 11,150,254 B2 | 10/2021 | Nogami et al. |
| 11,168,344 B2 | 11/2021 | Igawa et al. |
| 11,214,623 B2 | 1/2022 | Igawa et al. |
| 11,248,053 B2 | 2/2022 | Igawa et al. |
| 11,352,438 B2 | 6/2022 | Yoneyama et al. |
| 11,612,562 B2 | 3/2023 | Igawa et al. |
| 11,649,262 B2 | 5/2023 | Tanaka et al. |
| 2002/0009430 A1 | 1/2002 | Lindhofer et al. |
| 2002/0062010 A1 | 5/2002 | Arathoon et al. |
| 2002/0142374 A1 | 10/2002 | Gallo et al. |
| 2002/0164339 A1 | 11/2002 | Do et al. |
| 2002/0164668 A1 | 11/2002 | Durham et al. |
| 2003/0187225 A1 | 10/2003 | Penichet et al. |
| 2003/0190311 A1 | 10/2003 | Dall'Acqua et al. |
| 2003/0207346 A1 | 11/2003 | Arathoon et al. |
| 2003/0211460 A1 | 11/2003 | Nelsestuen |
| 2003/0219441 A1 | 11/2003 | Thorpe et al. |
| 2003/0224397 A1 | 12/2003 | Lowman et al. |
| 2004/0081651 A1 | 4/2004 | Karpusas et al. |
| 2004/0236080 A1 | 11/2004 | Aburatani et al. |
| 2005/0095243 A1 | 5/2005 | Chan et al. |
| 2005/0130224 A1 | 6/2005 | Saito et al. |
| 2005/0164307 A1 | 7/2005 | Kojima et al. |
| 2005/0191293 A1 | 9/2005 | Deshpande et al. |
| 2005/0244403 A1 | 11/2005 | Lazar et al. |
| 2005/0244416 A1 | 11/2005 | Jung |
| 2005/0261229 A1 | 11/2005 | Gillies |
| 2005/0266425 A1 | 12/2005 | Zauderer et al. |
| 2006/0019342 A1 | 1/2006 | Dall'Acqua et al. |
| 2006/0057149 A1 | 3/2006 | Johnson et al. |
| 2006/0063228 A1 | 3/2006 | Kasaian et al. |
| 2006/0074225 A1 | 4/2006 | Chamberlain |
| 2006/0134709 A1 | 6/2006 | Stavenhagen et al. |
| 2006/0134805 A1 | 6/2006 | Berg et al. |
| 2006/0159673 A1 | 7/2006 | Kojima |
| 2006/0160184 A1 | 7/2006 | Hoogenboom et al. |
| 2006/0204493 A1 | 9/2006 | Huang et al. |
| 2006/0269989 A1 | 11/2006 | Miyazaki et al. |
| 2007/0036785 A1 | 2/2007 | Kishimoto et al. |
| 2007/0041978 A1 | 2/2007 | Hattori et al. |
| 2007/0054354 A1 | 3/2007 | Humphreys et al. |
| 2007/0059312 A1 | 3/2007 | Baca et al. |
| 2007/0087381 A1 | 4/2007 | Kojima |
| 2007/0110757 A1 | 5/2007 | Wei et al. |
| 2008/0075712 A1 | 3/2008 | Hattori et al. |
| 2008/0166756 A1 | 7/2008 | Tsuchiya et al. |
| 2009/0117097 A1 | 5/2009 | Igawa et al. |
| 2009/0263392 A1 | 10/2009 | Igawa et al. |
| 2009/0324589 A1 | 12/2009 | Igawa et al. |
| 2010/0003254 A1 | 1/2010 | Hattori et al. |
| 2010/0015133 A1 | 1/2010 | Igawa et al. |
| 2010/0028372 A1 | 2/2010 | Jezek |
| 2010/0055092 A1 | 3/2010 | Hasegawa et al. |
| 2010/0239577 A1 | 9/2010 | Igawa et al. |
| 2010/0286374 A1 | 11/2010 | Kannan et al. |
| 2010/0291072 A1 | 11/2010 | Lowman et al. |
| 2010/0298542 A1 | 11/2010 | Igawa et al. |
| 2010/0331527 A1 | 12/2010 | Davis et al. |
| 2011/0059091 A1 | 3/2011 | Chang et al. |
| 2011/0076275 A1 | 3/2011 | Igawa et al. |
| 2011/0097754 A1 | 4/2011 | Hilbert et al. |
| 2011/0111406 A1 | 5/2011 | Igawa et al. |
| 2011/0236374 A1 | 9/2011 | Shitara et al. |
| 2011/0245473 A1 | 10/2011 | Igawa et al. |
| 2011/0287009 A1 | 11/2011 | Scheer et al. |
| 2012/0009188 A1 | 1/2012 | Behrens et al. |
| 2012/0010387 A1 | 1/2012 | Niwa et al. |
| 2012/0149876 A1 | 6/2012 | Von Kreudenstein |
| 2012/0237517 A1 | 9/2012 | Hattori et al. |
| 2013/0011866 A1 | 1/2013 | Igawa et al. |
| 2013/0018174 A1 | 1/2013 | Igawa et al. |
| 2013/0039913 A1 | 2/2013 | Labrujn et al. |
| 2013/0085199 A1 | 4/2013 | Tamori et al. |
| 2013/0115208 A1 | 5/2013 | Ho et al. |
| 2013/0195849 A1 | 8/2013 | Spreter et al. |
| 2013/0330345 A1 | 12/2013 | Igawa et al. |
| 2014/0037632 A1 | 2/2014 | Igawa et al. |
| 2014/0051833 A1 | 2/2014 | Fischer et al. |
| 2014/0154270 A1 | 6/2014 | Wang et al. |
| 2014/0303356 A1 | 10/2014 | Gramer et al. |
| 2014/0370018 A1 | 12/2014 | Igawa et al. |
| 2014/0370020 A1 | 12/2014 | Kuramochi et al. |
| 2014/0377253 A1 | 12/2014 | Harding et al. |
| 2015/0240287 A1 | 8/2015 | Soeda et al. |
| 2015/0284465 A1 | 10/2015 | Igawa et al. |
| 2015/0297820 A1 | 10/2015 | Kawai |
| 2015/0315278 A1 | 11/2015 | Igawa et al. |
| 2015/0315296 A1 | 11/2015 | Schaefer et al. |
| 2016/0024147 A1 | 1/2016 | Tustian et al. |
| 2016/0222129 A1 | 8/2016 | Igawa et al. |
| 2016/0229915 A1 | 8/2016 | Igawa et al. |
| 2017/0022293 A1 | 1/2017 | Igawa et al. |
| 2017/0145111 A1 | 5/2017 | Hattori et al. |
| 2017/0253663 A1 | 9/2017 | Yoneyama |
| 2017/0275332 A1 | 9/2017 | Igawa et al. |
| 2017/0275376 A1 | 9/2017 | Igawa et al. |
| 2017/0283483 A1 | 10/2017 | Igawa et al. |
| 2018/0002443 A1 | 1/2018 | Hattori et al. |
| 2018/0011114 A1 | 1/2018 | Nogami et al. |
| 2018/0051307 A1 | 2/2018 | Igawa et al. |
| 2018/0057607 A1 | 3/2018 | Igawa et al. |
| 2018/0142027 A1 | 5/2018 | Igawa et al. |
| 2018/0162902 A1 | 6/2018 | Igawa et al. |
| 2018/0244800 A1 | 8/2018 | Hattori et al. |
| 2019/0062368 A1 | 2/2019 | Igawa et al. |
| 2019/0112390 A1 | 4/2019 | Hattori et al. |
| 2019/0185578 A1 | 6/2019 | Igawa et al. |
| 2019/0194352 A1 | 6/2019 | Yoneyama et al. |
| 2019/0309090 A1 | 10/2019 | Yoneyama et al. |
| 2019/0315884 A1 | 10/2019 | Igawa et al. |
| 2019/0330268 A1 | 10/2019 | Tanaka et al. |
| 2019/0352334 A1 | 11/2019 | Igawa et al. |
| 2019/0359728 A1 | 11/2019 | Hattori et al. |
| 2020/0157243 A1 | 5/2020 | Yoneyama |
| 2020/0207805 A1 | 7/2020 | Igawa et al. |
| 2020/0223940 A1 | 7/2020 | Teranishi et al. |
| 2020/0270363 A1 | 8/2020 | Igawa et al. |
| 2020/0277402 A1 | 9/2020 | Hattori et al. |
| 2020/0354473 A1 | 11/2020 | Teranishi et al. |
| 2020/0407463 A1 | 12/2020 | Yoneyama |
| 2021/0040147 A1 | 2/2021 | Igawa et al. |
| 2021/0107994 A1 | 4/2021 | Shima et al. |
| 2021/0107995 A1 | 4/2021 | Hattori et al. |
| 2021/0189006 A1 | 6/2021 | Saeki et al. |
| 2021/0238307 A1 | 8/2021 | Yoneyama |
| 2021/0292360 A1 | 9/2021 | Igawa et al. |
| 2021/0324109 A1 | 10/2021 | Igawa et al. |
| 2021/0380717 A1 | 12/2021 | Hattori et al. |
| 2022/0010030 A1 | 1/2022 | Igawa et al. |
| 2022/0073644 A1 | 3/2022 | Kameoka et al. |
| 2022/0073645 A1 | 3/2022 | Yoneyama |
| 2022/0119551 A1 | 4/2022 | Igawa et al. |
| 2022/0135618 A1 | 5/2022 | Igawa et al. |
| 2022/0213217 A1 | 7/2022 | Hattori et al. |
| 2022/0267470 A1 | 8/2022 | Igawa et al. |
| 2022/0267822 A1 | 8/2022 | Igawa et al. |
| 2022/0305122 A1 | 9/2022 | Yoneyama et al. |
| 2022/0315667 A1 | 10/2022 | Yoneyama et al. |
| 2022/0324999 A1 | 10/2022 | Yoneyama |
| 2022/0389054 A1 | 12/2022 | Igawa et al. |
| 2022/0389105 A1 | 12/2022 | Igawa et al. |
| 2023/0159658 A1 | 5/2023 | Yoneyama et al. |
| 2023/0174673 A1 | 6/2023 | Yoneyama |
| 2023/0212315 A1 | 7/2023 | Igawa et al. |
| 2023/0227498 A1 | 7/2023 | Igawa et al. |
| 2023/0348621 A1 | 11/2023 | Hattori et al. |

(56) References Cited

U.S. PATENT DOCUMENTS

| | | |
|---|---|---|
| 2024/0052058 A1 | 2/2024 | Yoneyama et al. |
| 2024/0052059 A1 | 2/2024 | Shima et al. |
| 2024/0052060 A1 | 2/2024 | Yoneyama |
| 2024/0059795 A1 | 2/2024 | Igawa et al. |
| 2024/0083939 A1 | 3/2024 | Igawa et al. |
| 2024/0190976 A1 | 6/2024 | Igawa et al. |
| 2024/0190997 A1 | 6/2024 | Hattori et al. |
| 2024/0239906 A1 | 7/2024 | Igawa et al. |
| 2024/0317891 A1 | 9/2024 | Yoneyama |

FOREIGN PATENT DOCUMENTS

| | | | |
|---|---|---|---|
| CA | 2 331 641 | 11/1999 | |
| CA | 2 541 671 | 4/2005 | |
| CA | 2 603 264 | 10/2006 | |
| CA | 2 603 408 | 10/2006 | |
| CA | 2 647 846 | 10/2007 | |
| CA | 2 700 986 | 4/2009 | |
| CA | 2 817 964 | 5/2012 | |
| CA | 2 812 739 | 10/2012 | |
| CA | 2 859 667 | 6/2013 | |
| CA | 2 888 496 | 5/2014 | |
| CA | 3 031 082 | 1/2018 | |
| CA | 3 027 018 | 2/2018 | |
| CN | 1229646 | 11/2005 | |
| CN | 101198698 | 6/2008 | |
| CN | 101460622 | 6/2009 | |
| CN | 101883588 | 11/2010 | |
| CN | 101883793 | 11/2010 | |
| CN | 101906160 | 12/2010 | |
| CN | 102084254 | 6/2011 | |
| CN | 102471378 | 5/2012 | |
| CN | 102782131 | 11/2012 | |
| CN | 102858366 | 1/2013 | |
| CN | 102946906 | 2/2013 | |
| CN | 103298937 | 9/2013 | |
| CN | 104321341 | 1/2015 | |
| CN | 105177091 | 12/2015 | |
| CN | 107108746 | 8/2017 | |
| CN | 101874042 | 9/2018 | |
| CN | 105848668 | 8/2021 | |
| CN | 105859889 | 8/2021 | |
| EP | 0 329 185 | 8/1989 | |
| EP | 0 369 566 | 5/1990 | |
| EP | 0 404 097 | 12/1990 | |
| EP | 04/32134 | 6/1991 | |
| EP | 0 637 593 | 2/1995 | |
| EP | 0 783 893 | 7/1997 | |
| EP | 0 811 691 | 12/1997 | |
| EP | 1 069 185 | 1/2001 | |
| EP | 1 220 923 | 7/2002 | |
| EP | 1 327 681 | 7/2003 | |
| EP | 1 505 148 | 2/2005 | |
| EP | 1 510 943 | 3/2005 | |
| EP | 0 979 281 B | 7/2005 | |
| EP | 1 605 058 | 12/2005 | |
| EP | 1 688 488 | 8/2006 | |
| EP | 1 693 448 | 8/2006 | |
| EP | 1 712 240 A | 10/2006 | |
| EP | 1 773 391 | 4/2007 | |
| EP | 1 870 458 | 12/2007 | |
| EP | 1 870 459 | 12/2007 | |
| EP | 1 876 236 | 1/2008 | |
| EP | 1 900 814 | 3/2008 | |
| EP | 2 006 381 | 12/2008 | |
| EP | 2 009 101 | 12/2008 | |
| EP | 2 107 115 | 10/2009 | |
| EP | 2 202 245 | 6/2010 | |
| EP | 2 238 985 A | 10/2010 | |
| EP | 1 688 488 B9 | 3/2012 | |
| EP | 2 522 724 | 11/2012 | |
| EP | 2 526 963 | 11/2012 | |
| EP | 2 543 727 | 1/2013 | |
| EP | 2 644 698 | 10/2013 | |
| EP | 2 905 290 | 8/2015 | |
| EP | 2 914 634 | 9/2015 | |
| EP | 2 275 443 B | 12/2015 | |
| EP | 3 159 006 | 4/2017 | |
| EP | 3345616 A1 * | 7/2018 | ............. A61P 35/00 |
| EP | 3 395 835 B | 2/2021 | |
| JP | S63-52890 | 3/1988 | |
| JP | H02-028200 | 1/1990 | |
| JP | H02-145187 | 6/1990 | |
| JP | H03-500644 | 2/1991 | |
| JP | H05-501543 | 3/1993 | |
| JP | H05-184383 | 7/1993 | |
| JP | H05-199894 | 8/1993 | |
| JP | H05-203652 | 8/1993 | |
| JP | H05-213775 | 8/1993 | |
| JP | H05-304992 | 11/1993 | |
| JP | H07-67688 | 3/1995 | |
| JP | H08-500979 | 2/1996 | |
| JP | H08-510555 | 11/1996 | |
| JP | H09-506001 | 6/1997 | |
| JP | H10-165184 | 6/1998 | |
| JP | H10-511085 | 10/1998 | |
| JP | H11-500915 | 1/1999 | |
| JP | H11-500916 | 1/1999 | |
| JP | H11-71288 | 3/1999 | |
| JP | H11-504007 | 4/1999 | |
| JP | H11-506310 | 6/1999 | |
| JP | 2001-523971 | 11/2001 | |
| JP | 2002-518041 | 6/2002 | |
| JP | 2003-055398 | 2/2003 | |
| JP | 2003-509049 | 3/2003 | |
| JP | 2004-086682 | 3/2004 | |
| JP | 2004-086862 | 3/2004 | |
| JP | 2004-511426 | 4/2004 | |
| JP | 2004-321100 | 11/2004 | |
| JP | 2005-501514 | 1/2005 | |
| JP | 2005-101105 | 3/2005 | |
| JP | 2005-535341 | 11/2005 | |
| JP | 2005-378266 | 12/2005 | |
| JP | 2005-537009 | 12/2005 | |
| JP | 2008-510466 | 4/2008 | |
| JP | 2008-523140 | 7/2008 | |
| JP | 2010-503397 | 2/2010 | |
| JP | 2010-522701 | 7/2010 | |
| JP | 2011-502126 | 1/2011 | |
| JP | 2011-508604 | 3/2011 | |
| JP | 2011-137000 | 7/2011 | |
| JP | 2012-082201 | 4/2012 | |
| JP | 2012-515160 | 7/2012 | |
| JP | 2012-522527 | 9/2012 | |
| JP | 2012-531439 | 12/2012 | |
| JP | 5144499 | 2/2013 | |
| JP | 2013-529084 | 7/2013 | |
| JP | 2013-529190 | 7/2013 | |
| JP | 2013-165716 | 8/2013 | |
| JP | 5334319 | 11/2013 | |
| JP | 2014-511836 | 5/2014 | |
| JP | 2014-524748 | 9/2014 | |
| JP | 2015-502409 | 1/2015 | |
| JP | 2015-504434 | 2/2015 | |
| JP | 2015-510764 | 4/2015 | |
| JP | 2015-514684 | 5/2015 | |
| JP | 2015-130883 | 7/2015 | |
| JP | 2015-536349 | 12/2015 | |
| JP | 2016-508117 | 3/2016 | |
| JP | 2016-69329 | 5/2016 | |
| JP | 2017-511139 | 4/2017 | |
| JP | 6534615 | 6/2019 | |
| KR | 2012/0123055 | 11/2012 | |
| KR | 2013/0102113 | 9/2013 | |
| KR | 2013/0102640 | 9/2013 | |
| NO | 20062087 | 7/2006 | |
| RU | 94028282 | 7/1996 | |
| RU | 2266298 | 12/2005 | |
| RU | 2339696 | 11/2008 | |
| RU | 2478702 C2 | 4/2013 | |
| RU | 2534347 | 11/2014 | |
| RU | 2586515 | 6/2016 | |
| TW | 2007/14313 | 4/2007 | |
| TW | 2007/22517 | 6/2007 | |

(56) References Cited

FOREIGN PATENT DOCUMENTS

| | | |
|---|---|---|
| TW | 2016/00112 | 2/2012 |
| TW | 2012/43049 | 11/2012 |
| TW | I452135 | 9/2014 |
| TW | I452136 | 9/2014 |
| TW | 2016/25299 | 7/2016 |
| TW | 2018/22815 | 7/2018 |
| WO | WO 89/01343 | 2/1989 |
| WO | WO 91/08770 | 6/1991 |
| WO | WO 92/19759 | 11/1992 |
| WO | WO 93/11161 | 6/1993 |
| WO | WO 94/05690 | 3/1994 |
| WO | WO 94/13804 | 6/1994 |
| WO | WO 95/01571 | 1/1995 |
| WO | WO 95/33844 | 12/1995 |
| WO | WO 96/01653 | 1/1996 |
| WO | WO 96/07754 | 3/1996 |
| WO | WO 96/11020 | 4/1996 |
| WO | WO 96/12503 | 5/1996 |
| WO | WO 96/16673 | 6/1996 |
| WO | WO 96/26964 | 9/1996 |
| WO | WO 96/27011 | 9/1996 |
| WO | WO 96/33208 | 10/1996 |
| WO | WO 97/10354 | 3/1997 |
| WO | WO 98/03546 | 1/1998 |
| WO | WO 98/50431 | 11/1998 |
| WO | WO 99/03495 | 1/1999 |
| WO | WO 99/10494 | 3/1999 |
| WO | WO 99/018212 | 4/1999 |
| WO | WO 99/51743 | 10/1999 |
| WO | WO 99/58572 | 11/1999 |
| WO | WO 99/67359 | 12/1999 |
| WO | WO 01/07918 | 2/2001 |
| WO | WO 01/19992 | 3/2001 |
| WO | WO 01/30854 | 5/2001 |
| WO | WO 01/82899 | 11/2001 |
| WO | WO 01/90192 | 11/2001 |
| WO | WO 02/06838 | 1/2002 |
| WO | WO 02/30463 | 4/2002 |
| WO | WO 02/33073 | 4/2002 |
| WO | WO 02/60919 | 8/2002 |
| WO | WO 03/00883 | 1/2003 |
| WO | WO 03/012069 | 2/2003 |
| WO | WO 03/020949 | 3/2003 |
| WO | WO 03/035835 | 5/2003 |
| WO | WO 03/042231 | 5/2003 |
| WO | WO 03/074679 | 9/2003 |
| WO | WO 03/087163 | 10/2003 |
| WO | WO 03/091424 | 11/2003 |
| WO | WO 2004/009618 | 1/2004 |
| WO | WO 2004/016740 | 2/2004 |
| WO | WO 2004/020579 | 3/2004 |
| WO | WO 2004/060919 | 7/2004 |
| WO | WO 2004/065611 | 8/2004 |
| WO | WO 2004/068931 | 8/2004 |
| WO | WO 2004/096273 | 11/2004 |
| WO | WO 2004/097041 | 11/2004 |
| WO | WO 2004/111233 | 12/2004 |
| WO | WO 2005/025615 | 3/2005 |
| WO | WO 2005/035753 | 4/2005 |
| WO | WO 2005/035754 | 4/2005 |
| WO | WO 2005/035756 | 4/2005 |
| WO | WO 2005/047327 | 5/2005 |
| WO | WO 2005/059106 | 6/2005 |
| WO | WO 2005/062916 | 7/2005 |
| WO | WO 2005/067620 | 7/2005 |
| WO | WO 2005/112564 | 12/2005 |
| WO | WO 2005/121180 | 12/2005 |
| WO | WO 2005/123126 | 12/2005 |
| WO | WO 2006/004663 | 1/2006 |
| WO | WO 2006/019447 | 2/2006 |
| WO | WO 2006/030200 | 3/2006 |
| WO | WO 2006/030220 | 3/2006 |
| WO | WO 2006/031370 | 3/2006 |
| WO | WO 2006/050491 | 5/2006 |
| WO | WO 2006/065208 | 6/2006 |
| WO | WO 2006/067913 | 6/2006 |
| WO | WO 2006/106903 | 10/2006 |
| WO | WO 2006/106905 | 10/2006 |
| WO | WO 2006/109592 | 10/2006 |
| WO | WO 2006/113767 | 10/2006 |
| WO | WO 2006/121852 | 11/2006 |
| WO | WO 2007/011746 | 1/2007 |
| WO | WO 2007/024535 | 3/2007 |
| WO | WO 2007/060411 | 5/2007 |
| WO | WO 2007/092772 | 8/2007 |
| WO | WO 2007/114319 | 10/2007 |
| WO | WO 2007/114325 | 10/2007 |
| WO | WO 2007/142325 | 12/2007 |
| WO | WO 2007/147901 | 12/2007 |
| WO | WO 2008/090960 | 7/2008 |
| WO | WO 2008/119353 | 10/2008 |
| WO | WO 2008/145142 | 12/2008 |
| WO | WO 2009/024653 | 2/2009 |
| WO | WO 2009 041613 | 4/2009 |
| WO | WO 2009/041621 | 4/2009 |
| WO | WO 2009/041643 | 4/2009 |
| WO | WO 2009/058492 | 5/2009 |
| WO | WO 2009/084659 | 7/2009 |
| WO | WO 2009/089004 | 7/2009 |
| WO | WO 2009/125825 | 10/2009 |
| WO | WO 2009/139822 | 11/2009 |
| WO | WO 2010/035769 | 4/2010 |
| WO | WO 2010/080065 | 7/2010 |
| WO | WO 2010/106180 | 9/2010 |
| WO | WO 2010/107109 | 9/2010 |
| WO | WO 2010/115589 | 10/2010 |
| WO | WO 2010/129304 | 11/2010 |
| WO | WO 2010/151792 | 12/2010 |
| WO | WO 2011/090088 | 2/2011 |
| WO | WO 2011/078332 | 6/2011 |
| WO | WO 2011/108502 | 9/2011 |
| WO | WO 2011/111007 | 9/2011 |
| WO | WO 2011/125674 | 10/2011 |
| WO | WO 2011/131746 | 10/2011 |
| WO | WO 2011/133886 | 10/2011 |
| WO | WO 2011/143545 | 11/2011 |
| WO | WO 2011/157283 | 12/2011 |
| WO | WO 2012/020096 | 2/2012 |
| WO | WO 2012/067176 | 5/2012 |
| WO | WO 2012/073985 | 6/2012 |
| WO | WO 2012/084829 | 6/2012 |
| WO | WO 2012/091023 | 7/2012 |
| WO | WO 2012/131555 | 10/2012 |
| WO | WO 2013/011076 | 1/2013 |
| WO | WO 2013/060867 | 5/2013 |
| WO | WO 2013/065708 | 5/2013 |
| WO | WO 2013/076186 | 5/2013 |
| WO | WO 2013/096291 | 6/2013 |
| WO | WO 2013/124450 | 8/2013 |
| WO | WO 2013/124451 | 8/2013 |
| WO | WO 2013/131866 | 9/2013 |
| WO | WO 2013/136186 | 9/2013 |
| WO | WO 2013/157954 | 10/2013 |
| WO | WO 2014/028354 | 2/2014 |
| WO | WO 2014/050926 | 4/2014 |
| WO | WO 2014/054804 | 4/2014 |
| WO | WO 2014/067011 | 5/2014 |
| WO | WO 2014/081955 | 5/2014 |
| WO | WO 2014/082179 | 6/2014 |
| WO | WO 2015/046467 | 4/2015 |
| WO | WO 2015/063339 | 5/2015 |
| WO | WO 2015/066700 | 5/2015 |
| WO | WO 2015/134894 | 9/2015 |
| WO | WO 2015/150447 | 10/2015 |
| WO | WO 2015/175874 | 11/2015 |
| WO | WO 2015/181805 | 12/2015 |
| WO | WO 2015/194233 | 12/2015 |
| WO | WO 2016/001810 | 1/2016 |
| WO | WO 2016/047652 | 3/2016 |
| WO | WO 2016/047656 | 3/2016 |
| WO | WO 2016/159213 | 10/2016 |
| WO | WO 2016/164708 | 10/2016 |
| WO | WO 2016/166014 | 10/2016 |
| WO | WO 2016/171202 | 10/2016 |

(56) References Cited

FOREIGN PATENT DOCUMENTS

| | | |
|---|---|---|
| WO | WO 2017/110980 | 6/2017 |
| WO | WO 2017/115773 | 7/2017 |
| WO | WO 2017/129585 | 8/2017 |
| WO | WO 2017/188356 | 11/2017 |
| WO | WO 2017/205014 | 11/2017 |
| WO | WO 2018/016881 | 1/2018 |
| WO | WO 2018/021450 | 2/2018 |
| WO | WO 2018/047813 | 3/2018 |
| WO | WO 2018/181870 | 10/2018 |
| WO | WO 2019/065795 | 4/2019 |
| WO | WO 2019/088143 | 5/2019 |
| WO | WO 2021/070885 | 4/2021 |

OTHER PUBLICATIONS

Reason, Donald C, and Jianhui Zhou. Biology direct vol. 1 24. Aug. 30, 2006, doi:10.1186/1745-6150-1-24 (Year: 2006).*
Muto, A., et al. Journal of Thrombosis and Haemostasis 12.2 (2014): 206-213 (Year: 2014).*
Morawska et al., "Ion exchange chromatography in monoclonal antibodies purification." Science Hub, Mabion Biologics CDMO, (2024) (Year: 2024).*
Liu, Hui F et al. "Recovery and purification process development for monoclonal antibody production." mAbs vol. 2,5 (2010): 480-99. doi: 10.4161/mabs.2.5.12645 (Year: 2010).*
Du, Yi et al. "Chromatographic analysis of the acidic and basic species of recombinant monoclonal antibodies." mAbs vol. 4,5 (2012): 578-85. doi: 10.4161/mabs.21328 (Year: 2024).*
Leblanc, Y., et al. "Charge variants characterization of a monoclonal antibody by ion exchange chromatography coupled on-line to native mass spectrometry: case study after a long-term storage at+ 5 C." Journal of Chromatography B 1048 (2017): 130-139 (Year: 2017).*
Spanov, Baubek, et al. "Analytical tools for the characterization of deamidation in monoclonal antibodies." Journal of Chromatography Open 2 (2022): 100025 (Year: 2022).*
Coskun, Ozlem. "Separation techniques: chromatography." Northern clinics of Istanbul 3.2 (2016): 156. (Year: 2016).*
Rathore, Anurag, and Ajoy Velayudhan. "Guidelines for optimization and scale-up in preparative chromatography." Biopharm international 16.1 (2003). (Year: 2003).*
U.S. Pat. No. 8,597,911, Miyazaki el al., issued Dec. 3, 2013 (abandoned).
U.S. Pat. No. 8,062,635, Hattori el al., issued Nov. 22, 2011.
U.S. Appl. No. 10/575,905, Hattori el al., filed Apr. 30, 2007 (abandoned).
U.S. Pat. No. 10,011,858, Igawa el al., issued Jul. 3, 2018.
U.S. Pat. No. 11,168,344, Igawa el al., issued Nov. 9, 2021.
U.S. Appl. No. 17/520,368, Hattori el al., filed Nov. 5, 2021.
U.S. Appl. No. 11/910,836, Hattori et al., filed Jan. 12, 2009 (abandoned).
U.S. Appl. No. 13/434,643, Hattori et al., filed Mar. 29, 2012 (abandoned).
U.S. Appl. No. 14/921,590, Hattori et al., filed Oct. 23, 2015 (abandoned).
U.S. Appl. No. 15/172,727, Hattori et al., filed Jun. 3, 2016 (abandoned).
U.S. Appl. No. 15/402,580, Hattori et al., filed Jan. 10, 2017 (abandoned).
U.S. Appl. No. 15/701,630, Hattori et al., filed Sep. 12, 2017 (abandoned).
U.S. Appl. No. 15/963,345, Hattori et al., filed Apr. 26, 2018 (abandoned).
U.S. Appl. No. 16/226,798, Hattori et al., filed Dec. 20, 2018 (abandoned).
U.S. Appl. No. 16/536,385, Hattori et al., filed Aug. 9, 2019 (abandoned).
U.S. Appl. No. 16/825,513, Hattori et al., filed Mar. 20, 2020 (abandoned).
U.S. Appl. No. 17/130,736, Hattori et al., filed Dec. 22, 2020 (abandoned).
U.S. Appl. No. 17/389,534, Hattori et al., filed Jul. 30, 2021.
U.S. Pat. No. 11,046,784, Igawa et al., issued Jun. 29, 2021.
U.S. Appl. No. 17/359,867, Igawa et al., filed Jun. 28, 2021.
U.S. Pat. No. 9,670,269, Igawa et al., issued Jun. 6, 2017.
U.S. Pat. No. 10,934,344, Igawa et al., issued Mar. 2, 2021.
U.S. Pat. No. 9,096,651, Igawa et al., issued Aug. 4, 2015.
U.S. Pat. No. 9,828,429, Igawa et al., issued Nov. 28, 2017.
U.S. Appl. No. 15/725,692, Igawa et al., filed Oct. 5, 2017.
U.S. Appl. No. 17/578,524, Igawa et al., filed Jan. 19, 2022.
U.S. Appl. No. 13/518,861, Igawa et al., filed Oct. 4, 2012 (abandoned).
U.S. Appl. No. 15/617,008, Igawa et al., filed Jun. 8, 2017 (abandoned).
U.S. Appl. No. 15/875,847, Igawa et al., filed Jan. 19, 2018 (abandoned).
U.S. Appl. No. 16/155,673, Igawa et al., filed Oct. 9, 2018 (abandoned).
U.S. Appl. No. 16/448,088, Igawa et al., filed Jun. 21, 2019 (abandoned).
U.S. Appl. No. 16/815,089, Igawa et al., filed Mar. 11, 2020 (abandoned).
U.S. Appl. No. 17/076,938, Igawa et al., filed Oct. 22, 2020 (abandoned).
U.S. Appl. No. 17/336,538, Igawa et al., filed Jun. 2, 2021 (abandoned).
U.S. Appl. No. 17/574,614, Igawa et al., filed Jan. 13, 2022.
U.S. Pat. No. 9,334,331, Igawa et al., issued May 10, 2016.
U.S. Appl. No. 14/019,117, Igawa et al., filed Sep. 5, 2013 (abandoned).
U.S. Appl. No. 14/019,712, Igawa et al., filed Sep. 6, 2013 (abandoned).
U.S. Pat. No. 10,450,381, Igawa et al., issued Oct. 22, 2019.
U.S. Appl. No. 15/288,965, Igawa et al., filed Oct. 7, 2016 (abandoned).
U.S. Appl. No. 16/459,791, Igawa et al., filed Jul. 2, 2019 (abandoned).
U.S. Appl. No. 17/485,818, Igawa et al., filed Sep. 27, 2021.
U.S. Pat. No. 11,124,576, Igawa et al., issued Sep. 21, 2021.
U.S. Appl. No. 15/319,016, Yoneyama, filed Dec. 15, 2016 (abandoned).
U.S. Appl. No. 16/432,790, Yoneyama, filed Jun. 5, 2019 (abandoned).
U.S. Appl. No. 16/780,977, Yoneyama, filed Feb. 4, 2020 (abandoned).
U.S. Appl. No. 17/017,971, Yoneyama, filed Sep. 11, 2020 (abandoned).
U.S. Appl. No. 17/235,445, Yoneyama, filed Apr. 20, 2021 (abandoned).
U.S. Appl. No. 17/534,566, Yoneyama, filed Nov. 24, 2021.
U.S. Pat. No. 11,150,254, Nogami et al., issued Oct. 19, 2021.
U.S. Pat. No. 11,214,623, Igawa et al., issued Jan. 4, 2022.
U.S. Pat. No. 11,142,587, Igawa et al., issued Oct. 12, 2021.
U.S. Appl. No. 17/483,898, Igawa et al., filed Sep. 24, 2021.
U.S. Appl. No. 16/061,429, Igawa et al., filed Jun. 12, 2018 (abandoned).
U.S. Appl. No. 17/563, 149, Igawa et al., filed Dec. 28, 2021.
U.S. Appl. No. 16/061,454, Tanaka et al., filed 12, 2018.
U.S. Appl. No. 16/093,495, Saeki et al., filed Oct. 12, 2018.
U.S. Pat. No. 10,759,870, Teranishi et al., issued Sep. 1, 2020.
U.S. Appl. No. 16/936,575, Teranishi et al., filed Jul. 23, 2020.
U.S. Appl. No. 16/318,883, Igawa et al., filed Jan. 18, 2019 (abandoned).
U.S. Appl. No. 17/528,371, Igawa et al., filed Nov. 17, 2021.
U.S. Appl. No. 16/496,089, Shima et al., filed Sep. 20, 2019.
U.S. Appl. No. 16/330,269, Yoneyama et al., filed Mar. 4, 2019.
U.S. Appl. No. 17/483,898, Igawa et al., Sep. 24, 2021.
U.S. Appl. No. 17/485,818, Igawa et al., Sep. 27, 2021.
U.S. Appl. No. 17/520,368, Igawa et al., Nov. 5, 2021.
U.S. Appl. No. 17/528,371, Igawa et al., Nov. 17, 2021.
U.S. Appl. No. 17/534,566, Yoneyama, Nov. 24, 2021.
U.S. Appl. No. 17/563,149, Igawa et al., Dec. 28, 2021.
U.S. Appl. No. 17/574,614, Igawa et al., Nov. 13, 2022.
U.S. Appl. No. 17/578,524, Igawa et al., Jan. 19, 2022.

(56) References Cited

OTHER PUBLICATIONS

Grapentin et al., "Protein-Polydimethylsiloxane Particles in Liquid Vial Monoclonal Antibody Formulations Containing Poloxamer 188," J Pharm Sci, Aug. 2020, 109(8):2393-2404.
Janeway, "The interaction of the antibody molecule with specific antigen," Immunobiology: The Immune System in Health and Disease, 2001, section 3.6, 5 pages.
Joshi et al., "Avoiding antibody aggregation during processing: establishing hold times," Biotechnol J, Sep. 2014, 9(9):1195-1205. doi: 10.1002/biot.201400052. Epub May 12, 2014.
Morris, "Epitope Mapping of Protein Antigens by Competition ELISA," The Protein Protocols Handbook, Jan. 1, 1996, pp. 595-600.
Ogiwara et al., "Anti FIXa/FX Bispecific Antibody (Emicizumab) Enhances Plasma Procoagulant Activity in Hemophilia B in the Presence of Very Low Level of Factor IX," Res Pract Thromb Haemost, 2017, 1.suppl 1:749.
Rajagopal et al., "Trehalose Limits Fragment Antibody Aggregation and Influences Charge Variant Formation in Spray-Dried Formulations at Elevated Temperatures," Mol Pharm, Jan. 7, 2019, 16(1):349-358. doi: 10.1021/acs.molpharmaceut.8b01002. Epub Dec. 17, 2018.
Yada et al., "Spotlight on emicizumab in the management of hemophilia A: patient selection and special considerations," J Blood Med, Jul. 2, 2019, 10:171-181.
U.S. Appl. No. 10/575,905, Hattori el al., Apr. 30, 2007 (abandoned).
U.S. Appl. No. 15/782,256, Igawa el al., filed Oct. 12, 2017.
U.S. Appl. No. 11/910,836, Hallori el al., filed Jan. 12, 2009 (abandoned).
U.S. Appl. No. 13/434,643, Hattori el al., filed Mar. 29, 2012 (abandoned).
U.S. Appl. No. 14/921,590, Hattori el al., filed Oct. 23, 2015 (abandoned).
U.S. Appl. No. 15/172,727, Hattori el al., filed Jun. 3, 2016 (abandoned).
U.S. Appl. No. 17/336,538, Igawa et al., filed Jun. 2, 2021.
U.S. Pat. No. 9,334,331, Igawa May 10, 2016.
U.S. Appl. No. 15/288,965, Igawa et Oct. 7, 2016 (abandoned).
U.S. Appl. No. 16/459,791, Igawa et al., filed Jul. 2, 2019.
U.S. Appl. No. 15/024,063, Igawa et filed Mar. 23, 2016.
U.S. Appl. No. 16/780,977, Yoneyama, filed Feb. 4, 2020.
U.S. Appl. No. 17/235,445, Yoneyama, filed Apr. 20, 2021.
U.S. Appl. No. 15/512,187, Nogami et al., filed Mar. 17, 2017.
U.S. Appl. No. 15/512,094, Igawa et Mar. 17, 2017.
U.S. Appl. No. 15/562,186, Igawa et al., filed 27, 2017.
U.S. Appl. No. 16/061,429, Igawa et al., filed Jun. 12, 2018.
U.S. Appl. No. 16/061,454, Tanaka et al., filed Jun. 12, 2018.
U.S. Appl. No. 16/318,883, Igawa et al., filed Jan. 18, 2019.
U.S. Appl. No. 14/921,590, Hattori et al., filed Oct. 23, 2015.
U.S. Appl. No. 15/172,727, Hattori et al., filed Jun. 3, 2016.
U.S. Appl. No. 16/008,486, Igawa et al., filed Jun. 14, 2018.
U.S. Appl. No. 17/389,534, Hattori et al., Jul. 30, 2021.
"Hemostatic Therapy Guideline for Inhibitor-negative Hemophilia Patients," Japanese Journal of Thrombosis and Hemostasis, 2013, 24(6):619-639 (with English translation).
"Hemostatic Therapy Guideline for Inhibitor-positive Hemophilia Patients," Japanese Journal of Thrombosis and Hemostasis, 2013, 24(6):640-658 (with English translation).
"National Haemophilia Foundation (NHF) Medical and Scientific Advisory Council (MASAC) Recommendations Concerning Prophylaxis," Medical Bulletin, 1994, No. 193, 1 page.
Abe et al., "Novel Protein A Resin: Synthetic Polymer Matrix Design Impact on Antibody Binding Capacity," JSR Technical Review, 2012, No. 119, pp. 1-5 (with English translation).
Abe et al., "Purification of monoclonal antibodies with light-chain heterogeneity produced by mouse hybridomas raised with NS-1 myelomas: application of hydrophobic interaction high-performance liquid chromatography," J Biochem Biophys Methods, Oct. 1993, 27:215-227.
Adams et al., "Humanization of a recombinant monoclonal antibody to produce a therapeutic HER dimerization inhibitor, pertuzumab," Cancer Immunol Immunother, 2006, 55:717-727.
Adlersberg et al., "The Immunoglobulin Hinge (Interdomain) Region," Ric Clin Lab, Jul.-Sep. 1976, 6(3):191-205.
Al-Banaa et al., "Emicizumab Use in Treatment of Acquired Hemophilia A: A Case Report," Am J Case Rep, Jul. 18, 2019, 20:1046-1048.
Algonomics—Tripole® applications [online] Retrieved from the Internet on Feb. 29, 2012: http://web.archive.org/web20090221052902/http://www.algonomics.com/proteinengineering/tripole applications. php, 2 pages (Feb. 21, 2009).
Allard et al., "Antigen binding properties of highly purified bispecific antibodies," Mol Immunol, Oct. 1992, 29(10):1219-1227.
Almagro et al., "Humanization of antibodies," Front Biosci, Jan. 1, 2008, 13:1619-33.
ALPROLIX® Intravenous, 2019, 16 pages (with English translation).
Amersdorfer et al., GenPept Accession No. AAC26541, Aug. 1, 2001, 1 page.
Amersham Biosciences, Protein Purification—Handbook, Edition AC, 2001, 98 pages.
Annex from opponent 2's submission of Jun. 7, 2018, 13 pages (document submitted by the opponent during the opposition proceedings of EP 2 202 245 on May 19, 2021).
Angal et al., "A single amino acid substitution abolishes the heterogeneity of chimeric mouse/human (IgG4) antibody," Mol Immunol, Jan. 1993, 30:105-108.
Antibodies in Example 29 of EP 2 202 245, 2 pages (document submitted by the opponent during the opposition proceedings of EP 2 202 245 on May 19, 2020).
Armour et al., "Recombinant human IgG molecules lacking Fcgamma receptor I binding and monocyte triggering activities," Eur J Immunol, Aug. 1999, 29(8):2613-2624.
Arndt et al., "Factors influencing the dimer to monomer transition of an antibody single-chain Fv fragment," Biochemistry, Sep. 15, 1998, 37(37):12918-12926.
Arndt et al., "Helix-stabilized Fv (hsFv) antibody fragments: substituting the constant domains of a Fab fragment for a heterodimeric coiled-coil domain," J Mol Biol, Sep. 7, 2001, 312:221-228.
Aslan et al., "Engineering a novel, stable dimeric streptavidin with lower isoelectric point," J Biotechnol, Feb. 1, 2007, 128(2):213-225.
Asselta et al., "Factor V Deficiency," Semin Thromb Hemost, Jun. 2009, 35:382-389.
"Hemophilia and Von Willebrand's disease: 2. Management Association of Hemophilia Clinic Directors of Canada," Association of Hemophilia Clinic Directors of Canada, Canadian Medical Association Journal, 1995, 153(2):147-157.
Astermark et al., "A randomized comparison of bypassing agents in hemophilia complicated by an inhibitor: the FEIBA NovoSeven Comparative (FENOC) Study," Blood, Jan. 15, 2007, 109(2):546-551. Epub Sep. 21, 2006.
Atwell et al., "Stable heterodimers from remodeling the domain interface of a homodimer using a phage display library," J Mol Biol, Jul. 4, 1997, 270:26-35.
Baerga-Ortiz et al., "Two different proteins that compete for binding to thrombin have opposite kinetic and thermodynamic profiles," Jan. 2004, Protein Sci, 2004, 13(1):166-176.
Bajaj et al., "A Monoclonal Antibody to Factor IX That Inhibits the Factor VIII: Ca Potentiation of Factor X Activation," J Biol Chem, Sep. 25, 1985, 260(21):11574-11580.
Baker et al., "Immunogenicity of protein therapeutics: The key causes, consequences and challenges," Self Nonself, Oct. 2010, 1(4):314-322.
Barrabes et al., "Effect of sialic acid content on glycoprotein p/ analyzed by two-dimensional electrophoresis," Electrophoresis, Sep. 2010, 31(17):2903-2912. doi: 10.1002/elps.200900764.
Bartelds et al., "Clinical response to adalimumab: relationship to anti-adalimumab antibodies and serum adalimumab concentrations in rheumatoid arthritis," Ann Rheum Dis, Jul. 2007, 66:921-926.

(56) References Cited

OTHER PUBLICATIONS

Batra et al., "Pharmacokinetics and biodistribution of genetically engineered antibodies," Curr Opin Biotechnol, Dec. 2002, 13(6):603-608.
Bebbington et al., "High-Level Expression of a Recombinant Antibody from Myeloma Cells Using a Glutamine Synthetase Gene as an Amplifiable Selectable Marker," Biotechnology (NY), Feb. 1992, 10:169-175.
Bender et al., "Immunogenicity, efficacy and adverse events of adalimumab in RA patients," Rheumatol Int, Jan. 2007, 27:269-274.
Bessos et al., "The characterization of a panel of monoclonal antibodies to human coagulation factor IX," Thrombosis Research, Dec. 15, 1985, 40:863-867.
Binz et al., "Engineering novel binding proteins from nonimmunoglobulin domains," Nat Biotechnol, Oct. 2005, 23:1257-1268.
Blazar, "Infusion of Anti-B7.1 (CD80) and Anti-B7.2 (CD86) Monoclonal Antibodies Inhibits Murine Graft-Versus-Host Disease Lethality in Part Via Direct Effects on CD4$^+$ and CD8$^+$ T Cells," J Immunol, Oct. 15, 1996, 157:3250-3259.
Bolton-Maggs et al., "Haemophilias A and B," The Lancet, May 24, 2003, 361:1801-1809.
Borrebaeck et al., "Antibody evolution beyond Nature," Nat Biotechnol, Dec. 2002, 20(12):1189-1190.
Bos et al., "Enhanced Transfection of a Bacterial Plasmid into Hybridoma Cells by Electroporation: Application for the Selection of Hybrid Hybridoma (Quadroma) Cell Lines," Hybridoma, Feb. 1992, 11:41-51.
Bowen, Haemophilia A and haemophilia B: molecular insights, Mol Pathol, Feb. 2002, 55(1):1-18.
Bowie et al., "Deciphering the Message in Protein Sequences: Tolerance to Amino Acid Substitutions," Science, Mar. 16, 1990, 247:1306-1310.
Branden et al., "Recognition of Foreign Molecules by the Immune System," Introduction to Protein Structure, 2d Ed., Garland Publishing, 1999, pp. 299-323.
Brandstetter et al., "X-ray structure of clotting factor IXa: active site and module structure related to Xase activity and hemophilia B," Proc Natl Acad Sci USA, Oct. 10, 1995, 92(21):9796-9800.
Brennan et al., "Preparation of Bispecific Antibodies by Chemical Recombination of Monoclonal Immunoglobulin G1 Fragments," Science, Jul. 5, 1985, 229(4708):81-83.
Brinkman et al. "Phospholipid-binding domain of factor VIII is involved in endothelial cell- mediated activation of factor X by factor IXa," Arterioscler Thromb Vasc Biol, Mar. 2002, 22(3):511-516.
Brown et al., "Tolerance of single, but not multiple, amino acid replacements in antibody $V_h$ CDR 2: a means of minimizing B cell wastage from somatic hypermutation?," J Immunol, May 1, 1996, 156(9):3285-3291.
Burges et al., "Effective relief of malignant ascites in patients with advanced ovarian cancer by a trifunctional anti-EpCAM x anti-CD3 antibody: a phase I/II study," Clin Cancer Res, Jul. 1, 2007, 13(13):3899-3905.
Burgess, "Possible dissociation of the heparin-binding and mitogenic activities of heparin-binding (acidic fibroblast) growth factor-1 from its receptor-binding activities by site-directed mutagenesis of a single lysine residue," J Cell Biol, Nov. 1990, 111:2129-2138.
CALBIOCHEM® Buffers, "A guide for the preparation and use of buffers in biological systems," by Chandra Mohan, Ph.D., Copyright © 2003 EMD Biosciences, Inc., an Affiliate of Merck KGaA, Darmstadt, Germany, 37 pages.
Cardoso et al., "Neutralizing Human Anti Crotoxin scFv Isolated from a Nonimmunized Phage Library," Scand J Immunol, Apr. 2000, 51(4):337-44.
Carter, "Bispecific human IgG by design," J Immunol Methods, Feb. 1, 2001, 248(1-2):7-15.
Chamow et al., "A humanized, bispecific immunoadhesin-antibody that retargets CD3+ effectors to kill HIV-1-infected cells," J Immunol, Nov. 1, 1994, 153(9):4268-4280.
Chatellier et al., "Functional mapping of conserved residues located at the VL and VH domain interface of a Fab," J Mol Biol, Nov. 22, 1996, 264(1):1-6.
Chau et al., "HuM291 (Nuvion), a humanized Fc receptor-nonbinding antibody against CD3, anergizes peripheral blood T cells as partial agonist of the T cell receptor," Transplantation, Apr. 15, 2001, 71(7):941-950.
Chen et al., "Selection and Analysis of an Optimized Anti-VEGF Antibody: Crystal Structure of an Affinity-matured Fab in Complex with Antigen," J Mol Biol, Nov. 1999, 293(4):865-881.
Chen et al., "Defective secretion of an immunoglobulin caused by mutations in the heavy chain complementarity determining region 2," J Exp Med, Aug. 1994, 180(2):577-586.
Chen et al., "Generation and analysis of random point mutations in an antibody CDR2 sequence: many mutated antibodies lose their ability to bind antigen," J Exp Med, Sep. 1992, 176(3):855-866.
Chirino et al., "Minimizing the immunogenicity of protein therapeutics," Drug Discov Today, Jan. 2004, 9:82-90.
Choi et al., "Crystal structures of immunoglobulin Fc heterodimers reveal the molecular basis for heterodimer formation," Mol Immunol, Jun. 2015, 65(2):377-383. doi: 10.1016/j.molimm. Feb. 17, 2015. Epub Mar. 2, 2015.
Choi et al., "Engineering of Immunoglobulin Fc Heterodimers Using Yeast Surface-Displayed Combinatorial Fc Library Screening," PLoS One, Dec. 16, 2015, 10(12):e0145349. doi: 10.1371/journal.pone.0145349. eCollection 2015.
Chu et al., "Accumulation of succinimide in a recombinant monoclonal antibody in mildly acidic buffers under elevated temperatures," Pharm Res, Jun. 2007, 24(6):1145-1156.
Cole et al., "Human IgG2 variants of chimeric anti-CD3 are nonmitogenic to T cells," J Immunol, Oct. 1, 1997, 159(7):3613-3621.
Coloma et al., "Position effects of variable region carbohydrate on the affinity and in vivo behavior of an anti-(1→6) dextran antibody," J Immunol, Feb. 15, 1999, 162(4):2162-2170.
Collins et al., "Implications of coagulation factor VIII and IX pharmaco-kinetics in the prophylactic treatment of haemophilia," Haemophilia, Jan. 2011, 17(1):2-10. doi: 10.1111/j.1365-2516.2010.02370.x. Epub Aug. 22, 2010.
Comper et al., "Charge selectivity in kidney ultrafiltration," Kidney Int, May 1995, 47:1242-1251.
Coppola et al., "Acquired Inhibitors of Coagulation Factors: Part I—Acquired Hemophilia A," Semin Thromb Hemost, Jul. 2012, 38(5):433-446. doi: 10.1055/s-0032-1315757. Epub Jun. 27, 2012.
Cordoba et al., "Non-enzymatic hinge region fragmentation of antibodies in solution," J Chromatogr B Analyt Technol Biomed Life Sci, Apr. 25, 2005, 818(2):115-121.
Couto et al., "Anti-BA46 Monoclonal Antibody Mc3: Humanization Using a Novel Positional Consensus and in Vivo and in Vitro Characterization," Cancer Res, Apr. 15, 1995, 55:1717-1722.
Cruse et al., Chapter 3 "Antigens and Immunogens," Atlas of Immunology, CRC Press LLC, 2004, p. 109.
Dahlback, "Blood coagulation," Lancet, May 6, 2000, 355(9215):1627-1632.
Dall'Acqua et al., "Antibody humanization by framework shuffling," Methods, May 2005, 36(1):43-60.
Dall'Acqua et al., "Properties of Human IgGls Engineered for Enhanced Binding to the Neonatal Fc Receptor (FcRn)", J Biol Chem, Aug. 18, 2006, 281(33):23514-23524. Epub Jun. 21, 2006.
Dall'Acqua et al., "Contribution of Domain Interface Residues to the Stability of Antibody CH3 Domain Homodimers," Biochemistry, Jun. 30, 1998, 37(26):9266-9273. doi: 10.1021/bi980270i. PMID: 9649307.
Damschroder et al., "Framework shuffling of antibodies to reduce immunogenicity and manipulate functional and biophysical properties," Mol Immunol, Apr. 2007, 44(11):3049-3060.
Dane et al., "Successful use of emicizumab in a patient with refractory acquired hemophilia A and acute coronary syndrome requiring percutaneous coronary intervention," Res Pract Thromb Haemost, Apr. 9, 2019, 3(3):420-423.
Davie, "A Brief Historical Review of the Waterfall/Cascade of Blood Coagulation," J Biol Chem, Dec. 19, 2003, 278(51):50819-50832. Epub Oct. 21, 2003.

(56) References Cited

OTHER PUBLICATIONS

Davie et al., "The coagulation cascade: Initiation, maintenance, and regulation," Biochemistry, Oct. 1991, 30(43):10363-10370.
Davies et al., "Antibody VH domains as small recognition units," Biotechnology (NY), May 1995, 13(5):475-479.
De Groot et al., "De-immunization of therapeutic proteins by T-cell epitope modification," Dev Biol (Basel), 2005, 122:171-194.
De Pascalis et al., "Grafting of 'abbreviated' complementary-determining regions containing specificity-determining residues essential for ligand contact to engineer a less immunogenic humanized monoclonal antibody," Journal of Immunology, Sep. 15, 2002, 169(6):3076-3084.
Decision of the Opposition Division for EP 2 006 381 on Jul. 25, 2018 (document cited in Ground of Appeal filed on Dec. 4, 2018 by the proprietor, Chugai Seiyaku Kabushiki Kaisha, in connection with the formal appeal lodged on Sep. 19, 2018), 17 pages.
Decision of the Opposition Division in EP 2 275 443, dated Apr. 26, 2018 (document submitted by the Patentee during opposition proceedings of EP 2 202 245 on May 24, 2019), 29 pages.
Declaration of Christian Beil, signed Jun. 18, 2020, 6 pages (document submitted by the opponent in the opposition proceedings of EP 3 050 963) 6 pages.
Declaration of Taichi Kuramochi, signed May 23, 2019, 11 pages (document submitted by the patentee in the opposition proceedings of EP 2 202 245 on May 24, 2019).
Declaration of Dr. Anette Henriksen, signed Apr. 17, 2019, 4 pages (document submitted by the opponent during the opposition proceedings of EP 2 006 381).
Deen et al., "Structural determinants of glomerular permeability," Am J Physiol Renal Physiol, Oct. 1, 2001, 281:F579-F596.
Del Rio et al., "An Engineered Penicillin Acylase with Altered Surface Charge Is More Stable in Alkaline pH," Ann NY Acad Sci, Oct. 12, 1996, 799:61-64.
Deng et al., "An Agonist Murine Monoclonal Antibody to the Human c-Mpl Receptor Stimulates Megakaryocytopoiesis," Blood, Sep. 15, 1998, 92:1981-1988.
Diaz et al., "Effects of engineering charged amino acids in the $C_H3$ domains on antibody heavy chain dimerization," Philippine Science Letters, May 27, 2011, 4(1):48-55.
Do et al., Protein Expr Purif, Aug. 2008, 60(2):147-150. doi: 10.1016/j.pep.2008.04.009. Epub May 3, 2008.
Dumont et al., "Monomeric Fc fusions: impact on pharmacokinetic and biological activity of protein therapeutics," BioDrugs, 2006, 20(3):151-160.
Edelman et al., "The Covalent Structure of an Entire γG Immunoglobulin Molecule," Proc Natl Acad Sci USA, May 1969, 63(1):78-85.
Edwards et al., "The Remarkable Flexibility of the Human Antibody Repertoire; Isolation of Over One Thousand Different Antibodies to a Single Protein, BLyS," J Mol Biol, Nov. 14, 2003, 334(1):103-18.
EPO Register Extract EP 1 915 397, 4 pages (document submitted in EP opposition and posted by EPO on Feb. 2, 2018).
Ewert et al., "Stability improvement of antibodies for extracellular and intracellular applications: CDR grafting to stable frameworks and structure-based framework engineering," Methods, Oct. 2004, 34:184-199.
Fay et al., Chapter 2B "Nonenzymatic cofactors: factor VIII," Comprehensive Biochemistry, 1986, 13:35-37.
Fay, "Activation of factor VIII and mechanisms of cofactor action," Blood Rev, Mar. 2004, 18(1):1-15.
"FDA Grants Roche Breakthrough Therapy Designation on Hemophilia Drug," BioPharm International, UBM, Apr. 19, 2018, 1 page, printed from the internet: bttp://www.biopharminternational.conp/fda-grants-roche-breakthrough-therapy-designation-hemophilia-drug.
Feige et al., "How antibodies fold," Trends Biochem Sci, Apr. 2010, 35(4):189-98. doi: 10.1016/j.tibs.2009.11.005. Epub Dec. 21, 2009.
Figini et al., "In vitro assembly of repertoires of antibody chains on the surface of phage by renaturation," J Mol Biol, May 27, 1994, 239(1):68-78.

Franchini et al., "Acquired haemophilia A: A 2013 update," Thromb Haemost, Dec. 2013, 110(6):1114-1120. doi:10.1160/TH13-05-0363. Epub Sep. 5, 2013.
Francois et al., "Construction of a Bispecific Antibody Reacting with the α- and β-Chains of the Human IL-2 Receptor," J Immunol, May 15, 1993, 150:4610-4619.
Fujii, "Antibody affinity maturation by random mutagenesis," Methods Mol Biol, 2004, 248:345-359.
GE Healthcare Life Sciences, "Dynamic binding capacity study on MabSelect SuRe™ LX for capturing high-titer monoclonal antibodies," Application note 28-9875-25-AA, 2011, retrieved from the internet on Feb. 17, 2017: <http://www.processdevelopmentforum.com/images/articles/28-9875-25_AA_AN_DBC_study_on_MabSelect_SuRe_LX_final.pdf>, 6 pages.
Gatiyatov et al., "Antiself Antibodies Against Blood Coagulation Factors," Siberian Medical Journal, Jun. 2011, 103(4):34-38 (with English translation).
Gelderman et al., "The inhibitory effect of CD46, CD55, and CD59 on complement activation after immunotherapeutic treatment of cervical carcinoma cells with monoclonal antibodies or bispecific monoclonal antibodies," Lab Invest, Apr. 2002, 82(4):483-493.
Gerstner et al., "Sequence plasticity in the antigen-binding site of a therapeutic anti-HER2 antibody," J Mol Biol, Aug. 30, 2002, 321(5):851-862.
Gessner et al., "The IgG Fc receptor family," Ann Hematol, Jun. 1998, 76:231-248.
Ghetie et al., "FcRn: the MHC class I-related receptor that is more than an IgG transporter," Immunol Today, Dec. 1997, 18:592-598.
Ghetie et al., "Increasing the serum persistence of an IgG fragment by random mutagenesis," Nat Biotechnol, Jul. 1997, 15:637-640.
Ghetie et al., "Multiple roles for the major histocompatibility complex class I—related receptor FcRn," Annu Rev Immunol, Apr. 2000, 18:739-766.
Gobburu et al., "Pharmacokinetics/dynamics of 5c8, a monoclonal antibody to CD154 (CD40 ligand) suppression of an immune response in monkeys," J Pharmacol Exp Ther, Aug. 1998, 286:925-930.
Goel et al., "Plasticity within the Antigen-Combining Site May Manifest as Molecular Mimicry in the Humoral Immune Response," J Immunol, Dec. 15, 2004, 173(12):7358-7367.
Golay et al., "Mechanism of action of therapeutic monoclonal antibodies: Promises and pitfalls of in vitro and in vivo assays," Archives of Biochemistry and Biophysics, Oct. 15, 2012, 526:146-153.
Golay et al., "Design and Validation of a Novel Generic Platform for the Production of Tetravalent IgG1-like Bispecific Antibodies," J Immunol, Apr. 1, 2016, 196(7):3199-3211.
Gonzales et al., "Minimizing the immunogenicity of antibodies for clinical application," Tumour Biol, Jan.-Feb. 2005, 26(1):31-43.
Goode et al., "The glomerular basement membrane charge-selectivity barrier: an oversimplified concept?" Nephrol Dial Transplant, Oct. 1996, 11:1714-1716.
Goulet et al., "Kinetic mechanism of controlled Fab-arm exchange for the formation of bispecific immunoglobulin G1 antibodies," J Biol Chem, Jan. 12, 2018, 293(2):651-661. doi: 10.1074/jbc.RA117.000303. Epub Nov. 17, 2017.
Gramer et al., "Production of stable bispecific IgG1 by controlled Fab-arm exchange: scalability from bench to large-scale manufacturing by application of standard approaches," mAbs, Nov.-Dec. 2013, 5(6):962-973. doi: 10.4161/mabs.26233. Epub Aug. 22, 2013.
Granted claims of EP 2 275 443, 1 page (document submitted by the patentee during the opposition proceedings of EP 2 202 245 on May 24, 2019).
Graves et al., "Molecular modeling and preclinical evaluation of the humanized NR-LU-13 antibody," Clin Cancer Res, Apr. 1999, 5:899-908.
Griffin et al., "Analysis of heavy and light chain sequences of conventional camelid antibodies from *Camelus dromedarius* and *Camelus bactrianus* species," J Immunol Methods, Mar. 2014, 405:35-46. doi: 10.1016/j.jim.2014.01.003. Epub Jan. 18, 2014.
Griffiths et al., "Human anti-self antibodies with high specificity from phage display libraries," EMBO J, Feb. 1993, 12(2):725-734.

(56) References Cited

OTHER PUBLICATIONS

Grosse-Hovest et al., "A recombinant bispecific single-chain antibody induces targeted, supra-agonistic CD28-stimulation and tumor cell killing", European Journal of Immunology, Apr. 22, 2003, 33(5):1334-1340.
Guidelines for the Management of Hemophilia, World Federation of Hemophilia, 2005, 52 pages.
Gunasekaran et al., "Enhancing antibody Fc heterodimer formation through electrostatic steering effects: applications to bispecific molecules and monovalent IgG," J Biol Chem, Jun. 18, 2010, 285(25):19637-19646.
Gupta et al., "Affinity chromatography and co-chromatography of bispecific monoclonal antibody immunoconjugates," J Biochem Biophys Methohads, May 31, 2002, 51:203-216.
Guyre et al., "Increased potency of Fc-receptor-targeted antigens," Cancer Immunol Immunother, Nov. 1997, 45(3-4):146-148.
Haagen et al., "Unprimed CD4+ and CD8+ T cells can be rapidly activated by a CD3 x CD19 bispecific antibody to proliferate and become cytotoxic," Cancer Immunol Immunother, Dec. 1994, 39(6):391-396.
Hagiwara et al., "Effect of Emicizumab in improving coagulation ability in the presence of minor amount of Factor IX," Japanese Journal of Thrombosis and Hemostasis, 2017, 28(2):190 0-012 (with English translation).
Hamers-Casterman et al., "Naturally occurring antibodies devoid of light chains," Nature, Jun. 3, 1993, 363(6428):446-448.
HÄMMERLING et al., "Use of Hybrid Antibody with Anti-γG and Anti-Ferritin Specificities in Locating Cell Surface Antigens by Electron Microscopy," J Exp Med, Dec. 1, 1968, 128:1461-1473.
Hardisty et al., "A One-stage Factor VIII (Antihaemophilic Globulin) Assay and its Use on Venous and Capillary Plasma," Thromb Diath Haemorrh, May 15, 1962, 7:215-228.
Hattori, "Introduction of ART-Ig and application to hemophilia A treatment," Chugai Pharmaceutical Co., Ltd., Dec. 2012, 18: 42-57 (with English translation).
He et al., "Humanization and pharmacokinetics of a monoclonal antibody with specificity for both E-and P-selectin," J Immunol, Jan. 15, 1998, 160:1029-1035.
Helfrich et al., "A rapid and versatile method for harnessing scFv antibody fragments with various biological effector functions," J Immunol Methods, Apr. 3, 2000, 237(1-2):131-145.
Helguera et al., "Antibody-Cytokine Fusion Proteins for the Therapy of Cancer," Methods Mol Med, 2005, 109:347-374. doi: 10.1385/1-59259-862-5:347. PMID: 15585931.
Hemlibra (emicizumab-kxwh) Prescribing Information, U.S. Food and Drug Administration, Nov. 2017, 16 pages.
Hinton et al., "An engineered human IgG1 antibody with longer serum half-life," J Immunol, Jan. 1, 2006, 176:346-356.
Hinton et al., "Engineered human IgG antibodies with longer serum half-lives in primates," J Biol Chem, Feb. 20, 2004, 279(8):6213-6216.
Hird et al., "Tumour localisation with a radioactively labelled reshaped human monoclonal antibody," Br J Cancer, Nov. 1991, 64(5):911-914.
Ho et al., "In vitro antibody evolution targeting germline hot spots to increase activity of an anti- CD22 immunotoxin," J Biol Chem, Jan. 7, 2005, 280(1):607-617. doi: 10.1074/jbc.M409783200. Epub Oct. 18, 2004.
Hoad et al. "Characterization of monoclonal antibodies to human factor X.Xa: Initial observations with a quantitative ELISA procedure," J Immunol Methods, Feb. 15, 1991, 136(2):269-278.
Holliger et al., "'Diabodies': Small bivalent and bispecific antibody fragments," Proc Natl Acad Sci USA, Jul. 1993, 90:6444-6448.
Hombach et al., "A CD16/CD30 bispecific monoclonal antibody induces lysis of Hodgkin's cells by unstimulated natural killer cells in vitro and in vivo," Int J Cancer, Nov. 11, 1993, 55:830-836.
Hong et al., "Enhanced cellular uptake and transport of polyclonal immunoglobulin G and fab after their cationization," J Drug Target, 2000, 8(2):67-77.
Hotzel et al., "A strategy for risk mitigation of antibodies with fast clearance," mAbs, Nov.-Dec. 2012, 4(6):753-760. doi: 10.4161/mabs.22189.
Hozumi et al., "Evidence for somatic rearrangement of immunoglobulin genes coding for variable and constant regions," Proc Natl Acad Sci USA, Oct. 1976, 73(10):3628-3632.
Hsia et al., "Treatment of acquired factor X inhibitor by plasma exchange with concomitant intravenous immunoglobulin and corticosteroids," Apr. 2008, Am J Hematol, 83:318-320.
Hu et al., "Development and characterization of a novel fusion protein composed of a human IgG1 heavy chain constant region and a single-chain fragment variable antibody against Venezuelan equine encephalitis virus," J Biochem, Jan. 1, 2003, 133(1):59-66.
Hugo et al., "Functional aspects of co-variant surface charges in an antibody fragment," Protein Sci, Nov. 2002, 11(11):2697-2705. doi: 10.1110/ps.0209302. PMID: 12381851; PMCID: PMC2373727.
Huse et al., "Generation of a Large Combinatorial Library of the Immunoglobulin Repertoire in Phage Lambda," Science, Dec. 8, 1989, 246:1275-1281.
Hwang et al., "Use of human germline genes in a CDR homology-based approach to antibody humanization," Methods, May 2005, 36:35-42.
Igawa, "Next Generation Antibody Therapeutics Using Bispecific Antibody Technology," The Pharmaceutical Society of Japan, Jul. 1, 2017, vol. 137, pp. 831-836 (with English translation).
Igawa et al., "Generation of a Novel Bispecific Antibody (ACE910) Against Activated Factor IX and Factor X Mimicking the Function of Factor VIII Cofactor Activity," Blood, Nov. 16, 2012, vol. 120, No. 21, p. 1126.
Igawa et al., "VH/VL interface engineering to promote selective expression and inhibit conformational isomerization of thrombopoietin receptor agonist single-chain diabody," Protein Eng Des Sel, Aug. 2010, 23(8):667-677. doi: 10.1093/protein/gzq034. Epub Jun. 24, 2010.
Igawa, "Technological Development of Bispecific Antibodies and Creation of Pharmaceuticals," Experimental Medicine, Jul. 1, 2018, 36:1823-1829 (with English translation).
Igawa, "Innovative Technology to develop Bispecific Antibody," CSJ Current Review, Aug. 30, 2018, 17:157-163 (with English translation).
IMGT Scientific charts depicting the correspondence between Eu and Kabat numberings for the human IgG constant region, created May 17, 2001 and last updated Aug. 13, 2014 (Exhibit A).
IMGT Scientific charts depicting the correspondence between Eu and Kabat numberings for the human IgG constant region, created May 17, 2001 and last updated Aug. 13, 2014 (Exhibit B).
Ito et al., "The His-probe method: effects of histidine residues introduced into the complementarity-determining regions of antibodies on antigen-antibody interactions at different pH values," FEBS Lett, Aug. 1992, 309:85-88.
Iwahashi et al., "CDR substitutions of a humanized monoclonal antibody (CC49): contributions of individual CDRs to antigen binding and immunogenicity," Mol Immunol, Oct. 1999-Nov. 36(15-16):1079-1091.
Jackman et al., "Development of a two-part strategy to identify a therapeutic human bispecific antibody that inhibits IgE receptor signaling," J Biol Chem, Jul. 2, 2010, 285(27): 20850-20859. doi: 10.1074/jbc.M110.113910. Epub May 5, 2010.
Jain et al., "Engineering antibodies for clinical applications," Trends Biotechnol, Jul. 2007, 25(7):307-316.
Janeway et al., Chapter 3 "Structure of the Antibody Molecule and Immunoglobulin Genes," Immunobiology, 3rd Edition, Garland Press, 1997, 3:1-3:11.
Janeway et al., Chapter 3 "Antigen Recognition by B-cell and T-cell Receptors," Immunobiology, 5th edition, 2001, pp. 93-122.
Janeway et al., Chapter 4 "The Generation of Lymphocyte Antigen Receptors," Immunobiology, 5th edition, 2001, pp. 123-154.
Jendeberg et al., "Engineering of Fc(1) and Fc(3) from human immunoglobulin G to analyse subclass specificity for staphylococcal protein A," J Immunol Methods, Feb. 14, 1997, 201(1):25-34.
Jirholt et al., "Exploiting sequence space: shuffling in vivo formed complementarity determining regions into a master framework," Gene, Jul. 30, 1998, 215(2):471-476.

(56) References Cited

OTHER PUBLICATIONS

Johnson et al., "Cation exchange-HPLC and mass spectrometry reveal C-terminal amidation of an IgG1 heavy chain," Anal Biochem, Jan. 1, 2007, 360:75-83.

Johnson et al., "Kabat Database and its applications: 30 years after the first variability plot," Nucleic Acids Research, Jan. 1, 2000, 28(1):214-218.

Jones et al., "Identification and removal of a promiscuous CD4+ T cell epitope from the C1 domain of factor VIII," Thromb Haemost, Apr. 29, 2005, 3:991-1000.

Jung et al., "The importance of framework residues H6, H7 and H10 in antibody heavy chains: experimental evidence for a new structural subclassification of antibody V(H) domains," J Mol Biol, Jun. 8, 2001, 309(3):701-716.

Kabat et al., Sequence of Proteins of Immunological Interest, 5$^{th}$ Edition, 1991, pp. 690 and 693.

Kabsch et al., "On the use of sequence homologies to predict protein structure: identical pentapeptides can have completely different conformations," Proc Natl Acad Sci USA, Feb. 1984, 81(4):1075-1078.

Kang et al., "Linkage of recognition and replication functions by assembling combinatorial antibody Fab libraries along phage surfaces," Proc Natl Acad Sci USA, May 1991, 88:4363-4366.

Kanyavuz et al., "Breaking the law: unconventional strategies for antibody diversification," Nat Rev Immunol, Jun. 2019, 19(6):355-368. doi: 10.1038/S41577-019-0126-7.

Karpovsky et al., "Production of Target-Specific Effector Cells Using Hetero-Cross-Linked Aggregates Containing Anti-Target Cell and Anti-Fcγ Receptor Antibodies," J Exp Med, Dec. 1984, 160:1686-1701.

Kashmiri et al., "Generation, characterization, and in vivo studies of humanized anticarcinoma antibody CC49," Hybridoma, Oct. 1995, 14:461-473.

Kasper et al., "A More Uniform Measurement of Factor VIII Inhibitors," Thromb Diath Haemorrh. Dec. 15, 1975, 34(3):869-872.

Katayose et al., "MUC1-specific targeting immunotherapy with bispecific antibodies: inhibition of xenografted human bile duct carcinoma growth," Cancer Res, Sep. 15, 1996, 56(18):4205-4212.

Kenanova et al., "Tailoring the pharmacokinetics and positron emission tomography imaging properties of anti-carcinoembryonic antigen single-chain Fv-Fc antibody fragments," Cancer Res, Jan. 15, 2005, 65(2):622-631.

Kerschbaumer et al., "An antibody specific for coagulation factor IX enhances the activity of the intrinsic factor X-activating complex," J Biol Chem, Sep. 24, 2004, 279(39):40445-40450.

Khalifa et al., "Effects on interaction kinetics of mutations at the VH-VL interface of Fabs depend on the structural context," J Mol Recognit, May-Jun. 2000, 13(3):127-139.

Khawli et al., "Improved tumor localization and radioimaging with chemically modified monoclonal antibodies," Cancer Biother Radiopharm, Jun. 1996, 11:203-215.

Kim et al., "Antibody Engineering for the Development of Therapeutic Antibodies," Mol Cells, Aug. 31, 2005, 20:17-29.

Kim et al., "Chemical modification to reduce renal uptake of disulfide-bonded variable region fragment of anti-tac monoclonal antibody labeled with 99mTc," Bioconjugate Chem, May-Jun. 1999,10:447-453.

Kim et al., "Lowering of pI by acylation improves the renal uptake of 99mTc-labeled anti-Tac dsFv: effect of different acylating reagents," Nucl Med Biol, Nov. 2002, 29:795-801.

Kim et al., "Mammalian type I interferon receptors consists of two subunits: IFNaR1 and IFNaR2," Gene, Sep. 1, 1997, 196:279-286.

Kim et al., "Mapping the site on human IgG for binding of the MHC class I-related receptor, FcRn," Eur J Immunol, Sep. 1999, 29(9):2819-2825.

Kim et al., "Antibody light chain variable domains and their biophysically improved versions for human immunotherapy," mAbs, Jan.-Feb. 2014, 6(1):219-235. doi: 10.4161/mabs.26844.

Kipriyanov et al., "Bispecific tandem diabody for tumor therapy with improved antigen binding and pharmacokinetics," J Mol Biol, Oct. 15, 1999, 293(1):41-56.

Kipriyanov et al., "Effect of Domain Order on the Activity of Bacterially Produced Bispecific Single-chain Fv Antibodies," J Mol Biol, Jun. 27, 2003, 330(1):99-111.

Kitazawa et al., "Factor VIIIa-mimetic cofactor activity of a bispecific antibody to factors IX/Ixa and X/Xa, emicizumab, depends on its ability to bridge the antigens," Thromb Haemost, Jun. 28, 2017, 117(7):1348-1357. doi: 10.1160/TH17-01-0030. Epub Apr. 28, 2017.

Kitazawa, "Bispecific FIX-FX antibody for bypass therapy," 12th Workshop on Novel Technologies and Gene Transfer for Hemophilia, National Hemophilia Foundation, Oct. 24, 2014, 4 pages.

Kitazawa, "Bispecific FIX-FX antibody for bypass therapy," 12th NHF Workshop on New Technologies and Gene Therapies, Chugai Pharmaceutical Co., Ltd, Oct. 24, 2014, 11 pages.

Klein et al., "Progress in overcoming the chain association issue in bispecific heterodimeric IgG antibodies," mAbs, Nov.-Dec. 2012, 4(6):653-663. doi: 10.4161/mabs.21379. Epub Aug. 27, 2012.

Knoebl et al., "Emicizumab for the treatment of acquired hemophilia A," Blood, Jan. 21, 2021, 137(3):410-419.

Kobayashi et al., "The pharmacokinetic characteristics of glycolated humanized anti-Tac Fabs are determined by their isoelectric points," Cancer Res, Jan. 15, 1999, 59:422-430.

Komissarov et al., "Site-specific mutagenesis of a recombinant anti-single-stranded DNA Fab. Role of heavy chain complementarity-determining region 3 residues in antigen interaction," J Biol Chem, Oct. 24, 1997, 272(43):26864-26870.

Kontermann, "Recombinant bispecific antibodies for cancer therapy," Acta Pharmacol Sin, Jan. 2005, 26(1):1-9.

Korn et al., "Recombinant bispecific antibodies for the targeting of adenoviruses to CEA-expressing tumour cells: a comparative analysis of bacterially expressed single-chain diabody and tandem scFv," J Gene Med, Jun. 2004, 6:642-651.

Kranenborg et al., "Development and characterization of anti-renal cell carcinoma x antichelate bispecific monoclonal antibodies for two-phase targeting of renal cell carcinoma," Cancer Res, 1995, 55:5864s-5867s.

Kreutz et al., "Efficient bispecific monoclonal antibody purification using gradient thiophilic affinity chromatography," J Chromatogr B, Sep. 4, 1998, 714:161-170.

Krudysz-Amblo et al., "Quantitation of anti-factor VIII antibodies in human plasma," Blood, Mar. 12, 2009, 113(11):2587-2594. doi: 10. 1182/Blood-2008-08-174987. Epub Jan. 14, 2009.

Kroesen et al., "Phase I study of intravenously applied bispecific antibody in renal cell cancer patients receiving subcutaneous interleukin 2," Br J Cancer, Oct. 1994, 70:652-661.

Kruse-Jarres, "Inhibitors: our greatest challenge. Can we minimize the incidence?," Haemophilia, Jan. 19, 2013, Suppl 1:2-7. doi: 10.1111/hae.12049.

Kufer et al., "A revival of bispecific antibodies," Trends Biotechnol, May 1, 2004, 22(5):238-244.

Kumar et al., "The second PDZ domain of INAD is a type I domain involved in binding to eye protein kinase C. Mutational analysis and naturally occurring variants," J Biol Chem, Jul. 6, 2001, 276(27):24971-24977. Epub May 7, 2001.

Kurfis et al., "Role of Arg182 in the second extracellular loop of angiotensin II receptor AT2 in ligand binding," Biochem Biophys Res Commun, Oct. 5, 1999, 263:816-819.

Kurokawa et al., "Enhanced Fibrinolysis by a Bispecific Monoclonal Antibody Reactive to Fibrin and Tissue Plasminogen Activator," Bio/Technology, Nov. 1, 1989, 7:1163-1167.

Labrijn et al., "Therapeutic IgG4 antibodies engage in Fab-arm exchange with endogenous human IgG4 in vivo," Nat Biotechnol, Aug. 2009, 27(8):767-771.

Labrijn et al., "Controlled Fab-arm exchange for the generation of stable bispecific IgG1," Nat Protoc, Oct. 2014, 9(10):2450-2463. doi: 10.1038/nprot.2014.169. Epub Sep 25, 2014.

Labrijn et al., "Efficient generation of stable bispecific IgGI by controlled Fab-arm exchange," Pro Natl Acad Sci USA, Mar. 26, 2013, 110(13):5145-5150. doi: 10.1073/pnas.1220145110. Epub Mar. 11, 2013.

(56) References Cited

OTHER PUBLICATIONS

Labrijn et al., "Species-specific determinants in the IgG CH3 domain enable Fab-arm exchange by affecting the noncovalent CH3—CH3 interaction strength," J Immunol, Sep. 15, 2011, 187(6):3238-3246. doi: 10.4049/jimmunol.1003336. Epub Aug. 12, 2011.
Lacroix-Desmazes et al., "Dynamics of factor VIII interactions determine its immunologic fate in hemophilia A," Blood, Jul. 15, 2008, 112(2):240-249. doi: 10.1182/blood-2008-02-124941. Epub May 9, 2008.
Lansdorp et al., "Purification and analysis of bispecific tetrameric antibody complexes," Mol Immunol, Jul. 1990, 27:659-666.
Lapan et al., "Interaction of the A1 Subunit of Factor VIIIa and the Serine Protease Domain of Factor X Identified by Zero-length Cross-linking," Thromb Haemost, Sep. 1998, 80:418-422.
Lazar et al., "Transforming growth factor alpha: mutation of aspartic acid 47 and leucine 48 results in different biological activities," Mol Cell Biol, Mar. 1988, 8:1247-1252.
Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and Immune Response," J Nucl Med, Oct. 1993, 34:1662-1671.
Le Gall et al., "Effect of linker sequences between the antibody variable domains on the formation, stability and biological activity of a bispecific tandem diabody," Protein Eng Des Sel, Apr. 2004, 17(4):357-366. Epub May 4, 2004.
Lebégue et al., "Production and characterization of hybrid monoclonal antibodies with IgG1/IgG3 double isotype," C R Acad Sci III, 1990, 310(9):377-382.
Lenting et al., "The life cycle of coagulation factor VIII in view of its structure and function", Blood, Dec. 1, 1998, 92(11):3983-3996.
Leong et al., "Adapting pharmacokinetic properties of a humanized anti-interleukin-8 antibody for therapeutic applications using site-specific pegylation," Cytokine, Nov. 7, 2001, 16(3):106-119.
Lescar et al., "Crystal Structure of a Cross-reaction Complex between Fab 59.13.7 and Guinea Fowl Lysozyme," Journal of Biological Chemistry, Jul. 28, 1995, 270(30):18067-18076.
Li et al., "Construction and characterization of a humanized anti-human CD3 monoclonal antibody 12F6 with effective immunoregulation functions," Immunology, Dec. 2005, 116(4):487-498.
Life Technologies (Invitrogen: "ecdysone analogue" and pIND plasmid), Aug. 10, 2012, 2 pages.
Lillicrap, "von Willebrand disease: advances in pathogenetic understanding, diagnosis and therapy," Blood, Nov. 28, 2013, 122(23):3735-3740. doi: 10.1182/blood-2013-06-498303. Epub Sep. 24, 2013.
Lin et al., "Preclinical pharmacokinetics, interspecies scaling, and tissue distribution of a humanized monoclonal antibody against vascular endothelial growth factor," J Pharmacol Exp Ther, Jan. 1999, 288(1):371-378.
Lindhofer et al., "Preferential Species-Restricted Heavy/Light Chain Pairing in Rat/Mouse Quadromas," J Immunol, Jul. 1, 1995, 155:219-225.
Lindsay, Chapter 4 "Determination of the Kinetics and Mechanism of tg-FIX Activation by Factor XIa," 2004, pp. 49-75.
Link et al., "Production and Characterization of a Bispecific IgG Capable of Inducing T-Cell-Mediated Lysis of Malignant B Cells," Blood, Jun. 15, 1993, 81:3343-3349.
Liu et al., "Functional interactions between arginine-133 and aspartate-88 in the human reduced folate carrier: evidence for a charge-pair association," Biochem J, Sep. 1, 2001, 358(Pt 2):511-516.
Liu et al., "Heterogeneity of monoclonal antibodies," J Pharm Sci, Jul. 2008, 97(7):2426-2447.
Lloyd et al., "The production of a bispecific anti-CEA, anti-hapten (4-amino-phthalate) hybrid- hybridoma," J Natl Med Assoc, Oct. 1991, 83(10):901-904.
Lloyd et al., "Modelling the human immune response: performance of a $10^{11}$ human antibody repertoire against a broad panel of therapeutically relevant antigens," Protein Eng Des Sel, Mar. 2009, 22(3):159-168. doi: 10.1093/protein/gzn058. Epub Oct. 29, 2008.
Lobo et al., "Antibody pharmacokinetics and pharmacodynamics," J Pharm Sci, Nov. 2004, 93:2645-2668.
Löfqvist et al., "Haemophilia prophylaxis in young patients—a long-term follow-up," J Intern Med, May 1997, 241:395-400.
Lu et al., "Di-diabody: a novel tetravalent bispecific antibody molecule by design," J Immunol Methods, Aug. 2003, 279:219-232.
Lu et al., "Fab-scFv fusion protein: an efficient approach to production of bispecific antibody fragments," J Immunol Methods, Sep. 15, 2002, 267:213-226.
Lund et al., "Multiple interactions of IgG with its core oligosaccharide can modulate recognition by complement and human Fc gamma receptor I and influence the synthesis of its oligosaccharide chains," The Journal of Immunology, Dec. 1, 1996, 157(11):4963-4969.
MacCallum et al., "Antibody-antigen interactions: contact analysis and binding site topography," J Mol Biol, Oct. 11, 1996, 262:732-745.
Maeda et al., "Novel Antibody Modification Techniques and their Application to Antibody Therapeutics," Farumashia, 2015, vol. 51, pp. 424-428 (with English translation).
Maeda et al., "pH-dependent receptor/ligand dissociation as a determining factor for intracellular sorting of ligands for epidermal growth factor receptors in rat hepatocytes," J Control Release, Jul. 18, 2002, 82(1):71-82.
Mahlangu et al., "Emicizumab Prophylaxis in Patients Who Have Hemophilia A without Inhibitors," N Engl J Med, Aug. 30, 2018, 379(9):811-822.
Maini et al., "Double-blind randomized controlled clinical trial of the interleukin-6 receptor antagonist, tocilizumab, in European patients with rheumatoid arthritis who had an incomplete response to methotrexate," Arthritis Rheum, Sep. 2006, 54:2817-2829.
Maity et al., "Equilibrium unfolding of dimeric and engineered monomeric forms of Cro (F58W) repressor and the effect of added salts: evidence for the formation of folded monomer induced by sodium perchlorate," Arch Biochem Biophys, Feb. 1, 2005, 434(1):93-107.
Male et al., Chapter 3 "Antibodies," Immunology, 7th Edition, 2006, pp. 59-86.
Manco-Johnson et al., "Prophylaxis versus Episodic Treatment to Prevent Joint Disease in Boys with Severe Hemophilia," N Engl J Med, Aug. 9, 2007, 357(6):535-544.
Manz et al., Bioanalytical Chemistry, World Scientific Publishing Co., 2003, 1 page.
Manzke et al., "Single-step purification of bispecific monoclonal antibodies for immunotherapeutic use by hydrophobic interaction chromatography," J Immunol Methods, Oct. 13, 1997, 208:65-73.
Mariuzza, "The Structural Basis of Antigen-Antibody Recognition," Annu Rev Biophys Chem, 1987, 16:139-159.
Marshall et al., "Rational design and engineering of therapeutic proteins," Drug Discov Today, Mar. 1, 2003, 8(5):212-221.
Marti et al., "Inverse electrostatic effect: electrostatic repulsion in the unfolded state stabilizes a leucine zipper," Biochemistry, Sep. 11, 2004, 43(39):12436-12447.
Martin et al., "Crystal structure at 2.8 A of an FcRn/heterodimeric Fc complex: mechanism of pH-dependent binding," Mol Cell, Apr. 2001, 7:867-877.
Marvin et al., "Recombinant approaches to IgG-like bispecific antibodies," Acta Pharmacol Sin, Jun. 2005, 26:649-658.
Marvin et al., "Redesigning an antibody fragment for faster association with its antigen," Biochemistry, May 17, 2003, 42:7077-7083.
Massino et al., "Quantitative analysis of the products of IgG chain recombination in hybrid hybridomas based on affinity chromatography and radioimmunoassay," J Immunol Methods, Feb. 14, 1997, 201:57-66.
Mazor et al., "Improving target cell specificity using a novel monovalent bispecific IgG design," mAbs, Mar./Apr. 2015, 7(2):377-389.
McCafferty et al., "Phage antibodies: filamentous phage displaying antibody variable domains," Nature, Dec. 6, 1990, 348:552-554.

(56) References Cited

OTHER PUBLICATIONS

McPhee et al., "Engineering human immunodeficiency virus 1 protease heterodimers as macromolecular inhibitors of viral maturation," Proc Natl Acad Sci USA, Oct. 15, 1996, 93(21):11477-11481.

Medesan et al., "Delineation of the amino acid residues involved in transcytosis and catabolism of mouse IgG1," J Immunol, Mar. 1, 1997, 158(5):2211-2217.

Menegatti et al., "Factor X Deficiency," Semin Thromb Hemost, Jun. 2009, 35:407-415.

Merchant et al., "An efficient route to human bispecific IgG," Nat Biotechnol, Jul. 1998, 16:677-681.

Mertens et al., "Factor VIII-Factor IX Interactions: Molecular Sites Involved in Enzyme-Cofactor Complex Assembly," Thromb Haemost, Aug. 1999, 82:209-217.

Michaelsen et al., "A mutant human IgG molecule with only one C1q binding site can activate complement and induce lysis of target cells," Eur J Immunol., Jan. 2006, 36(1):129-138.

Milstein et al., "Hybrid hybridomas and their use in immunohistochemistry," Nature, Oct. 1983, 305:537-540.

Minami et al., "Bispecific Antibody ACE910 Improves Coagulation Function in Plasma of Patients with Factor XI-Deficiency," Japanese Journal of Thrombosis and Hemostasis, 2015, 26(2):188 0-024 (with English translation).

Miyata, "Factor IX Abnormality—Molecular Defects of Factor IX," Japanese Journal of Thrombosis and Hemostasis, 1991, 2(1):1-11 (with English translation).

Miyazaki et al., "Generation of bispecific IgG, which mimics the cofactor function of blood coagulation factor VIII," Seikagaku, 2006, 2P-B-161.

Mohnle et al., "Emicizumab in the Treatment of Acquired Haemophilia: A Case Report," Transfus Med Hemother, Apr. 2019, 46(2):121-123.

Morell et al., "Metabolic properties of IgG subclasses in man," J Clin Invest, Apr. 1, 1970, 49(4):673-880.

Morimoto et al., "Single-step purification of F(ab')2 fragments of mouse monoclonal antibodies (immunoglobulins G1) by hydrophobic interaction high performance liquid chromatography using TSK gel Phenyl-5PW," J Biochem Biophys Methods, 1992, 24:107-117.

Morrison, "Two heads are better than one," Nat Biotechnol, Nov. 2007, 25(11):1233-1234.

Muller et al., "The first constant domain (CH1 and CL) of an antibody used as heterodimerization domain for bispecific miniantibodies," FEBS Lett, Jan. 30, 1998, 422(2):259-264.

Murata et al., "Anti-Digoxin Fab Variants Generated by Phage Display," Mol Biotechnol, Jun. 2013, 54(2):269-277. doi : 10.1007/s12033-012-9564-1.

Murray et al., Chapter 55 "Blood plasma and coagulation process," Human Biochemistry (Biokhimia tsheloveka), Moscow, Mir Binton, 2009, 2:328-329 (with English translation).

Muto et al., "Anti-factor IXa/X bispecific antibody (ACE910): hemostatic potency against ongoing bleeds in a hemophilia A model and the possibility of routine supplementation," J Thromb Haemost, Feb. 2014, 12(2):206-213. doi: 10. 1111/jth.12474.

Muto et al., "Hemostatic Effect of a Novel Bispecific Antibody (ACE910) Against Activated Factor IX and Factor X in an Acquired Hemophilia A Model," Blood, 2012, vol. 120, No. 21, p. 42.

Muto et al., "Preventive effect of a bispecific antibody ACE910 that mimics the function of factor VIII on joint bleeding in a model of hemophilia A," The proceedings of the 36th Congress of the Japanese Society on Thrombosis and Hemostasis, May 16, 2014 (1 page) (with English translation, 1 page).

Muto et al., "Preventive effect of a bispecific antibody ACE910 that mimics the function of factor VIII on joint bleeding in a model of hemophilia A," The 36th Congress of the Japanese Society on Thrombosis and Hemostasis, May 30, 2014, pp. 1-14 (with English abstract).

Muto et al., "Preventive effect of a humanized bispecific antibody to factors IXa and X (ACE910) on spontaneous joint bleeding in a non-human primate model of hemophilia A," Haemophilia, 2014, 20 (Suppl. 3), p. 76.

Muto et al., "Preventive effect of a humanized bispecific antibody to factors IXa and X (ACE910) on spontaneous joint bleeding in a non-human primate model of hemophilia A," Meeting World Federation of Hemophilia, 2014 World Congress, May 14, 2014.

Muto et al., "Preventive Effect of Bispecific Antibody ACE910 that functionally substitutes for Factor VIII on Intraarticular Bleeding in Hemophilia A Models," Japanese Journal of Thrombosis and Hemostasis, 2014, vol. 25, No. 2:244 (0-016) (with English translation).

Narhi et al., "Asn to Lys mutations at three sites which are N-glycosylated in the mammalian protein decrease the aggregation of *Escherichia coli*-derived erythropoietin," Protein Eng, Feb. 2001, 14(2):135-140.

Nesterova et al., "Glypican-3 as a novel target for an antibody-drug conjugate," AACR Abstract No. 656, Los Angeles, CA, Apr. 4-18, 2007.

Nieba et al., "Disrupting the hydrophobic patches at the antibody variable/constant domain interface: improved in vivo folding and physical characterization of an engineered scFv fragment," Protein Eng, Apr. 1997, 10(4):435-444.

Nilsson et al., "Induction of split tolerance and clinical cure in high-responding hemophiliacs with factor IX antibodies," Proc Natl Acad Sci USA, Dec. 1986, 83:9169-9173.

Nilsson et al., "Twenty-five years' experience of prophylactic treatment in severe haemophilia A and B," J Intern Med, Jul. 1992, 232:25-32.

Nishimoto et al., "Humanized anti-interleukin-6 receptor antibody treatment of multicentric Castleman disease," Blood, Oct. 15, 2005, 106:2627-2632.

Nishimoto et al., "Interleukin 6: from bench to bedside," Nat Clin Pract Rheumatol, Nov. 2006, 2:619-626.

Nishimura et al., "Factor IX Fukuoka—Substitution of ASN92 by his in the second epidermal growth factor-like domain results in defective interaction with factors VIIIa/X," Journal of Biological Chemistry, Nov. 15, 1993, 268(32):24041-24046.

Nitta et al., "Preliminary trial of specific targeting therapy against malignant glioma," Lancet, Feb. 1990, 335:368-371.

Nogami, "Bispecific Antibody that Substitutes for Factor VIII in the Treatment of Childhood Hemophilia A," The Japanese Journal of Pediatric Hematology/Oncology, 2016, 53(2):69-74 (with English translation).

Nohaile et al., "Altering dimerization specificity by changes in surface electrostatics," Proc Natl Acad Sci USA, Mar. 13, 2001, 98(6):3109-3114. Epub Feb. 27, 2001.

O'Shea et al., "Peptide 'Velcro': design of a heterodimeric coiled coil," Curr Biol, Oct. 1, 1993, 3(10):658-667.

Okubo et al. "The production and characterization of four monoclonal antibodies to human factor X," Nara Med Assoc, 1987, 38(1):20-28.

Oldenburg et al., "Emicizumab Prophylaxis in Hemophilia A with Inhibitors," The New England Journal of Medicine, Aug. 2017, 377(9):809-818. doi: 10.1056/NEJMoa1703068. Epub Jul. 10, 2017.

Oldenburg, "Prophylaxis in bleeding disorders," Thromb Res, Jan. 2011, 127 Suppl 1 :S14-S17. doi: 10.1016/j.thromres.2010.10.005. Epub Nov. 26, 2010.

Onda et al., "Lowering the Isoelectric Point of the Fv Portion of Recombinant Immunotoxins Leads to Decreased Nonspecific Animal Toxicity without Affecting Antitumor Activity," Cancer Res, Jul. 2001, 61:5070-5077.

Ono et al., "The humanized anti-HM1.24 antibody effectively kills multiple myeloma cells by human effector cell-mediated cytotoxicity," Mol Immunol, Apr. 1999, 36(6):387-395.

Otomo et al., "Structure of the heterodimeric complex between CAD domains of CAD and ICAD," Nat Struct Biol, Aug. 2000, 7(8):658-662. doi: 10.1038/77957. PMID: 10932250.

Ozhegov et al., Tolkovyi Slovar Russkogo iazyka, 2004, p. 292 (with an English translation of the relevant passage defining "Control").

(56) References Cited

OTHER PUBLICATIONS

Pabst et al., "Engineering of novel Staphylococcal Protein A ligands to enable milder elution pH and high dynamic binding capacity," J Chromatogr A, Oct. 3, 2014, 1362:180-185. doi: 10.1016/j.chroma.2014.08.046.Epub Aug. 19, 2014.
Pabst et al., "Evaluation of recent Protein A stationary phase innovations for capture of biotherapeutics," J Chromatogr A, Jun. 15, 2018, 1554:45-60. doi: 10.1016/j.chroma.2018.03.060. Epub Apr. 7, 2018.
Pakula et al., "Genetic Analysis of Protein Stability and Function," Annu Rev Genet, 1989, 23:289-310.
Pan et al., "Blocking neuropilin-1 function has an additive effect with anti-VEGF to inhibit tumor growth," Cancer Cell, Jan. 2007, 11(1):53-67.
Panka et al., "Variable region framework differences result in decreased or increased affinity of variant anti-digoxin antibodies," Proc Natl Acad Sci USA, May 1988, 85(9):3080-3084.
Pardridge et al., "Enhanced cellular uptake and in vivo biodistribution of a monoclonal antibody following cationization," J Pharm Sci, Aug. 1995, 84(8):943-948.
Pardridge et al., "Enhanced endocytosis in cultured human breast carcinoma cells and in vivo biodistribution in rats of a humanized monoclonal antibody after cationization of the protein," J Pharmacol Exp Ther, Jul. 1998, 286(1):548-554.
Paul, Chapter 8 "Immunogenicity and Antigen Structure," Fundamental Immunology, 3rd edition, Raven Press NY, 1993, p. 242.
Pavlinkova et al., "Charge-modified single chain antibody constructs of monoclonal antibody CC49: Generation, characterization, pharmacokinetics, and biodistribution analysis," Nucl Med Biol, Jan. 1999, 26:27-34.
Pavlou et al., "The therapeutic antibodies market to 2008," Eur J Pharm Biopharm, Apr. 2005, 59:389-396.
Peipp et al., "Bispecific antibodies targeting cancer cells," Biochem Soc Trans, Aug. 2002, 30:507-511.
Pejchal et al., "A Conformational Switch in Human Immunodeficiency Virus gp41 Revealed by the Structures of Overlapping Epitopes Recognized by Neutralizing Antibodies," J Virol, Sep. 2009, 83(17): 8451-8462. doi: 10.1128/JVI.00685-09. Epub Jun. 10, 2009.
Peters et al., "Engineering an improved IgG4 molecule with reduced disulfide bond heterogeneity and increased Fab domain thermal stability," J Biol Chem, Jul. 13, 2012, 287(29):24525-24533. doi: 10.1074/jbc.M112.369744. Epub May 18, 2012.
Piper et al., "Interferon therapy in primary care," Primary Care Update for Ob/Gyns, Jul. 2001, 8(4):163-169.
Poduslo et al., "Polyamine modification increases the permeability of proteins at the blood—nerve and blood-brain barriers," J Neurochem, Apr. 1996, 66:1599-1609.
Pokkuluri et al., "A domain flip as a result of a single amino-acid substitution," Structure, Aug. 15, 1998, 6(8):1067-1073.
Pons et al., "Energetic analysis of an antigen/antibody interface: alanine scanning mutagenesis and double mutant cycles on the HyHEL-10/lysozyme interaction," Protein Sci, May 1999, 8(5):958-968.
Portolano et al., "Lack of Promiscuity in Autoantigen-Specific H and L Chain Combinations as Revealed by Human H and L Chain 'Roulette'," J Immunol, Feb. 1, 1993, 150(3):880-887.
Presta, "Engineering of therapeutic antibodies to minimize immunogenicity and optimize function," Adv Drug Deliv Rev, Aug. 7, 2006, 58(5-6):640-656.
Price et al., "Tissue factor and tissue factor pathway inhibitor," Anaesthesia, May 2004, 59:483-492.
Queen et al., "A humanized antibody that binds to the interleukin 2 receptor," Proc Natl Acad Sci USA, Dec. 1989, 86(24):10029-10033.
Raffen et al., "Reengineering immunoglobulin domain interactions by introduction of charged residues," Protein Eng, Apr. 1998, 11:303-309.
Raghavan et al., "Fc Receptors and Their Interactions with Immunoglobulins," Annu Rev Cell Dev Biol, Nov. 1996, 12:181-220.
Rajpal et al., "A general method for greatly improving the affinity of antibodies by using combinatorial libraries," Proc Natl Acad Sci USA, Jun. 14, 2005, 102:8466-8471.
Raposo et al., "Epitope-specific antibody response is controlled by immunoglobulin Vh polymorphisms," J Exp Med, Mar. 10, 2014, 211(3):405-411. doi: 10.1084/jem.20130968. Epub Feb. 17, 2014.
Reddy et al., "Elimination of Fc receptor-dependent effector functions of a modified IgG4 monoclonal antibody to human CD4," J Immunol, Feb. 15, 2000, 164(4):1925-1933.
Reference table: IMGT exon, EU and Kabat numbering of residues within the human IgG1 sequence; retrieved from http://www.imgt.org/IMGTScientificChart/Numbering/HuIGHGnber.html on Jun. 1, 2020, 4 pages (document submitted by the opponents in the opposition proceedings of corresponding EP 3 050 963, which was notified to the patentee on Jul. 3, 2020).
Reichert et al., "Development trends for monoclonal antibody cancer therapeutics," Nat Rev Drug Discov, May 2007, 6(5):349-356.
Reichert et al., "Monoclonal antibody successes in the clinic," Nat Biotechnol, Sep. 2005, 23:1073-1078.
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997, 13(11):933-943.
Retout et al., "Population Pharmacokinetic Analysis and Exploratory Exposure-Bleeding Rate Relationship of Emicizumab in Adult and Pediatric Persons with Hemophilia A," Clin Pharmacokinet, Dec. 2020, 59(12):1611-1625. Published online Jun. 5, 2020.
Ridgway et al., "'Knobs-into-holes' engineering of antibody $C_H3$ domains for heavy chain heterodimerization," Protein Eng, Jul. 1996, 9:617-621.
Rispens et al., "Mechanism of Immunoglobulin G4 Fab-arm Exchange," J Am Chem Soc, Jul. 6, 2011, 133(26):10302-10311. doi: 10.1021/ja203638y. Epub Jun. 15, 2011.
Rispens et al., "Dynamics of inter-heavy chain interactions in human immunoglobulin G (IgG) subclasses studied by kinetic Fab arm exchange," J Biol Chem, Feb. 28, 2014, 289(9):6098-6109. doi: 10.1074/jbc.M113.541813. Epub Jan. 14, 2014.
Roguska et al., "Humanization of murine monoclonal antibodies through variable domain resurfacing," Proc Natl Acad Sci USA, Feb. 1, 1994, 91:969-973.
Roitt et al., Immunology, M., Mir, 5th Edition, 2000, pp. 97-113 (with what are believed to be the corresponding pages from an English language edition of Immunology).
Roitt et al., "Antibodies and their Receptors," Immunology, 5th edition, 1998, p. 80-81.
Roopenian et al., "FcRn: the neonatal Fc receptor comes of age," Nat Rev Immunol, Sep. 2007, 7(9):715-725.
Rothe et al., "Ribosome display for improved biotherapeutic molecules," Expert Opin Biol Ther, Feb. 2006, 6:177-187.
Rudikoff et al., "Single amino acid substitution altering antigen-binding specificity," Proc Natl Acad Sci USA, Mar. 1982, 79(6):1979-1983.
Ruef et al., "A bispecific antifibrin-antiplatelet urokinase conjugate (BAAUC) induces enhanced clot lysis and inhibits platelet aggregation," Thromb Haemost, Jul. 1999, 82(1):109-114.
Ruf et al., "Pharmacokinetics and in vivo stability of intraperitoneally administered therapeutic antibody catumaxomab," J Clin Oncol, 2008, 26(May 20 suppl), abstr 14006.
Ruggeri et al., "von Willebrand Factor and van Willebrand Disease," Blood, Oct. 1987, 70(4):895-904.
Ryman et al., "Pharmacokinetics of Monoclonal Antibodies," CPT Pharmacometrics Syst Pharmacol, Sep. 2017, 6(9):576-588. doi: 10.1002/psp4.12224. Epub Jul. 29, 2017.
Saenko et al., "Molecular defects in coagulation Factor VIII and their impact on Factor VIII function," Vox Sang, Aug. 2002, 83(2):89-96.
Saito et al., "Establishment of Factor VIII Mimetic Antibodies and Their In Vitro Activities in Hemophilia A," 2006 National Hemophilia Foundation Symposia, 1 page.
Saito et al., "Factor VIII Mimetic Antibody: (1) Establishment and Characterization of Anti-factor IX/anti-factor X Bispecific Antibod-

(56) References Cited

OTHER PUBLICATIONS ies," 2005 International Society of Thrombosis and Haemostasis, vol. 3, Issue Supplement s1, p. OR160.

Sakai et al., "Guidelines for the management of acquired hemophilia A: 2017 revision," Jpn J Thromb Hemost, 2017, 28(6):715-747 (with English translation).

Salfeld et al., "Isotype selection in antibody engineering," Nat Biotechnol, Dec. 2007, 25:1369-1372.

Sal-Man et al., "Arginine mutations within a transmembrane domain of Tar, an *Escherichia coli* aspartate receptor, can drive homodimer dissociation and heterodimer association in vivo," Biochem J, Jan. 1, 2005, 385:29-36.

Sampei et al., "Non-antigen-contacting region of an asymmetric bispecific antibody to factors IXa/X significantly affects factor VIII-mimetic activity," mAbs, Jan./Feb. 2015, 7(1):120-128. doi: 10.4161/19420862.2015.989028.

Sarkar et al., "Rational cytokine design for increased lifetime and enhanced potency using pH-activated 'histidine switching'," Nat Biotechnol, Sep. 2002, 20(9):908-913. Epub Aug. 5, 2002.

Sato et al., "Properties of Two VEGF Receptors, Flt-1 and KDR, in Signal Transduction," Ann NY Acad Sci, May 2000, 902:201-207, discussion 205-207.

Sato et al., "Reshaping a human antibody to inhibit the interleukin 6-dependent tumor cell growth," Cancer Res, Feb. 15, 1993, 53:851-856.

Schaefer et al., "Immunoglobulin domain crossover as a generic approach for the production of bispecific IgG antibodies," Proc Natl Acad Sci USA, Jul. 5, 2011, 108(27):11187-11192. doi: 10.1073/pnas.1019002108. Epub Jun. 20, 2011.

Schaeffer et al., "The Rat Glomerular Filtration Barrier Does Not Show Negative Charge Selectivity," Microcirculation, Oct. 2002, 9:329-342.

Schmidt et al., "Structure-function relationships in factor IX and factor IXa," Trends Cardiovasc Med, Jan. 2003, 13(1):39-45.

Schmidt et al., Chapter 18, Section 18.6 "Hemostasis and Coagulation," Human Physiology, Second Edition, Springer-Verlag, 1989, pp. 418-423.

Schmidt et al., Chapter 29 "Enzymes of the pancreatic juice," Human Physiology, Second Edition, Springer-Verlag, 1989, p. 716.

Schmidt et al., Chapter 18, Section 18.6 "Hemostasis and Coagulation," Human Physiology, Moscow, 1996, v. 2, pp. 431-436 (with English translation).

Schmidt et al., Chapter 29 "Enzymes of the pancreatic juice," Human Physiology, Moscow, 1996, v. 3, p. 764 (with English translation).

Schmitz et al., "Phage display: a molecular tool for the generation of antibodies—a review," Placenta, Mar.-Apr. 2000, 21 Suppl A:S106-S112.

Schuurman et al., "Normal human immunoglobulin G4 is bispecific: it has two different antigen- combining sites," Immunology, Aug. 1999, 97(4):693-698.

Schuurman et al., "The inter-heavy chain disulfide bonds of IgG4 are in equilibrium with intra-chain disulfide bonds," Mol Immunol, Jan. 2001, 38(1):1-8.

Screenshots of Genetyx software, 3 pages (document cited by the opponent during the opposition proceedings of EP 2 202 245 on May 22, 2020).

Screenshots of the web-based calculator, 9 pages (document cited by the opponent during the opposition proceedings of EP 2 202 245 on May 22, 2020).

Sections of the Genetyx manual pertaining to isoelectric point, 5 pages (document cited by the opponent during the opposition proceedings of EP 2 202 245 on May 22, 2020) (with English translation).

Segal et al., "Bispecific antibodies in cancer therapy," Curr Opin Immunol, Oct. 1999, 11:558-562.

Segal et al., "Introduction: bispecific antibodies," J Immunol Methods, Feb. 1, 2001, 248:1-6.

Sequence alignments and modification scheme, 3 pages (document submitted during Oral Proceedings and mentioned in minutes of the Oral Proceedings posted by EPO on Jul. 25, 2018).

Shalaby et al., "Development of Humanized Bispecific Antibodies Reactive with Cytotoxic Lymphocytes and Tumor Cells Overexpressing the HER2 Protooncogene," J Exp Med, Jan. 1, 1992, 175:217-225.

Sharifi et al., "Improving monoclonal antibody pharmacokinetics via chemical modification," Q J Nucl Med, Dec. 1998, 42(4):242-249.

Shaul, "Exploring the charge space of protein-protein association: a proteomic study," Proteins, Aug. 15, 2005, 60:341-352.

Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem, Mar. 2, 2001, 276:6591-6604. Epub Nov. 28, 2000.

Shima, "The Forefront and Prospects of Hemophilia Treatment," The Journal of the Japan Pediatric Society, Mar. 1, 2017, 121(3):543-552 (with English translation).

Shima et al., abstract #691, "Safety and Prophylactic Efficacy Profiles of ACE910, a Humanized Bispecific Antibody Mimicking the FVIII Cofactor Function in Japanese Hemophilia A Patients Both without and with FVIII Inhibitors: First-in-Patient Phase 1 Study," 2014, 56th ASH Annual Meeting and Exposition Abstract & Program [online.2014.12]. URL<https://ash.confex.com/ash/2014/webprogram/Paper67797.html>.

Shima et al., "Pharmacokinetics and Pharmacodynamic Response of Bispecific Antibody ACE910 which Functionally Substitutes for Factor VIII Cofactor, in Healthy Adults," Japanese Journal of Thrombosis and Hemostasis, 2014, vol. 25, No. 2:245 (0-017) (with English translation).

Shima et al., "Safety and Prophylactic Efficacy Profiles of ACE910, a Humanized Bispecific Antibody Mimicking the FVIII Cofactor Function, in Japanese Hemophilia A Patients Both without and with FVIII Inhibitors: First-in-Patient Phase 1 Study," Nov. 6, 2014, https://ash.confex.com/ash/2014/webprogram/Paper67797.html. (with English abstract).

Shima et al., "The pharmacokinetic and pharmacodynamic profiles of ACE910, a bispecific antibody mimicking the FVIII cofactor function, demonstrated in healthy adults," Meeting of The 36th Congress of the Japanese Society on Thrombosis and Hemostasis, May 30, 2014 (with English translation).

Shima et al., "The pharmacokinetic and pharmacodynamic profiles of ACE910, a bispecific antibody mimicking the FVIII cofactor function, demonstrated in healthy adults," Proceedings of The 36th Congress of the Japanese Society on Thrombosis and Hemostasis, May 16, 2014 (with English translation).

Shima et al., "The safety, tolerability, pharmacokinetic and pharmacodynamic profiles of ACE910, a humanized bispecific antibody mimicking the FVIII cofactor function demonstrated in healthy adults," Haemophilia, 2014, 20 (Suppl. 3), p. 76.

Shima et al., "Factor VIII Mimetic Antibody: (2) In Vitro Assessment of Cofactor Activity in Hemophilia A," 2005 International Society of Thrombosis and Haemostasis, vol. 3, Issue Supplement s1, p. #P0038.

Shima et al., "Factor VIII Taitei Kotai (2), Ketsuyubyo A Kanja Katsueki ni okeru in vitro Gyoko Kassei no Kento", Rinsho Ketsueki, 2005, 46(8):777 (with English translation).

Shima, "Bi-Specific Antibodies as FVIII Mimetics in Hemophilia," Jun. 10, 2014, https://www.isth.org/page/2014Microsite/?, https://www.isth.org/page/2014FinalProgram? and http://c.ymcdn.com/sites/www.isth.org/resource/resmgr/Microsite/Milwaukee_Final_Program_6614.pdf.

Shima, "Bi-Specific Antibodies as FVIII Mimetics in Hemophilia," Meeting ISTH 2014 SSC, Jun. 25, 2014.

Shima, "New hemophilia treatment by a bispecific antibody to factors IXa and X," The 76th Annual Meeting of the Japanese Society of Hematology, Nov. 1, 2014 (with English translation).

Shima, "New hemophilia treatment by a bispecific antibody to factors IXa and X," Proceedings of The 76th Annual Meeting of the Japanese Society of Hematology, abstract SY9-2, Oct. 23, 2014.

(56) References Cited

OTHER PUBLICATIONS

Shima, "New hemophilia treatment by a bispecific antibody to factors IXa and X," Oct. 24, 2014, http://www2.convention.co.jp/76jsh, http://www2.convention.co.jp/76jsh/japanese/schedule.html, https://www.meeting-schedule.com/jsh76/schedule.html and https://www.meeting-schedule.com/jsh76/abstract.html (with English abstract).
Shima, "New hemophilia treatment by a bispecific antibody to factors IXa and X," The Japanese Journal of Clinical Hematology, 2014, vol. 55, No. 9:236.
Shima, "Novel Bypassing Agents-novel bypass and adjunctive therapies," Meeting World Federation of Hemophilia, 2014 World Congress, May 15, 2014.
Shima, "Progress in Pathological Analysis of Hemophilia A," Japanese Journal of Thrombosis and Hemostasis, 2015, vol. 25, No. 2:144 (with English translation).
Shima, "Progress in the Pathological Analysis of Hemophilia A," Proceedings of The 36th Congress of the Japanese Society on Thrombosis and Hemostasis, May 16, 2014 (with English translation).
Shima, "Progress in the Pathological Analysis of Hemophilia A," Meeting of the 36th Congress of the Japanese Society on Thrombosis and Hemostasis, May 31, 2014 (with English translation).
Shima, "The safety, tolerability, pharmacokinetic and pharmacodynamic profiles of ACE910 a humanized bispecific antibody mimicking the FVIII cofactor function demonstrated in bealthy adults," Meeting World Federation of Hemophilia 2014, World Congress, May 14, 2014.
Shima et al., "Long-term safety and efficacy of emicizumab in a phase 1/2 study in patients with hemophilia A with or without inhibitors," Blood Adv, Sep. 27, 2017, 1(22):1891-1899. doi: 10.1182/bloodadvances.2017006684. eCollection Oct. 10, 2017.
Shima et al., "Long-term safety and prophylactic efficacy of once weekly subcutaneous administration of ACE910, in Japanese hemophilia A patients with and without FVIII inhibitors: interim results of the extension study of a phase 1 study," J Thromb Haemost, Jun. 2015, 13 Suppl 2:6-7, (Abstr AS017).
Shima, How to treat patients with severe haemophilia A without FVIII concentrates? New concepts in haemophilia therapy (bispecific antibody mimicking VIII), Haemophilia, 2015, 21 (Suppl. 2), 7-8.
Shima, "Bispecific antibodies to coagulation factors IXa and X mimic the function of factor VIII," 2006 World Federation of Haemophilia, Haemophilia, 2006, 12(Suppl. 2):98.
Shima et al., "Factor VIII-Mimetic Function of Humanized Bispecific Antibody in Hemophilia A," The New England Journal of Medicine, May 26, 2016, 374(21):2044-2053. doi: 10.1056/NEJMoa1511769.
Shirahata, "5. Future Prospects 1) Direction for Improvement of Coagulation Factor Preparations," Iyaku (Medicine and Drug) Journal Co., Ltd., 2009, pp. 280-289 (with English translation).
Shire et al., "Challenges in the development of high protein concentration formulations," J Pharm Sci, Jun. 2004, 93:1390-1402.
Singer et al., Chapter 1.3 "Structure of Proteins," Genes & Genomes, 1991, p. 59-71.
Singer et al., Chapter 1.3 "Structure of Proteins," Genes & Genomes, Moscow, Mir, 1998, pp. 63-64 (with what are believed to be the corresponding p. from an English version of Genes & Genomes).
Singer et al., Chapter 1.3 "Structure of Proteins," Genes & Genomes, 1991, pp. 67-70.
Sinha et al., "Electrostatics in protein binding and function," Curr Protein Pept Sci, Dec. 2002, 3(6):601-614.
Sinha et al., "Molecular dynamics simulation of a high-affinity antibody-protein complex: the binding site is a mosaic of locally flexible and preorganized rigid regions," Cell Biochem Biophys, Oct. 2005, 43:253-273.
Skerra, "Use of the tetracycline promoter for the tightly regulated production of a murine antibody fragment in Escherichia coli," Gene, Dec. 30, 1994, 151(1-2):131-135.
Smans et al., "Bispecific antibody-mediated lysis of primary cultures of ovarian carcinoma cells using multiple target antigens," Int J Cancer, Nov. 10, 1999, 83:270-277.

Smith, "Creative Expression: Mammalian Expression Vectors and Systems," The Scientist Magazine, Feb. 2, 1998, pp. 1-3.
Soeda et al., "Factor VIII Taitei Kotai (1) Ko FIXa/FX bispecific Kotai No. Sakusei oyobi characterization," Rinsho Ketsueki, Aug. 30, 2005, 46(8):728 (with English translation).
Soeda et al., "FVIII-Mimetic Action of Anti-FIXa/Anti-FX Bispecific Antibodies Produced by the Phage Library Method" Jpn J Thromb Hemost, Oct. 1, 2005, 16(5):526 (with English translation).
Spiess et al., "Bispecific antibodies with natural architecture produced by co-culture of bacteria expressing two distinct half-antibodies," Nat Biotechnol, Aug. 2013, 31(8):753-758. doi: 10.1038/nbt.2621. Epub Jul. 7, 2013.
Stancovski et al., "Mechanistic Aspects of the Opposing Effects of Monoclonal Antibodies to the ERBB2 Receptor on Tumor Growth," Proc Nat Acad Sci USA, Oct. 1, 1991, 88:8691-8695.
Staerz et al., "Hybrid hybridoma producing a bispecific monoclonal antibody that can focus effector T-cell activity," Proc Natl Acad Sci USA, Mar. 1986, 83:1453-1457.
Stickney et al., "Bifunctional Antibody: A Binary Radiopharmaceutical Delivery System for Imaging Colorectal Carcinoma," Cancer Res, Dec. 15, 1991, 51:6650-6655.
Strand et al., "Biologic therapies in rheumatology: lessons learned, future directions," Nat Rev Drug Discov, Jan. 2007, 6:75-92.
Summary of information about antibodies in Examples of patent, 3 pages (document submitted in EP opposition and posted by EPO on Apr. 13, 2018).
Sun et al., "Coexpression of Gas6/Axl in human ovarian cancers," Oncology, 2004, 66(6):450-457.
Supplemental Material to Raposo et al., "Epitope-specific antibody response is controlled by immunoglobulin VH polymorphisms," J Exp Med, Mar. 10, 2014, 211(3):405-11. doi: 10.1084/jem.20130968. Epub Feb. 17, 2014 (submitted by the patentee during opposition proceedings of EP 2 202 245 on May 24, 2019), 4 pages.
Suresh et al., "Advantages of bispecific hybridomas in one-step immunocytochemistry and immunoassays," Proc Natl Acad Sci USA, Oct. 1986, 83:7989-7993.
Suresh et al., "Bispecific monoclonal antibodies from hybrid hybridomas," Methods Enzymol, 1986, 121:210-228.
Tabrizi et al., "Elimination mechanisms of therapeutic monoclonal antibodies," Drug Discov Today, Jan. 2006, 11(1-2):81-88.
Takeyama et al., "An anti-factor IXa/factor X bispecific antibody, emicizumab, improves ex vivo coagulant potentials in plasma from patients with acquired hemophilia A," J Thromb Haemost, Apr. 2020, 18(4):825-833.
Taki, The Journal of Japanese Society on Thrombosis and Hemostasis, 2002, 13:109-113.
Tamura et al., "Structural correlates of an anticarcinoma antibody: identification of specificity-determining residues (SDRs) and development of a minimally immunogenic antibody variant by retention of SDRs only," J Immunol, Feb. 1, 2000, 164(3):1432-1441.
Tan et al., "Contributions of a highly conserved VH/VL hydrogen bonding interaction to scFv folding stability and refolding efficiency," Biophys J, Sep. 1998, 75(3):1473-1482.
Tan et al., "Engineering the isoelectric point of a renal cell carcinoma targeting antibody greatly enhances scFv solubility," Immunotechnology, Oct. 1998, 4(2):107-114.
Tarantino et al., "Safety of human plasma-derived clotting factor products and their role in haemostasis in patients with haemophilia: meeting report," Haemophilia, Sep. 2007, 13(5):663-669.
Tarditi et al., "Selective high-performance liquid chromatographic purification of bispecific monoclonal antibodies," J Chromatogr, May 22, 1992, 599:13-20.
Taylor et al., "A new era for hemophilia B treatment," Blood, Apr. 7, 2016, 127(14):1734-1736.
Teeling et al., "The biological activity of human CD20 monoclonal antibodies is linked to unique epitopes on CD20," J Immunol, Jul. 1, 2006, 177(1):362-371.
Ten Kate et al., "Effect of isoelectric point on biodistribution and inflammation: imaging with indium-111-labelled IgG," Eur J Nucl Med, Jun. 1990, 17:305-309.
Tsurushita et al., "Design of humanized antibodies: From anti-Tac to Zenapax," Methods, May 2005, 36:69-83.

(56) References Cited

OTHER PUBLICATIONS

Uchida et al., "A first-in-human phase 1 study of ACE910, a novel factor VIII-mimetic bispecific antibody, in healthy subjects," Blood, 2016 Mar. 2016, 127(13):1633-1641. doi: 10.1182/blood-2015-06-650226. Epub Dec. 1, 2015.
Uchida et al., "First-In-Human Trial of Bispecific Antibody ACE910 Having Factor VIII-Substituting Activity, Safety, Pharmacokinetics, and Pharmacodynamics in Healthy Adults," Jpn J Clin Pharmacol Ther, 2014, 45 Suppl:S297 (with English translation).
Vaisitti et al., "Cationization of monoclonal antibodies: another step towards the 'magic bullet'?," J Biol Regul Homeost Agents, Jul.-Dec. 2005, 19(3-4):105-112.
Vajdos et al., "Comprehensive functional maps of the antigen-binding site of an anti-ErbB2 antibody obtained with shotgun scanning mutagenesis," J Mol Biol, Jul. 5, 2002, 320(2):415-428.
Van Den Abbeele et al., "Antigen-Binding Site Protection During Radiolabeling Leads to a Higher Immunoreactive Fraction," J Nucl Med, Jan. 1991, 32(1):116-122.
Van Der Neut Kolfschoten et al., "Anti-inflammatory activity of human IgG4 antibodies by dynamic Fab arm exchange," Science, Sep. 14, 2007, 317(5844):1554-1557.
Van Walle et al., "Immunogenicity screening in protein drug development," Expert Opin Biol Ther, Mar. 2007, 7(3):405-418.
Van Loghem et al., "Staphylococcal protein A and human IgG subclasses and allotypes," Scand J Immunol, Mar. 1982, 15(3):275-278.
Vargas-Madrazo et al., "An improved model of association for VH-VL immunoglobulin domains: asymmetries between VH and VL in the packing of some interface residues," J Mol Recognit, May-Jun. 2003, 16(3):113-120.
Vaughan et al., "Human antibodies with sub-nanomolar affinities isolated from a large non-immunized phage display library," Nat Biotechnol, Mar. 1996, 14(3):309-314.
Verbruggen et al., "The Nijmegen Modification of the Bethesda Assay for Factor VIII: C Inhibitors: Improved Specificity and Reliability," Thromb Haemost, Feb. 1995, 73(2):247-251.
Verhoeyen et al., "Construction of a reshaped HMFG1 antibody and comparison of its fine specificity with that of the parent mouse antibody," Immunology, Mar. 1993, 78(3):364-370.
Verhoeyen et al., "Monoclonal Antibodies in Clinical Oncology," 1991, Edited by AA Epenetos, Chapter 5, pp. 37-43, Chapman and Hall.
Wagenvoord et al., "Development of a Simple Chromogenic Factor VIII Assay for Clinical Use," Haemostasis, 1989, 19(4):196-204.
Wang et al., "Conserved amino acid networks involved in antibody variable domain interactions," Proteins, Jul. 2009, 76(1):99-114. doi: 10.1002/prot.22319.
Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," Biochemistry, Jun. 30, 1987, 26(13):4131-4138.
Warnaar et al., "Purification of bispecific F(ab')2 from murine trinoma OC/TR with specificity for CD3 and ovarian cancer," Hybridoma, Dec. 1994, 13:519-526.
Weiner et al., "A Human Tumor Xenograft Model of Therapy with a Bispecific Monoclonal Antibody Targeting c-erbB-2 and CD16," Cancer Res, Jan. 1, 1993, 53:94-100.
Weiner et al., "The Role of T Cell Activation in Anti-CD3 x Antitumor Bispecific Antibody Therapy," J Immunol, Mar. 1, 1994, 152:2385-2392.
Wenig et al., "Structure of the streptococcal endopeptidase IdeS, a cysteine proteinase with strict specificity for IgG," Proc Natl Acad Sci, Dec. 14, 2004, 101:17371-17376.
Wiens et al., "Mutation of a single conserved residue in VH complementarity-determining region 2 results in a severe Ig secretion defect," J Immunol, Aug. 15, 2001, 167(4):2179-2186.
Wiens et al., "Somatic mutation in VH complementarity-determining region 2 and framework region 2: differential effects on antigen binding and Ig secretion," J Immunol, Aug. 1, 1997, 159(3):1293-1302.
Worn et al., "Stability engineering of antibody single-chain Fv fragments," J Mol Biol, Feb. 2, 2001, 305(5):989-1010.
Written Submissions by Opponent 1 (Alexion Pharmaceuticals, Inc.) in Opposition of EP 2 006 381, dated Apr. 13, 2018, 19 pages.
Written Submissions by Opponent 2 (Novo Nordisk A/S) in Opposition of EP 2 006 381, dated Apr. 13, 2018, 14 pages.
Written Submissions by Opponent 3 (name Unknown) in Opposition of EP 2 006 381, dated Apr. 13, 2018, 16 pages.
Wu et al., "Humanization of a Murine Monoclonal Antibody by Simultaneous Optimization of Framework and CDR Residues," J Mol Biol, Nov. 19, 1999, 294(1):151-162.
Wu et al., "Development of motavizumab, an ultra-potent antibody for the prevention of respiratory syncytial virus infection in the upper and lower respiratory tract," J Mol Biol, May 4, 2007, 368:652-665.
Wu et al., "Multimerization of a chimeric anti-CD20 single-chain Fv-Fc fusion protein is mediated through variable domain exchange," Protein Eng, Dec. 2001, 14(12):1025-1033.
Wu et al., "Ultra-potent Antibodies Against Respiratory Syncytial Virus: Effects of Binding Kinetics and Binding Valence on Viral Neutralization," J Mol Biol, Jul. 1, 2005, 350(1):126-144.
Xiang et al., "Production of Murine V-Human Crl Chimeric Anti-TAG72 Antibody Using V Region cDNA Amplified by PCR," Mol Immunol, Aug. 1990, 27:809-817.
Xiang et al., "Study of B72.3 combining sites by molecular modeling and site-directed mutagenesis," Protein Eng, May 2000, 13(5):339-344.
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J Pharmacol Exp Ther, May 2002, 301:467-477.
Yang et al., "CDR Walking Mutagenesis for the Affinity Maturation of a Potent Human Anti-HIV-1 Antibody into the Picomolar Range," J Mol Biol, Dec. 1995, 254(3):392-403.
Yang et al., "Tailoring structure-function and pharmacokinetic properties of single-chain Fv proteins by site-specific PEGylation," Protein Eng, Oct. 2003, 16:761-770.
Yarilin, Fundamentals of Immunology, Moscow, Medicina, 1999, p. 171 (with English translation).
Yasukawa et al., "Structure and expression of human B cell stimulatory factor-2 (BSF-2/IL-6) gene," EMBO J, Oct. 1987, 6(10):2939-2945.
Yoneyama et al., "A Pharmacometric Approach to Substitute for a Conventional Dose-Finding Study in Rare Diseases: Example of Phase III Dose Selection for Emicizumab in Hemophilia A," Clin Pharmacokinet, Sep. 2018, 57(9):1123-1134. doi: 10.1007/s40262-017-0616-3.
Yoneyama et al., "Repeated Time-to-Event Modeling to Characterize the Bleeding-Prophylactic Efficacy of ACE910, A Bispecific Antibody to Factors IXA and X, in Patients with Hemophilia A," Clin Pharmacol Ther, Feb. 2016, 99(Suppl 1):S33.
Young et al., "Efficacy, Safety and Pharmacokinetics (PK) of Once-weekly Prophylactic (Px) Emicizumab (ACE910) in Pediatric (< 12 years) Persons with Hemophilia A with Inhibitors (PwHAwI): Interim Analysis of Single-arm, Multicenter, Open-label, Phase 3 Study (HAVEN 2)," Res Pract Thromb Haemost, 2017, 1(Suppl 2):5.
Zhu et al., "Remodeling domain interfaces to enhance heterodimer formation," Protein Sci, Apr. 1997, 6(4):781-788.
Zuckier et al., "Chimeric human-mouse IgG antibodies with shuffled constant region exons demonstrate that multiple domains contribute to in vivo half-life," Cancer Res, Sep. 1998, 58:3905-3908.
Zuo et al., "An efficient route to the production of an IgG-like bispecific antibody," Protein Eng, May 2000, 13(5):361-367.
Zwick et al., "The long third complementarity-determining region of the heavy chain is important in the activity of the broadly neutralizing anti-human immunodeficiency virus type 1 antibody 2F5," J Virol, Mar. 2004, 78(6):3155-3161.

(56) References Cited

OTHER PUBLICATIONS

USPTO Non-Final Office Action in U.S. App. Ser. No. 11/910,128, dated Nov. 28, 2016, 17 pages.
Chugai Seiyaku Kabushiki Kaisha's letter dated Jun. 12, 2013, regarding oral proceedings scheduled on Jun. 26, 2013, in App. Ser. No. EP 06 73 0769.4-1412 (Annex A submitted with patentee's letter dated Jun. 12, 2013).
Fay et al., "The size of human factor VIII heterodimers and the effects produced by thrombin," Biochim Biophys Acta, Jun. 23, 1986, 871(3):268-278.
Glatter, "Evaluation of Small-Angle Scattering Data from Lamellar and Cylindrical Particles by the Indirect Transformation Method," J Appl Cryst, 1980, 13:577-584.
Hoyer, "The Factor VIII Complex: Structure and Function," Blood, Jul. 1981, 58(1):1-13.
Kitazawa et al., "A bispecific antibody to factors IXa and X restores factor VIII hemostatic activity in a hemophilia A Model," Nat Med, Oct. 2012, 18(10):1570-1574.
Muto et al., "Anti-factor IXa/X bispecific antibody (ACE910): hemostatic potency against ongoing bleeds in a hemophilia A model and the possibility of routine supplementation," J Thromb Haemost, Feb. 2014, 12(2):206-213.
Muto et al., "Anti-factor IXa/X bispecific antibody ACE910 prevents joint bleeds in a long-term primate model of acquired hemophilia A," Blood, Nov. 13, 2014, 124(20):3165-3171. doi: 10.1182/blood-2014-07-585737. Epub Oct. 1, 2014.
Sampei et al., "Identification and Multidimensional Optimization of an Asymmetric Bispecific IgG Antibody Mimicking the Function of Factor VIII Cofactor Activity," PLoS One, 2013, 8(2):e57479, 13 pages. doi: 10.1371/journal.pone.0057479. Epub Feb. 28, 2013.
Tian et al., "In-depth analysis of subclass-specific conformational preferences of IgG antibodies," IUCrJ, Jan. 1, 2015, 2(Pt 1):9-18. doi: 10.1107/S205225251402209X. eCollection Jan. 1, 2015.
Vehar et al., "Structure of human factor VIII," Nature, Nov. 22-28, 1984, 312(5992):337-342.
Wood et al., "Expression of active human factor VIII from recombinant DNA clones," Nature, Nov. 22-28, 1984, 312(5992):330-337.
International Preliminary Report on Patentability for App. Ser. No. PCT/JP2018/040436, dated May 5, 2020, 13 pages (with English translation).
International Search Report for App. Ser. No. PCT/JP2018/040436, dated Dec. 25, 2018, 4 pages (with English translation).
U.S. Pat. No. 8,597,911, Miyazakzi el al., issued Dec. 3, 2013 (abandoned).
U.S. Pat. No. 8,062,635, Hallori el al., issued Nov. 22, 2011.
U.S. Appl. No. 10/575,905, Hallori el al., filed Apr. 30, 2007 (abandoned).
U.S. Pat. No. 10,011,858, Igawa et al., issued Jul. 3, 2018.
U.S. Pat. No. 11,168,344, Igawa et al., issued Nov. 9, 2021.
U.S. Appl. No. 17/520,368, Hallori el al., filed Nov. 5, 2021.
U.S. Appl. No. 13/434,643, Hallori el al., filed Mar. 29, 2012 (abandoned).
U.S. Appl. No. 14/921,590, Hallori el al., filed Oct. 23, 2015 (abandoned).
U.S. Appl. No. 17/389,534, Hattori et al., filed Jul. 30, 2021 (abandoned).
U.S. Appl. No. 17/699,293, Hattori et al., filed Mar. 21, 2022.
U.S. Appl. No. 13/518,861, Igawa et al., filed Oct. 4, 2012.
U.S. Appl. No. 17/485,818, Igawa et al., filed Sep. 27, 2021 (abandoned).
U.S. Appl. No. 17/729,471, Igawa et al., filed Apr. 26, 2022.
U.S. Appl. No. 17/763,948, Yoneyama et al., filed Mar. 25, 2022.
U.S. Pat. No. 10,022,319, Igawa et al., issued Jul. 17, 2018.
U.S. Appl. No. 17/974,914, Hattori et al., filed Oct. 27, 2022.
U.S. Appl. No. 17/821,494, Igawa et al., filed Aug. 23, 2022.
U.S. Appl. No. 17/849,879, Yoneyama, filed Jun. 27, 2022.
U.S. Pat. No. 11,352,438, Yoneyama et al., issued Jun. 7, 2022.
U.S. Appl. No. 17/828,752, Yoneyama et al., filed May 31, 2022.
U.S. Appl. No. 18/081,874, Igawa et al., filed Dec. 15, 2022.

Berry et al., "Substitution of cysteine for selenocysteine in type I iodothyronine deiodinase reduces the catalytic efficiency of the protein but enhances its translation," Endocrinology, Oct. 1992, 131(4):1848-1852.
Gasser et al., "Antibody production with yeasts and filamentous fungi: on the road to large scale?," Biotechnol Lett, Feb. 2007, 29(2):201-212.
Muller et al., "Spliceosomal peptide P140 for immunotherapy of systemic lupus erythematosus: results of an early phase II clinical trial," Arthritis Rheum, Dec. 2008, 58(12):3873-3883.
Goey, "Cascading effects in bioprocessing: the impact of cell culture environment on CHO cell behaviour and host cell protein species," PhD Thesis, Department of Chemical Engineering, Imperial College London, 2016, 279 pages.
"Hemlibra," Assessment report of the European Medicines Agency (EMA), 2018, 126 pages.
U.S. Appl. No. 18/346,920, Hattori el al., filed Jul. 5, 2023.
U.S. Appl. No. 18/176,201, Igawa el al., filed Feb. 28, 2023.
U.S. Appl. No. 18/193,697, Igawa el al., filed Mar. 31, 2023.
U.S. Appl. No. 18/164,709, Yoneyama, filed Feb. 6, 2023.
U.S. Pat. No. 11,649,262, Tanaka el al., issued May 16, 2023.
U.S. Appl. No. 18/472,949, Shima el al., filed Sep. 22, 2023.
U.S. Appl. No. 18/156,559, Yoneyama el al., filed Jan. 19, 2023.
U.S. Appl. No. 18/466,900, Yoneyama el al., filed Sep. 14, 2023.
U.S. Pat. No. 11,612,562, Igawa el al., issued Mar. 28, 2023.
U.S. Appl. No. 18/174,043, Igawa et al., filed Feb. 24, 2023.
U.S. Appl. No. 13/522,848, Igawa et al., filed Oct. 2, 2012.
U.S. Appl. No. 18/156,559, Yoneyama et al., filed Jan. 19, 2023.
U.S. Appl. No. 18/176,201, Igawa et al., filed Feb. 28, 2023.
U.S. Appl. No. 18/193,697, Igawa et al., filed Mar. 31, 2023.
U.S. Appl. No. 18/346,920, Hattori et al., filed Jul. 5, 2023.
U.S. Appl. No. 18/466,900, Yoneyama et al., filed Sep. 14, 2023.
U.S. Appl. No. 18/472,949, SHima et al., filed Sep. 22, 2023.
U.S. Appl. No. 18/479,149, Yoneyama, filed Oct. 2, 2023 (abandoned).
U.S. Appl. No. 18/495,861, Igawa et al., filed Oct. 27, 2023 (abandoned).
U.S. Appl. No. 18/505,180, Igawa et al., filed Nov. 9, 2023 (abandoned).
U.S. Appl. No. 18/425,859, Igawa et al., filed Jan. 29, 2024.
U.S. Appl. No. 18/432,567, Igawa et al., filed Feb. 5, 2024.
U.S. Appl. No. 18/586,698, Hattori et al., filed Feb. 26, 2024.
U.S. Appl. No. 18/734,272, Yoneyama el al., filed Jun. 5, 2024.
U.S. Appl. No. 18/734,434, Yoneyama, filed Jun. 5, 2024.
U.S. Appl. No. 18/737,387, Igawa el al., filed Jun. 7, 2024.
U.S. Appl. No. 18/748,951, Igawa el al., filed Jun. 20, 2024.
U.S. Appl. No. 18/883,787, Igawa el al., filed Sep. 12, 2024.
U.S. Appl. No. 18/479,149, Yoneyama, Oct. 2, 2023.
U.S. Appl. No. 18/495,861, Igawa et al., filed Oct. 27, 2023.
U.S. Appl. No. 18/505,180, Igawa et al., filed Nov. 9, 2023.
U.S. Appl. No. 18/734,272, Yoneyama et al., filed Jun. 5, 2024.
U.S. Appl. No. 18/737,387, Igawa et al., filed Jun. 7, 2024.
U.S. Appl. No. 18/748,951, Igawa et al., filed Jun. 20, 2024.
U.S. Appl. No. 18/883,787, Igawa et al., filed Sep. 12, 2024.
Birch Biotech, "How to Read an HPLC Chromatogram," Aug. 29, 2024, 16 pages, printed from the Internet on Sep. 26, 2024 at https://www.birchbiotech.com/blogs/resources/how-to-read-an-hplc-chromatogram.pdf.
European Medicines Agency, "ICH Topic Q 6 B Specifications: Test Procedures and Acceptance Criteria for Biotechnological/Biological Products, Step 5: Note for Guidance on Specifications," Sep. 1999, 17 pages, printed from the Internet on Sep. 26, 2024 at https://www.ema.europa.eu/en/documents/scientific-guideline/ich-q-6-b-test-procedures-and-acceptance-criteria-biotechnologicalbiological-products-step-5_en.pdf.
"HEMLIBRA® (emicizumab-kxwh) injection, for subcutaneous use," Highlights of Prescribing Information, Genentech, Jan. 2024, 25 pages, printed from the Internet at https://www.gene.com/download/pdf/hemlibra_prescribing.pdf.
Dashivets et al., "Oxidation in the complementarity-determining regions differentially influences the properties of therapeutic antibodies," mAbs, Nov./Dec. 2016, 8(8):1525-1535.

(56) References Cited

OTHER PUBLICATIONS

Su et al., "The role of Antibody $V_\kappa$ Framework 3 region towards Antigen binding: Effects on recombinant production and Protein L binding," Sci Rep, Jun. 19, 2017, 7(1):3766, 7 pages.

* cited by examiner

| Study | Data Group | N | Mean | Std Dev |
|---|---|---|---|---|
| Dissolved Oxygen | Center-Point Runs | 11 | 1.4 | 0.4 |
| | All Runs | 17 | 1.3 | 0.4 |
| Initial pH | Center-Point Runs | 6 | 1.0 | 0.1 |
| | All Runs | 10 | 1.0 | 0.1 |
| Culture Duration without MTX | Center-Point Runs | 3 | 1.1 | 0.0 |
| | All Runs | 7 | 1.1 | 0.0 |

| Data Group | N | Mean | Std Dev |
|---|---|---|---|
| Center-Point Runs | 12 | 1.2 | 0.2 |
| All Runs | 168 | 1.3 | 0.2 |

Abbreviation: MTX = methotrexate; Std Dev = standard deviation;

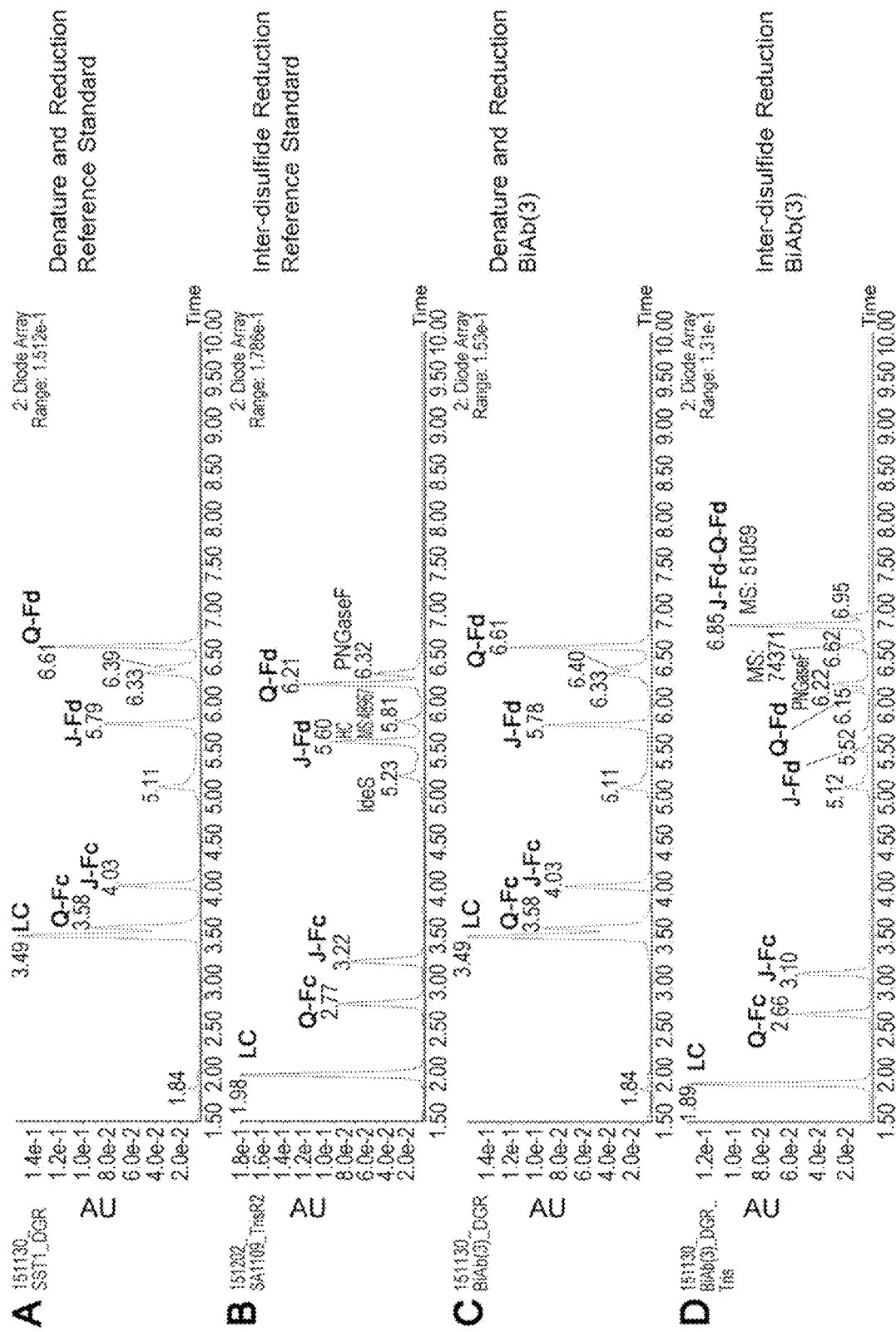
Figs. 3A-D

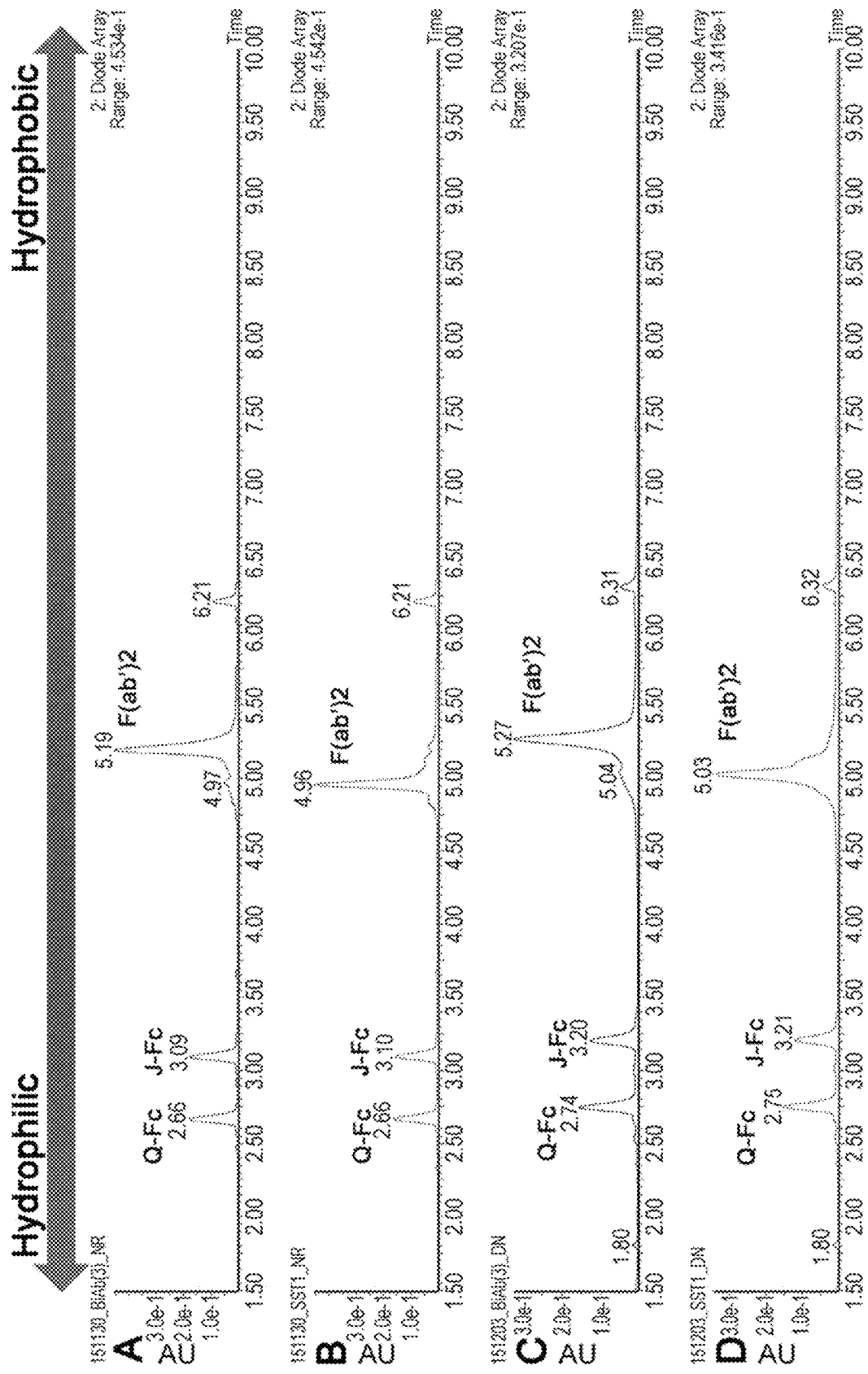
Figs. 4A-D

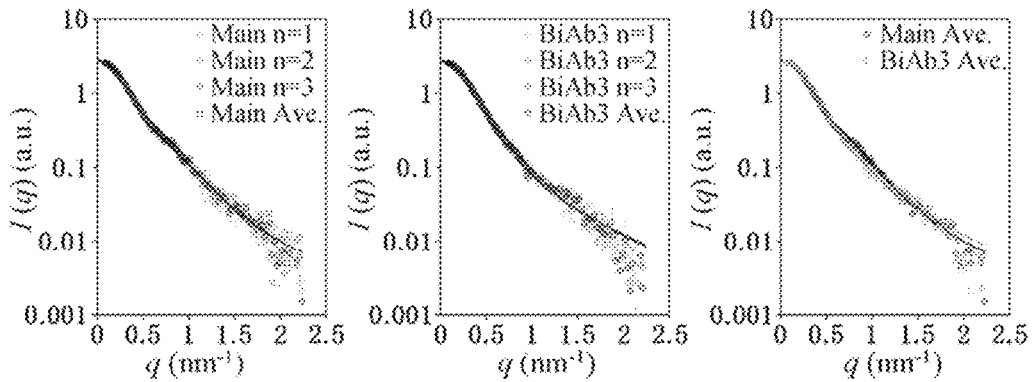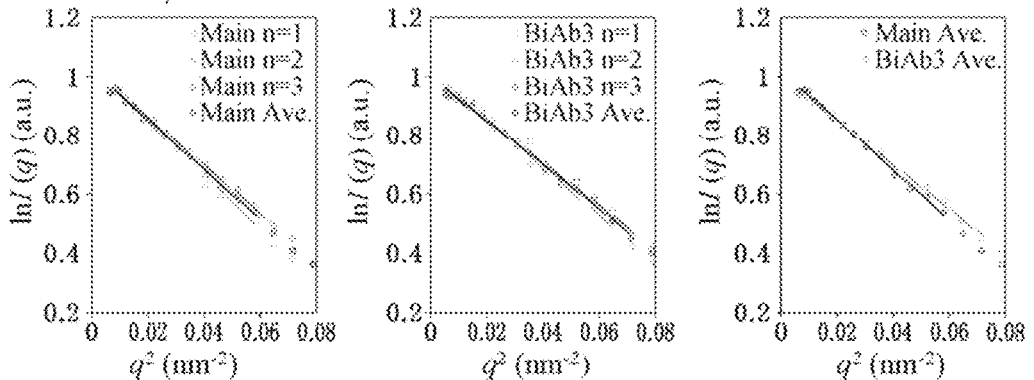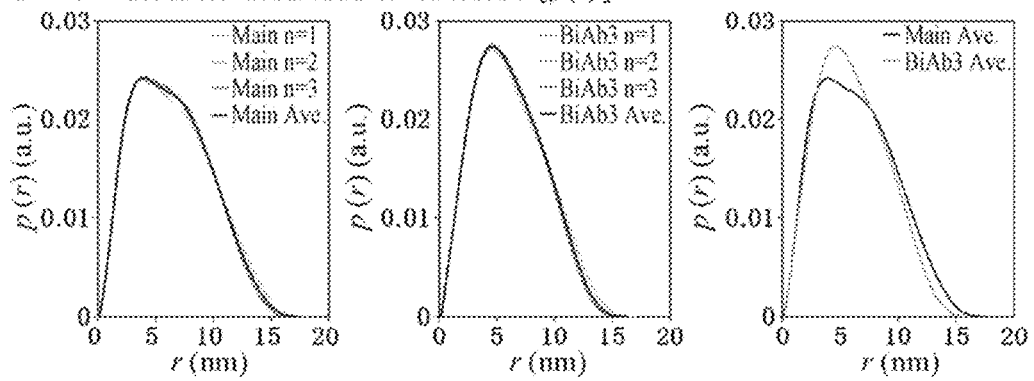
Figs. 8A-D

ANTIBODY VARIANT AND ISOFORM WITH LOWERED BIOLOGICAL ACTIVITY

CROSS-REFERENCE TO RELATED APPLICATIONS

This application is the National Stage of International Application No. PCT/JP2018/040436, filed on Oct. 31, 2018, which claims the benefit of Japanese Application No. 2017-212179, filed on Nov. 1, 2017.

TECHNICAL FIELD

The present invention relates to antibody variants and isoforms with reduced biological activity. For example, the present invention relates to antibody variants and isoforms of Emicizumab, the antibody variants and isoforms having reduced blood coagulation factor VIII (FVIII) mimetic activity. The present invention also relates to pharmaceutical compositions comprising such an antibody variant or isoform at low content rate. The present invention further relates to methods for detecting and methods for analyzing, for the antibody variants and isoforms.

BACKGROUND ART

Antibodies are drawing attention as pharmaceuticals as they are highly stable in plasma and have few adverse effects. Of them, a number of IgG-type antibody pharmaceuticals are available on the market and many antibody pharmaceuticals are currently under development (NPLs 1, 2 and 3).

Hemophilia A is a bleeding abnormality caused by a hereditary decrease or deficiency of FVIII function. Hemophilia A patients are generally administered with an FVIII formulation for bleeding (on-demand administration). In recent years, FVIII formulations are also administered prophylactically to prevent bleeding events (preventive administration; NPLs 1 and 2). The half-life of FVIII formulations in blood is approximately 12 to 16 hours. Therefore, for continuous prevention, FVIII formulations are administered to patients three times a week (NPLs 3 and 4). In on-demand administration, FVIII formulations are also additionally administered as necessary at an interval to prevent rebleeding. In addition, the administration of FVIII formulations is intravenous. Therefore, there has been a strong need for pharmaceutical agents with a lesser burden in administration than FVIII formulations.

Occasionally, antibodies against FVIII (inhibitors) are raised in hemophilia patients. Such inhibitors counteract the effects of the FVIII formulations. For bleeding in patients who have developed inhibitors (inhibitor patients), bypassing agents are administered. Their mechanisms of action do not depend on the FVIII function, that is, the function of catalyzing the activation of blood coagulation factor X (FX) by activated blood coagulation factor IX (FIXa). Therefore, in some cases, bypassing agents cannot sufficiently stop the bleeding. Accordingly, there has been a strong need for pharmaceutical agents that are not affected by the presence of inhibitors and which functionally substitute for FVIII.

As a means for solving the problem, bispecific antibodies that functionally substitute for FVIII and their use have been reported (PTLs 1, 2, 3, and 4). The bispecific antibodies against FIXa and FX can functionally substitute for FVIII by positioning the two factors close to each other to exhibit FVIII mimetic activity (NPL 5). It has been reported that the FVIII mimetic activity of the antibodies can be enhanced by optimizing the affinity towards FIXa and FX (NPL 6). Emicizumab (ACE910) having high FVIII mimetic activity, which is one of these antibodies, has been reported to exhibit hemostatic effects in monkey models of hemophilia (NPLs 7 and 8); therefore, clinical trials are being conducted on hemophilia A patients.

CITATION LIST

Patent Literature

[PTL 1] WO 2005/035754
[PTL 2] WO 2005/035756
[PTL 3] WO 2006/109592
[PTL 4] WO 2012/067176

Non-Patent Literature

[NPL 1] Blood 58, 1-13 (1981)
[NPL 2] Nature 312, 330-337(1984)
[NPL 3] Nature 312, 337-342(1984)
[NPL 4] Biochim. Biophys. Acta 871, 268-278(1986)
[NPL 5] Nat Med. 2012 October; 18(10):1570-4.
[NPL 6] PLoS One. 2013; 8(2):e57479.
[NPL 7] J Thromb Haemost. 2014 February; 12(2):206-213.
[NPL 8] Blood. 2014 Nov. 13; 124(20):3165-71.
[NPL 9] J. Appl. Cryst. 13, 577-584 (1980)
[NPL 10] IUCrJ. 2, 9-18 (2015)

SUMMARY OF THE INVENTION

Technical Problem

The present invention was achieved in view of the above circumstances. An objective of the present invention is to provide antibody variants or isoforms with reduced FVIII mimetic activity.

Solution to Problem

The present inventors performed dedicated research to solve the above-described problems and succeeded in identifying antibody variants and isoforms which are contained in a pharmaceutical composition comprising Emicizumab as an active ingredient. The present inventors also found that FVIII mimetic activity of these antibody variants and isoforms is quite low, as compared with that of Emicizumab.

The present invention was made based on these findings, and provides [1] to [21] below.

[1] A variant of an antibody that comprises a variable region comprising the amino acid sequence SISPSGQSTYYR-REVKG (SEQ ID NO: 2), wherein
  (a) the amino acid residue R at the 12th position from the N terminus side of the sequence (the 61th position from the N terminus side of the Emicizumab Q chain: position 60 according to Kabat numbering) or
  (b) the amino acid residues YYR at the 10th to 12th positions from the N terminus side of the sequence (the 59th to 61th positions from the N terminus side of the Emicizumab Q chain: positions 58 to 60 according to Kabat numbering)
  is deleted and the variable region is cleaved at the deletion site.

[2] The antibody variant of [1], wherein the sequence is a CDR sequence.

[3] The antibody variant of [1], wherein the sequence is a CDR2 sequence.

[4] The antibody variant of [1], wherein the sequence is a sequence comprised in a heavy chain.

[5] The antibody variant of [1], which is a variant of a bispecific antibody.

[6] The antibody variant of [1], which is a variant of Emicizumab.

[7] A method for detecting the antibody variant of any one of [1] to [6], comprising the step of separating a sample containing an antibody that comprises a variable region comprising the amino acid sequence SISPSGQSTYYR-REVKG (SEQ ID NO: 2) by affinity chromatography, ion exchange chromatography, normal phase chromatography, reverse phase chromatography, hydrophilic interaction chromatography (HILIC), hydrophobic interaction chromatography (HIC), separation based on charge, size exclusion chromatography (SEC), gel permeation chromatography (GPC), or combinations thereof.

[8] The method for detecting of [7], which uses the antibody variant of any one of [1] to [6] as a reference standard.

[8-2] The method for detecting of [8], comprising the step of conducting one or more analysis selected from the group consisting of quantitative analysis, qualitative analysis, and structural analysis.

[9] A pharmaceutical composition comprising the antibody variant of any one of [1] to [6], wherein the percentage of the antibody variant in the total antibody molecules in the pharmaceutical composition is 5% or less.

[10] The pharmaceutical composition of [9], wherein the antibody is Emicizumab.

[11] The pharmaceutical composition of [9], which is obtained by a purification process comprising purification by cation exchange chromatography (CEX).

[12] A method for suppressing production of the antibody variant of any one of [1] to [6], comprising the step of culturing antibody producing cells at a pH of 7.1 or more, and/or at a culture temperature of 36° C. or less.

[12-2] The method of [12], wherein conditions for culturing the antibody producing cells are changed to pH of 7.1 or more, and/or culture temperature of 36° C. or less during culturing.

[13] An isoform of a bispecific antibody comprising a first heavy chain (Q chain, SEQ ID NO: 10) and a second heavy chain (J chain, SEQ ID NO: 11), wherein disulfide bonds are formed in the following:
(1a) between cysteine at position 144 according to EU numbering of the first heavy chain (the 150th position from the N terminus side of SEQ ID NO: 10) and cysteine at position 200 according to EU numbering of the second heavy chain (the 202nd position from the N terminus side of SEQ ID NO: 11); and
(1b) between cysteine at position 200 according to EU numbering of the first heavy chain (the 206th position from the N terminus side of SEQ ID NO: 10) and cysteine at position 144 according to EU numbering of the second heavy chain (the 146th position from the N terminus side of SEQ ID NO: 11), or wherein disulfide bonds are formed in the following:
(2a) between cysteine at position 226 according to EU numbering of the first heavy chain (the 229th position from the N terminus side of SEQ ID NO: 10) and cysteine at position 229 according to EU numbering of the second heavy chain (the 228th position from the N terminus of SEQ ID NO: 11); and
(2b) between cysteine at position 229 according to EU numbering of the first heavy chain (the 232nd position from the N terminus of SEQ ID NO: 10) and cysteine at position 226 according to EU numbering of the second heavy chain (the 225th position from the N terminus of SEQ ID NO: 11).

[14] The bispecific antibody isoform of [13], wherein disulfide bonds are formed in (1a) and (1b).

[15] An isoform of a bispecific antibody comprising a first heavy chain (Q chain, SEQ ID NO: 10) and a second heavy chain (J chain, SEQ ID NO: 11), characterized in that it elutes at a region more to the alkaline side than the bispecific antibody when separated using cation exchange chromatography.

[16] The bispecific antibody isoform of any one of [13] to [15], which is an isoform of Emicizumab.

[17] A method for detecting the antibody isoform of any one of [13] to [16], comprising the step of separating a sample containing a bispecific antibody by affinity chromatography, ion exchange chromatography, normal phase chromatography, reverse phase chromatography, hydrophilic interaction chromatography (HILIC), hydrophobic interaction chromatography (HIC), separation based on charge, size exclusion chromatography (SEC), gel permeation chromatography (GPC), or combinations thereof.

[18] The method for detecting of [17], which uses the bispecific antibody isoform of any one of [13] to [16] as a reference standard.

[18-2] The method for detecting of [18], comprising the step of conducting one or more analysis selected from the group consisting of quantitative analysis, qualitative analysis, and structural analysis.

[19] A pharmaceutical composition comprising the bispecific antibody isoform of any one of [13] to [16], wherein the percentage of the antibody isoform in the total antibody molecules in the pharmaceutical composition is 2% or less.

[20] A method for reducing the content percentage of the bispecific antibody isoform of any one of [13] to [16], comprising the step of purification by cation exchange chromatography.

[21] The antibody isoform or variant of [1], [13], or [15], wherein the biological activity of the antibody is markedly reduced.

[22] An isoform of an antibody having two variable regions each of which recognizes different epitopes or of a derivative thereof, wherein the isoform has an average Rg value that is smaller by 3% or more, preferably 4% or more, more preferably 5% or more, or still more preferably 6% or more, relative to the antibody or derivative thereof, and/or wherein the isoform has an average Dmax value that is smaller by 5% or more, preferably 6% or more, more preferably 7% or more, or still more preferably 7.5% or more, relative to the antibody or derivative thereof.

[23] An isoform of an antibody having two variable regions each of which recognizes different epitopes or of a derivative thereof, wherein the isoform has an average Rg value that is smaller by 0.15 nm or more, preferably 0.2 nm or more, more preferably 0.25 nm or more, or still more preferably 0.3 nm or more, relative to the antibody or derivative thereof, and/or wherein the isoform has an average Dmax value that is smaller by 0.5 nm or more, preferably 1.0 nm or more, more preferably 1.2 nm or more, or still more preferably 1.4 nm or more, relative to the antibody or derivative thereof.

[24] The isoform of [22] or [23], wherein the isoform has disulfide bond(s) different from those in the antibody or derivative thereof.

[25] The isoform of any one of [22] to [24], wherein the antibody or derivative thereof is Emicizumab (a bispecific antibody that comprises a first heavy chain (Q chain, SEQ ID NO: 10), a second heavy chain (J chain, SEQ ID NO: 11), and common light chains each one of which forms a pair with the first heavy chain or the second heavy chain (SEQ ID NO: 12)).

[26] An isoform of Emicizumab, wherein the isoform has an average Rg value of 4.9 nm or less, or preferably 4.8 nm or less, and/or wherein the isoform has an average Dmax value of 17.0 nm or less, or preferably 16.5 nm or less.

[27] The isoform of [25] or [26], wherein the isoform has disulfide bonds between cysteine at position 144 according to EU numbering of the first heavy chain (the 150th position from the N terminus side of SEQ ID NO: 10) and cysteine at position 200 according to EU numbering of the second heavy chain (the 202nd position from the N terminus side of SEQ ID NO: 11) and between cysteine at position 200 according to EU numbering of the first heavy chain (the 206th position from the N terminus side of SEQ ID NO: 10) and cysteine at position 144 according to EU numbering of the second heavy chain (the 146th position from the N terminus side of SEQ ID NO: 11).

[28] A pharmaceutical composition comprising Emicizumab and the isoform of any one of [22] to [27], wherein the percentage of the isoform in the total antibody molecules in the pharmaceutical composition is 2% or less.

[29] An isoform of a bispecific antibody (Q499-z121/J327-z119/L404-k; Emicizumab), the bispecific antibody comprising a first heavy chain (Q chain, SEQ ID NO: 10), second heavy chain (J chain, SEQ ID NO: 11), and common L chains each one of which forms a pair with the first heavy chain or the second heavy chain (SEQ ID NO: 12), wherein the isoform has a difference in molecular structure from Emicizumab in amino acid residues from position 146 according to EU numbering of the Q chain to position 174 according to EU numbering of the Q chain (the 152nd position to the 180th position from the N terminus side of SEQ ID NO: 10) and amino acid residues from position 146 according to EU numbering of the J chain to position 174 according to EU numbering of the J chain (the 148th position to the 176th position from the N terminus side of SEQ ID NO: 11).

[30] The isoform of [29], wherein the difference in molecular structure is measured as a difference in deuterium exchange rate (% D) in HDX-MS measurement.

[31] A pharmaceutical composition comprising Emicizumab and the isoform of [29] or [30], wherein the percentage of the isoform in the total antibody molecules in the pharmaceutical composition is 2% or less.

The present invention further provides [A1] to [A9] below.

[A1] The method for detecting of [7] or [17], comprising the step of subjecting a sample containing the antibody and/or the antibody variant or isoform to reduction reaction, hydrolysis reaction (digestion reaction), protein denaturation reaction, or a combination thereof.

[A2] The method for detecting of [A1], wherein the reduction reaction is carried out under mild reducing conditions (for example, reduction with DTT in Tris buffer (pH7.0) at 37° C.).

[A3] The method for detecting of [A1], wherein the hydrolysis reaction is carried out using a site-specific cleavage enzyme (for example, a sequence-specific protease such as IdeS protease, Lys-C, papain, etc.).

[A4] The method for detecting of any one of [7], [17], and [A1] to [A3], comprising the step of separating a sample containing the antibody, the antibody variant or isoform, a reaction product thereof, or a combination thereof by affinity chromatography, ion exchange chromatography, normal phase chromatography, reverse phase chromatography, hydrophilic interaction chromatography (HILIC), hydrophobic interaction chromatography (HIC), separation based on charge, size exclusion chromatography (SEC), gel permeation chromatography (GPC), or combinations thereof.

[A5] The method for detecting of any one of [8], [18], and [A1] to [A4], comprising the step of analyzing by SE-HPLC analysis, dynamic light scattering (DLS) method, SAXS measurement, electron microscopic measurement, 3D modeling, SPR assay, HDX MS analysis, or a combination thereof.

[A6] A method for quality control of a pharmaceutical composition comprising Emicizumab, comprising the step of [7], [8], [17], [18], or [A1] to [A5] or a step of combining these methods.

[A7] A method for producing a pharmaceutical composition comprising Emicizumab, comprising a step from the method of [A6].

[A8] A method for purifying a composition comprising Emicizumab, characterized in that the method comprises a step of the Bind & Elute mode of cation exchange chromatography (CEX).

[A9] A method for producing a pharmaceutical composition comprising Emicizumab, comprising a step from the method for purifying of [A8].

Effects of the Invention

The present inventors succeeded in identifying antibody variants and isoforms which are contained in a pharmaceutical composition comprising Emicizumab as an active ingredient. The present inventors also found that FVIII mimetic activity of these antibody variants and isoforms is quite low, as compared with that of Emicizumab. Therefore, pharmaceutical compositions comprising Emicizumab with such an antibody variant and isoform only at low content rate are useful as a means for treating hemophilia.

BRIEF DESCRIPTION OF DRAWINGS

FIGS. 3A-D show the results of separating Emicizumab and Protected Disulfide Isoforms, after IdeS-digestion and reduction treatments, by reverse phase high performance liquid chromatography. FIGS. 3A to D show the results of separation for samples containing Emicizumab (A and B) or Protected Disulfide Isoforms (C and D) which were IdeS digested and then reduced under the condition where the denaturant is present (A and C: complete reduction condition) or the condition where the denaturant is not present (B and D: partial reduction condition). For the samples from the full reduction condition (FIGS. 3A and C), the peaks representing Q chain Fd (Q-Fd), J chain Fd (J-Fd), Q chain Fc (Q-Fc), J chain Fc (J-Fc), and L chain (LC) are all detected for Emicizumab and Protected Disulfide Isoforms: no difference in reduction pattern was detected between Emicizumab and Protected Disulfide Isoforms. On the other hand, for the samples from the partial reduction condition (FIGS. 3B and D), the same peaks representing Q chain Fd, J chain Fd, Q chain Fc, J chain Fc, and L chain were detected as in the full reduction condition and, in addition thereto, a unique peak indicating the heterodimer of Q chain Fd and J chain Fd disulfide bonded together (J-Fd-Q-Fd) was detected only for Protected Disulfide Isoforms.

FIGS. 4A-D show the results of separating Emicizumab and Protected Disulfide Isoforms after IdeS digestion (and reduction treatment), by reverse phase high performance liquid chromatography. FIGS. 4A and B show the results of separation for Protected Disulfide Isoforms (A) or Emicizumab (B) which were IdeS digested. FIGS. 4C and D show the results of separation for Protected Disulfide Isoforms (C) or Emicizumab which were IdeS digested and then treated for denaturation. Regardless of whether being treated for denaturation or not, the F(ab')2 portion (LC-J Fab-Q Fab-LC) of Protected Disulfide Isoforms was separated with longer retention time than the main component of Emicizumab.

FIGS. 8A-D show results from analyzing molecular structure of Emicizumab (Main) and Protected Disulfide Isoform (BiAb3) with the SAXS device. "Pair-distance distribution function [p(r)]", "Rg (nm)", and "Dmax (nm)" indicate the pair distance distribution function, radius of gyration, and maximum dimension, respectively.

DESCRIPTION OF EMBODIMENTS

Figure 1A:
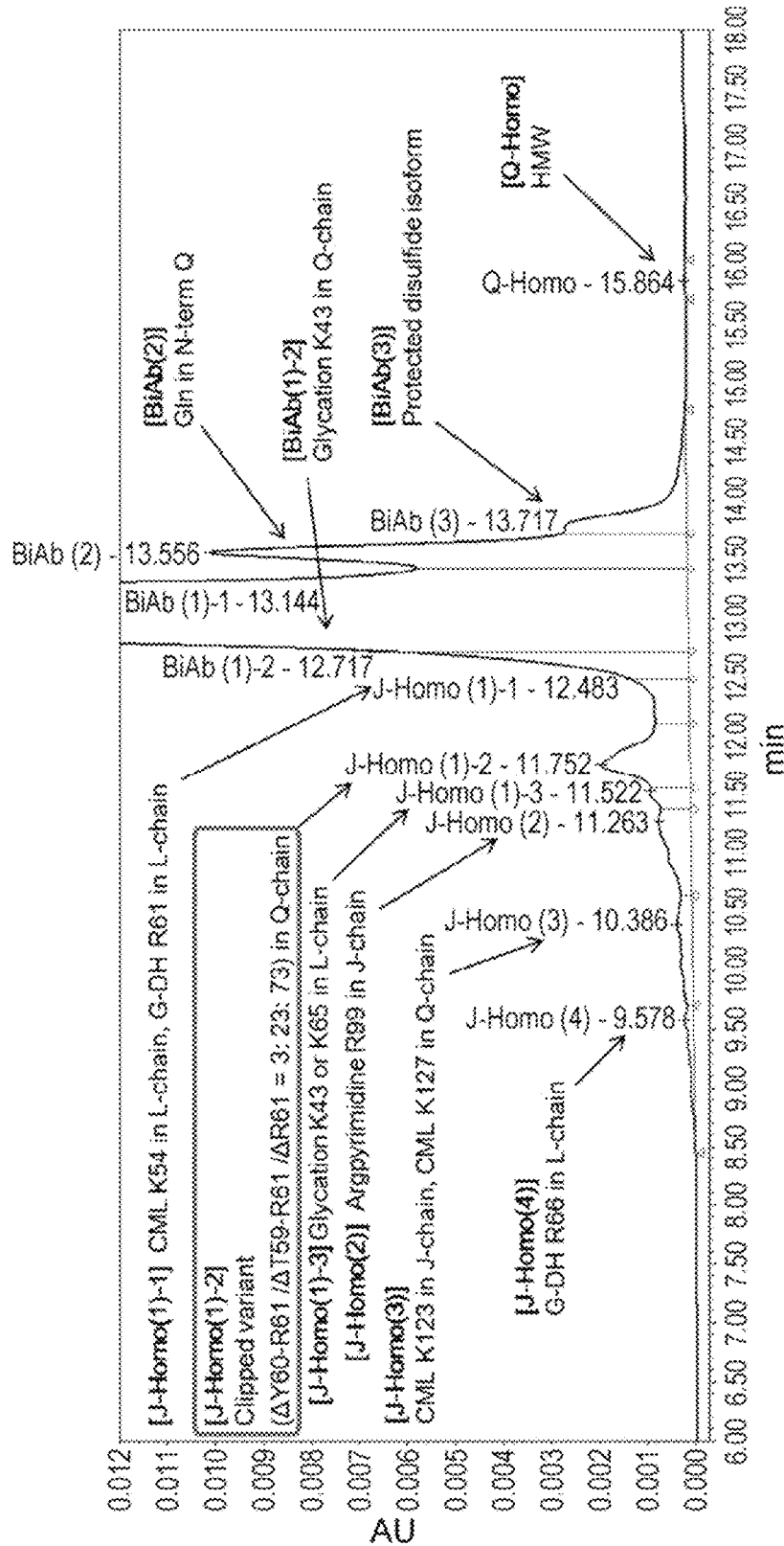
FIG. 1A shows the results of separation of Emicizumab drug substance by CE-HPLC. The peak marked with a thick-bordered box indicates Q-CDR-Clipped Variants.

One embodiment of the present invention relates to antibody variants and isoforms with reduced biological activity (for example, reduced FVIII mimetic activity). The antibody variants and isoforms were identified during the present inventors' analyzing the Emicizumab drug substance, as two types of structurally changed molecules (Q-CDR-Clipped Variants and the Protected Disulfide Isoforms). In the present application, the "antibody variant" and the "antibody isoform" may also be referred to as a mutant or isomer of an antibody molecule.

Emicizumab is a bispecific humanized IgG4 antibody showing an activity to functionally substitute for FVIII as cofactor and comprising an anti-FIX(a) and an anti-FX, and is composed of two types of heavy chains (Q499 and J327), each of which recognizes FIX(a) and FX respectively, and common L chains (L404).

Specifically, Emicizumab is a bispecific antibody where a first polypeptide and a third polypeptide form a pair, and a second polypeptide and a fourth polypeptide form a pair; where the first polypeptide comprises an H chain comprising the amino acid sequences of H-chain CDRs 1, 2, and 3 of SEQ ID NOs: 1, 2, and 3 (H-chain CDRs of Q499), respectively; the second polypeptide comprises an H chain comprising the amino acid sequences of H-chain CDRs 1, 2, and 3 of SEQ ID NOs: 4, 5, and 6 (H-chain CDRs of J327), respectively; and the third polypeptide and the fourth polypeptide comprise a common L chain comprising the amino acid sequences of L-chain CDRs 1, 2, and 3 of SEQ ID NOs: 7, 8, and 9 (L-chain CDRs of L404), respectively (Q499-z121/J327-z119/L404-k).

More specifically, Emicizumab is a bispecific antibody where a first polypeptide and a third polypeptide form a pair, and a second polypeptide and a fourth polypeptide form a pair; where the first polypeptide comprises an H chain comprising the amino acid sequence of H-chain variable region of SEQ ID NO: 13, the second polypeptide comprises an H chain comprising the amino acid sequence of H-chain variable region of SEQ ID NO: 14, and the third polypeptide and the fourth polypeptide comprise a common L chain comprising the amino acid sequence of L-chain variable region of SEQ ID NO: 15.

Still more specifically, Emicizumab is a bispecific antibody where a first polypeptide and a third polypeptide form a pair, and a second polypeptide and a fourth polypeptide form a pair; where the first polypeptide comprises an H chain comprising the amino acid sequence of SEQ ID NO: 10, the second polypeptide comprises an H chain comprising the amino acid sequence of SEQ ID NO: 11, and the third polypeptide and the fourth polypeptide comprise a common L chain of SEQ ID NO: 12 (Q499-z121/J327-z119/L404-k).

Such antibodies can be obtained by the methods described in WO 2005/035756, WO 2006/109592, WO 2012/067176, and such.

Antibodies used in the present invention are not particularly limited so long as they bind to a desired antigen, and they may be polyclonal or monoclonal antibodies. Monoclonal antibodies are preferred in that homogeneous antibodies can be stably produced.

Amino acids contained in the amino acid sequences of the present invention may be post-translationally modified (for example, the modification of an N-terminal glutamine into a pyroglutamic acid by pyroglutamylation is well-known to those skilled in the art). Naturally, such post-translationally modified amino acids are included in the antibodies used in the present invention.

In the present invention, the biological activity of the antibody or antibody variants or antibody isoforms is preferably FVIII mimetic activity. In the present invention the "FVIII mimetic activity" means an activity to functionally substitute for FVIII (activity to functionally substitute for FVIII as cofactor). In the present invention, the phrase "functionally substituting for FVIII" means recognizing FIX or FIXa, and FX, and promoting FX activation by FIXa (promoting FXa production by FIXa). FXa production-promoting activity can be evaluated using, for example, a measurement system comprising FIXa, FX, synthetic substrate S-2222 (synthetic substrate of FXa), and phospholipids. Such a measurement system shows a correlation with the disease severity and clinical symptoms in hemophilia A cases (Rosen S, Andersson M, Blombäck M et al. Clinical applications of a chromogenic substrate method for determination of FVIII activity. Thromb Haemost 1985; 54: 811-23).

FVIII mimetic activity of the antibodies such as Emicizumab and antibody variants and antibody isoforms can be evaluated, for example, methods described in WO 2005/035756, WO 2006/109592, WO 2012/067176, etc.

In the present invention, the antibodies or the antibody variants or isoforms are said to "have a reduced biological activity" when the biological activity is reduced as compared with the biological activity of a reference antibody, and it is preferred that the reduction is statistically significant. In the present invention, the antibodies or the antibody variants or the antibody isoforms are said to "have markedly (or extremely) reduced biological activity" when the biological activity is reduced as compared with the biological activity of a reference antibody by 10% or more, for example, 20% or more, 30% or more, 40% or more, 50% or more, 60% or more, 70% or more, 80% or more, or 90% or more.

In the present invention, the terms "Q chain" and "J chain" refer to an H chain (a heavy chain) comprising a variable region that can exhibit binding ability to FIX(a) and FX, respectively.

In the present invention, the term "common L chain" refers to an L chain that can form pairs with each of two or more different H chains and can exhibit binding ability to their respective antigen. Herein, the term "different H chains" preferably refers to H chains of antibodies against different antigens, but is not limited thereto; it refers to H chains whose amino acid sequences are different from each other. Common L chains can be obtained, for example, according to the methods described in WO 2006/109592.

The term "antibody" is used in the broadest sense, and includes monoclonal antibodies, polyclonal antibodies, dimers, multimers, multispecific antibodies (such as bispecific antibodies), antibody derivatives, and modified antibodies (Miller K et al. J Immunol. 2003, 170(9), 4854-61) so long as they show a desired biological activity. The antibodies may be mouse antibodies, human antibodies, humanized antibodies, chimeric antibodies, or those derived from another species, or artificially synthesized antibodies. The antibodies disclosed herein can be of any type (for example, IgG, IgE, IgM, IgD, and IgA), class (for example, IgG1, IgG2, IgG3, IgG4, IgA1 and IgA2) or subclass of immunoglobulin molecules. The immunoglobulins can be derived from any species (for example, human, mouse, or rabbit). The terms "antibody", "immune globulin" and "immunoglobulin" are used interchangeably in a broad sense.

"Bispecific antibody" refers to an antibody having two variable regions that each recognize different epitopes, where the variable regions are present in the same antibody molecule. Bispecific antibodies may be antibodies that recognize two or more different antigens, or antibodies that recognize two or more different epitopes on the same antigen. Bispecific antibodies may include not only whole antibodies but antibody derivatives.

Recombinant antibodies produced by using genetic engineering techniques can be used as the antibodies. A recombinant antibody can be obtained by cloning a DNA encoding the antibody from hybridomas or antibody-producing cells such as sensitized lymphocytes that produce antibodies; inserting this into a vector; and then introducing it into hosts (host cells) to produce the antibody.

Bispecific antibodies are not limited to those of the IgG type; for example, IgG-type bispecific antibodies can be secreted from a hybrid hybridoma (quadroma) produced by fusing two types of hybridomas that produce IgG antibodies (Milstein C. et al., Nature 1983, 305: 537-540). They can also be secreted by introducing into cells the L-chain and H-chain genes constituting the two kinds of IgGs of interest, i.e., a total of four kinds of genes, to co-express the genes.

The antibodies of the present invention can be produced by methods known to those skilled in the art. Specifically, a DNA encoding the antibody of interest is inserted into an expression vector. The insertion into the expression vector is carried out such that the expression will take place under the control of expression regulatory regions such as an enhancer and a promoter. Next, host cells are transformed using this expression vector to express the antibody. Appropriate combinations of a host and an expression vector can be used in this case.

The antibodies of the present invention thus obtained can be isolated from the inside of host cells or the outside of the cells (medium, etc.), and purified to be substantially pure, homogeneous antibodies. The antibodies can be separated and purified by methods ordinarily used for separating and purifying antibodies, and the methods are not limited in any way. For example, methods described in WO 2013/086448 are known for separating IgG2 disulfide isoform. For separation and purification of the antibodies and the antibody variants or antibody isoforms in the present invention, for example, the antibodies and the antibody variants or antibody isoforms can be separated and purified by appropriately selecting and combining column chromatography, filtration, ultrafiltration, salting-out, solvent precipitation, solvent extraction, distillation, immunoprecipitation, SDS-polyacrylamide gel electrophoresis, isoelectrofocusing, dialysis, recrystallization, and such. For example, in the separation and purification using a chromatography column, various types of matrix including a strong cation exchange matrix, weak cation exchange matrix, anti-human IgG affinity matrix, and protein L matrix can be used.

In one aspect, the present invention relates to the antibody variants having the characteristic features described below (sometimes called "Q-CDR-Clipped Variants" in the present application):
- having extremely low biological activity (FVIII mimetic activity) as compared with Emicizumab;
- the fragment on the N-terminus side and the other fragment on the C-terminus side of the deleted amino acid residue(s) are joined together via a disulfide bond (FIG. 1B);
- the amount of production varies depending upon time, temperature, and pH for culturing antibody producing cells.

In one embodiment, Q-CDR-Clipped Variant is a variant of an antibody that comprises a variable region comprising the amino acid sequence SISPSGQSTYYRREVKG (SEQ ID NO: 2), wherein
  (a) the amino acid residue R at the 12th position from the N terminus side of the amino acid sequence of SEQ ID NO: 2 (the 61th position from the N terminus side of the Emicizumab Q chain: position 60 according to Kabat numbering); or
  (b) the amino acid residues YYR at the 10th to 12th positions from the N terminus side of the amino acid sequence of SEQ ID NO: 2 (the 59th to 61th positions from the N terminus side of the Emicizumab Q chain: positions 58 to 60 according to Kabat numbering), is/are deleted and the variable region is cleaved at the deletion site.

Q-CDR-Clipped Variants are preferably variants of a bispecific antibody, and more preferably variants of Emicizumab.

In another aspect, the present invention relates also to methods for detecting and methods for analyzing Q-CDR-Clipped Variant. In one embodiment, the methods for detecting Q-CDR-Clipped Variant comprises the step of separating a sample containing an antibody that comprises a variable region comprising the amino acid sequence SISPSGQSTYYRREVKG (SEQ ID NO: 2) by affinity chromatography, ion exchange chromatography, normal phase chromatography, reverse phase chromatography, hydrophilic interaction chromatography (HILIC), hydrophobic interaction chromatography (HIC), separation based on charge, size exclusion chromatography (SEC), gel permeation chromatography (GPC), or a combination thereof. In one embodiment, the methods for analyzing Q-CDR-Clipped Variant comprise the step of conducting one or more analysis selected from the group consisting of quantitative analysis, qualitative analysis, and structural analysis, using a Q-CDR-Clipped Variant as a reference standard.

In such methods for detecting and methods for analyzing, the presence or absence of deleted part(s) in Fab having the amino acid sequence of SEQ ID NO: 2 (Q chain Fab) can be used as an indicator for the detection and analysis. The deleted part(s) may be detected, for example, by using a shift in the molecular weight resulting from the deletion in LCMS analysis as an indicator. In Q-CDR-Clipped Variants, the fragment on the N terminus side and the other fragment on the C-terminus side of the deleted amino acid residue(s) are joined together via a disulfide bond; therefore, difference in reduction patterns arising based on the presence or absence of the deleted part(s) can be detected by analyzing samples after being subjected to reaction to reduce disulfide bond(s), utilizing various analytical techniques such as CE-HPLC, LCMS, and LC-UV. Structural analysis by NMR measurement and such can also be utilized.

Alternatively, difference in resolution by ion exchange chromatography may be used as an indicator. For example, when separation is carried out by cation exchange chromatography, Q-CDR-Clipped Variants will be separated in a region more acidic than the main peak of Emicizumab.

In another aspect, in the present invention, production and quality control of pharmaceutical compositions comprising Emicizumab can be implemented by carrying out one of the above described methods for detecting and methods for analyzing or any combination thereof. Therefore, the present invention relates to methods for quality control of a pharmaceutical composition comprising Emicizumab, comprising a step of carrying out the above described methods for detecting and methods for analyzing or a step of combining any of those. The present invention also relates to production of a pharmaceutical composition comprising Emicizumab, comprising the step of carrying out such method(s) for quality control.

In another aspect, the present invention relates to a pharmaceutical composition comprising Emicizumab and Q-CDR-Clipped Variant(s), in which the ratio of Q-CDR-Clipped Variant(s) in total antibody molecules in the pharmaceutical composition is kept low. The pharmaceutical composition may be obtained by purification process comprising purification by cation exchange chromatography (CEX). For example, an antibody solution containing Emicizumab and Q-CDR-Clipped Variants is absorbed onto a cation exchange column, and after that, only acidic-side variants including Q-CDR-Clipped Variants may be selectively eluted and removed. The ratio of Q-CDR-Clipped Variants in total antibody molecules in the pharmaceutical composition can be evaluated by various methods, including the above-described methods for detecting/analyzing Q-CDR-Clipped Variant, and may be expressed by ratio of the peak area for Q-CDR-Clipped Variants (peak area ratio) from analyzing the pharmaceutical composition using cation exchange chromatography (CEX) or CE-HPLC, for example. The ratio of Q-CDR-Clipped Variants in total antibody molecules in the pharmaceutical composition (for example, CEX peak area ratio) is preferably 5% or less, and, for example, is 5.0% or less, 4.0% or less, 3.0% or less, 2.0% or less, or 1.0% or less.

The present invention further relates to methods for producing a pharmaceutical composition in which Q-CDR-Clipped Variant content rate is kept low, and methods for suppressing formation of Q-CDR-Clipped Variant. Q-CDR-Clipped Variant formation amount can be reduced by shortening culture time (for example, to 15 days or less, and preferably to 13 days or less), or by lowering culture temperature (for example, to 38° C. or less, preferably to 37° C. or less, and more preferably to 36° C. or less), and/or by elevating culture pH (for example, to 6.7 or higher, preferably to 6.9 or higher, and more preferably to 7.1 or higher) for antibody-producing cells (FIGS. 4A to D). Therefore, the above-described methods are characterized in that the methods comprise the step of culturing antibody (for example, Emicizumab) producing cells at lower culture temperature (for example, about 36° C. or less) and at higher pH (for example, about 7.1 or higher) than conventional, for a certain length of time (for example, about 15 days or less). In one embodiment, the above-described methods comprise the step of culturing antibody producing cells at pH of 7.1 or higher, and/or at culture temperature of 36° C. or less. In certain embodiments, the above-described methods are characterized in that the culture condition for the antibody producing cells are shifted to at pH of 7.1 or higher and/or at culture temperature of 36° C. or less in the midway of the culture (for example, on day 2 or later of the culture).

In another aspect, the present invention relates to methods for purifying a composition comprising Emicizumab, which methods are characterized in comprising a step of the Bind & Elute mode of cation exchange chromatography (CEX). The present invention further relates to methods for producing a pharmaceutical composition comprising Emicizumab, the methods comprising a step of carrying out the method for purification.

In another aspect, the present invention relates to the antibody isoforms having the characteristic features described below (sometimes called "Protected Disulfide Isoforms" in the present application):

having an extremely low biological activity (FVIII mimetic activity) as compared with Emicizumab;
more strongly hydrophobic as compared with Emicizumab;
having inter-heavy chain disulfide bonds (FIG. 2B) which are less susceptible to reduction under mild conditions (partial reduction conditions) as compared with those in Emicizumab;
formed irrespective of conditions (production parameters) such as dissolved oxygen concentration and initial pH of culture medium for antibody-producing cells, and culture time before adding MTX (methotrexate).

In one embodiment, Protected Disulfide Isoforms are characterized in that they can bind to FIX(a) and FX, the antigens, but do not exhibit biological activity (FVIII mimetic activity).

In certain embodiments, Protected Disulfide Isoforms are structural isomers having (normal) disulfide bonds identical to Emicizumab, but having stronger hydrophobicity than the usual due to structural change(s) in the Fab portion, thereby having inter-heavy chain disulfide bonds which have become less susceptible to reduction than the usual.

In another embodiment, Protected Disulfide Isoforms are isoforms of a bispecific antibody that comprises a first heavy chain (Q chain, SEQ ID NO: 10) and a second heavy chain (J chain, SEQ ID NO: 11), wherein, in Protected Disulfide Isoforms, disulfide bonds are formed in the following:
(1a) between cysteine at position 144 according to EU numbering of the first heavy chain (the 150th position from the N terminus side of SEQ ID NO: 10) and cysteine at position 200 according to EU numbering of the second heavy chain (the 202nd position from the N terminus side of SEQ ID NO: 11); and
(1b) between cysteine at position 200 according to EU numbering of the first heavy chain (the 206th position from the N terminus side of SEQ ID NO: 10) and cysteine at position 144 according to EU numbering of the second heavy chain (the 146th position from the N terminus side of SEQ ID NO: 11), or wherein disulfide bonds are formed in the following:
(2a) between cysteine at position 226 according to EU numbering of the first heavy chain (the 229th position from the N terminus side of SEQ ID NO: 10) and cysteine at position 229 according to EU numbering of the second heavy chain (the 228th position from the N terminus side of SEQ ID NO: 11); and
(2b) between cysteine at position 229 according to EU numbering of the first heavy chain (the 232nd position from the N terminus side of SEQ ID NO: 10) and cysteine at position 226 according to EU numbering of the second heavy chain (the 225th position from the N terminus side of SEQ ID NO: 11).

In a particular embodiment, Protected Disulfide Isoforms are isoforms of a bispecific antibody and preferably are isoforms of Emicizumab, wherein, in Protected Disulfide Isoforms, disulfide bonds are formed in the following:
(1a) between cysteine at position 144 according to EU numbering of the first heavy chain (the 150th position from the N terminus side of SEQ ID NO: 10) and cysteine at position 200 according to EU numbering of the second heavy chain (the 202nd position from the N terminus side of SEQ ID NO: 11);
(1b) between cysteine at position 200 according to EU numbering of the first heavy chain (the 206th position from the N terminus side of SEQ ID NO: 10) and cysteine at position 144 according to EU numbering of the second heavy chain (the 146th position from the N terminus side of SEQ ID NO: 11);
(1c) between cysteine at position 226 according to EU numbering of the first heavy chain (the 229th position from the N terminus side of SEQ ID NO: 10) and cysteine at position 226 according to EU numbering of the second heavy chain (the 225th position from the N terminus side of SEQ ID NO: 11); and
(1d) between cysteine at position 229 according to EU numbering in the first heavy chain (the 232nd position from the N terminus side of SEQ ID NO: 10) and cysteine at position 229 according to EU numbering in the second heavy chain (the 228th position from the N terminus side of SEQ ID NO: 11), or wherein disulfide bonds are formed in the following:
(2a) between cysteine at position 226 according to EU numbering of the first heavy chain (the 229th position from the N terminus side of SEQ ID NO: 10) and cysteine at position 229 according to EU numbering of the second heavy chain (the 228th position from the N terminus side of SEQ ID NO: 11);
(2b) between cysteine at position 229 according to EU numbering of the first heavy chain (the 232nd position from the N terminus side of SEQ ID NO: 10) and cysteine at position 226 according to EU numbering of the second heavy chain (the 225th position from the N terminus side of SEQ ID NO: 11);
(2c) between cysteine at position 144 according to EU numbering of the first heavy chain (the 150th position from the N terminus side of SEQ ID NO: 10) and cysteine at position 200 according to EU numbering of the first heavy chain (the 206th position from the N terminus side of SEQ ID NO: 10); and
(2d) between cysteine at position 144 according to EU numbering of the second heavy chain (the 146th position from the N terminus side of SEQ ID NO: 11) and cysteine at position 200 according to EU numbering of the second heavy chain (the 202nd position from the N terminus side of SEQ ID NO: 11).

In another aspect, the present invention relates to methods for detecting and methods for analyzing Protected Disulfide Isoform. In one embodiment, the methods for detecting Protected Disulfide Isoform comprises the step of separating a sample containing a bispecific antibody by affinity chromatography, ion exchange chromatography, normal phase chromatography, reverse phase chromatography, hydrophilic interaction chromatography (HILIC), hydrophobic interaction chromatography (HIC), separation based on charge, size exclusion chromatography (SEC), gel permeation chromatography (GPC), or a combination thereof. In one embodiment, the methods for analyzing Protected Disulfide Isoform comprise the step of conducting one or more analysis selected from the group consisting of quantitative analysis, qualitative analysis, and structural analysis, using Protected Disulfide Isoform as a reference standard.

In such methods for detecting and methods for analyzing, analysis can be made utilizing difference(s) between Protected Disulfide Isoforms and Emicizumab in the structure of the region(s) forming inter-heavy chain disulfide bonds and/or of the Fab region. The structural difference(s) can be detected by various analytical methods, such as those shown below for example.

For example, the peak(s) reflecting the difference in three dimensional structure or strength of hydrophobicity between Emicizumab and Protected Disulfide Isoforms can be detected by analyzing a sample using a reverse phase column (for example, a C4 column), after the sample has been treated for digestion reaction by IdeS protease under non-reducing conditions (to cleave at a single site below the hinge region in IgG to give F(ab')2 and Fc fragments).

The peak(s) reflecting the difference in disulfide bond's susceptibility to reduction between Emicizumab and Protected Disulfide Isoforms can be detected by analyzing a sample using a reverse phase column, after the sample has been treated for IdeS digestion and thereafter for reduction reaction under mild reducing conditions (for example, reduction with DTT in Tris buffer solution (pH7.0) at 37° C.).

No difference will be detected in analysis results obtained using a reverse phase column for Emicizumab and Protected Disulfide Isoforms when the reduction reaction is carried out under the conditions where all disulfide bonds are reduced, whereas difference in reduction patterns will be detected in analysis results obtained using a reverse phase column for them when the reduction reaction is carried out under the above-described mild conditions. Without wishing to be limited by any particular theory, it is thought that, under the above-described mild reducing conditions, the disulfide bonds between the heavy chain and the light chain and the disulfide bonds between the heavy chains are all reduced in the case of Emicizumab, whereas only the disulfide bonds between the heavy chain and the light chain are reduced and the disulfide bonds between the heavy chains are left unreduced, in the case of Protected Disulfide Isoforms.

The peak(s) reflecting the difference in the Lys-C digestion pattern arising from the difference in three-dimensional structure between Emicizumab and Protected Disulfide Isoforms can be detected by analyzing a sample using a reverse phase column (for example, a C4 column), after the sample has been treated for limited Lys-C digestion (for example by stopping Lys-C digestion reaction halfway) under non-denaturing conditions (for example, in a Tris buffer solution). Without wishing to be limited by any particular theory, it is thought that the Lys-C digestion patterns reflecting the difference in three-dimensional structure are detected, as a result that cleavage is made preferentially at positions where Lys-C is easily accessible in a state where three-dimensional structure is retained during Lys-C digestion under non-denaturing conditions.

Alternatively, the peak(s) reflecting the difference in the Lys-C digestion pattern arising from the difference in three-dimensional structure between Emicizumab and Protected Disulfide Isoforms can be detected by analyzing a sample using a reverse phase column, after the sample, pre-treated for denaturation (for example, treated with 5M guanidine at 37° C. for 30 minutes) but not reduced (i.e., retains the SS bonds), has been treated for limited Lys-C digestion. Without wishing to be limited by any particular theory, it is thought that the Lys-C digestion patterns reflecting the difference in the SS bonds are detected, as a result of that cleavage is made preferentially at positions where Lys-C is easily accessible in a state where three-dimensional structure is no longer retained but the SS bonds (disulfide bonds) are retained as the Lys-C digestion is carried out for the denatured but non-reduced samples.

In addition to the above-described reduction reaction, IdeS digestion, and limited Lys-C digestion under non-denaturing conditions or denaturing conditions, various other decomposition reactions such as papain digestion can be utilized. In addition to reverse phase chromatography using a C4 column and such, various analytical techniques such as SE-HPLC analysis, dynamic light scattering (DLS), SAXS measurement, electron microscopy measurement, 3D modeling, SPR assay, HDX MS analysis can be utilized.

In another aspect, in the present invention, production and quality control of pharmaceutical compositions comprising Emicizumab can be implemented by carrying out one of the above described methods for detecting and methods for analyzing or any combination thereof. Therefore, the present invention relates to methods for quality control of a pharmaceutical composition comprising Emicizumab, comprising a step of carrying out the above described methods for detecting and methods for analyzing or a step of combining any of those. The present invention also relates to production of a pharmaceutical composition comprising Emicizumab, comprising the step of carrying out such method(s) for quality control.

In another aspect, the present invention relates to a pharmaceutical composition comprising Emicizumab and Protected Disulfide Isoform(s), in which the ratio of Protected Disulfide Isoform(s) in total antibody molecules in the pharmaceutical composition is kept low. The ratio of Protected Disulfide Isoform in total antibody molecules in the pharmaceutical composition can be evaluated by various methods, including the above-described methods for detecting/analyzing Protected Disulfide Isoform, and may be expressed by ratio of the peak area for Protected Disulfide Isoform (peak area ratio) from analyzing the pharmaceutical composition using cation exchange chromatography (CEX) or CE-HPLC, for example. The ratio of Protected Disulfide Isoform in total antibody molecules in the pharmaceutical composition (for example, CEX peak area ratio) is preferably 2% or less, and, for example, is 2.0% or less, 1.5% or less, 1.0% or less, or 0.5% or less.

In another aspect, the present invention relates to methods for purifying a composition comprising Emicizumab, which methods are characterized in comprising a step of the Bind & Elute mode of cation exchange chromatography (CEX). The present invention further relates to methods for producing a pharmaceutical composition comprising Emicizumab, the methods comprising a step of carrying out the method for purification.

In another aspect, the present invention discloses isoforms of Emicizumab (Protected Disulfide Isoforms) having the same heavy chain and light chain amino acid sequences with those of Emicizumab but having a molecular structure with smaller Rg (nm) value and/or Dmax (nm) value than Emicizumab. Such isoforms have a molecular structure with shorter distance between the J-chain/Q-chain N termini than Emicizumab, and specifically have an average Rg value measured with the SAXS device that is smaller by 3% or more, preferably 4% or more, more preferably 5% or more, or still more preferably 6% or more, relative to Emicizumab, and/or have an average Dmax value measured with the SAXS device that is smaller by 5% or more, preferably 6% or more, more preferably 7% or more, or still more preferably 7.5% or more, relative to Emicizumab. The isoforms may have an average Rg value that is smaller by 0.15 nm or more, preferably 0.2 nm or more, more preferably 0.25 nm or more, or still more preferably 0.3 nm or more, relative to Emicizumab, and/or have an average Dmax value that is smaller by 0.5 nm or more, preferably 1.0 nm or more, more preferably 1.2 nm or more, or still more preferably 1.4 nm or more, relative to Emicizumab. These isoforms may have an average Rg value of 4.9 nm or less, or preferably 4.8 nm or less, and/or have an average Dmax value of 17.0 nm or less, or preferably 16.5 nm or less.

The Rg and Dmax values can be measured under the conditions identified below:

(1) Antibody concentration: an antibody concentration of 7.54 mg/mL;
(2) Solvent conditions: 150 mmol/L arginine, 20 mmol/L histidine-aspartic acid, pH6.0; and
(3) Temperature: 25° C.

Here, an average Rg value can be obtained by calculating Rg for each measurement from Guinier plot and by taking an average over them. An average Dmax value can be obtained by calculating Dmax for each measurement from x-intercept of p(r) and by taking an average over them. For methods of analyzing Guinier plot and p(r), see Example 9 described below.

In another aspect, the present invention discloses isoforms of Emicizumab (Protected Disulfide Isoforms) having the same heavy chain and light chain amino acid sequences with those of Emicizumab but having a different molecular structure as compared with Emicizumab in the amino acid residues from position 146 according to EU numbering of the Q chain to position 174 according to EU numbering of the Q chain (the $152^{nd}$ position to the $180^{th}$ position from the N terminus side of SEQ ID NO: 10) and the amino acid residues from position 146 according to EU numbering of the J chain to position 174 according to EU numbering of the J chain (the $148^{th}$ position to the $176^{th}$ position from the N terminus side of SEQ ID NO: 11). The difference in molecular structure may be measured as a difference in deuterium exchange rate (% D) in HDX-MS measurement, and may be confirmed as a difference in deuterium exchange times for the peptides comprising the amino acid residues of these regions, as specifically shown in FIG. 9A.

In another aspect, the present invention discloses pharmaceutical compositions comprising Emicizumab and the isoform, wherein the percentage of the isoform in the total antibody molecules in the pharmaceutical composition is 2% or less.

In the above-described antibody molecules, antibody variants, antibody isoforms, pharmaceutical compositions comprising an antibody variant or isoform, methods for analyzing an antibody variant or isoform, or methods for suppressing formation of an antibody variant or isoform, the antibody is preferably a bispecific antibody and more preferably is Emicizumab (ACE910).

As used herein, aspects referred to by the expression "comprising" include those referred to by the expression "essentially consisting of", and those referred to by the expression "consisting of".

Numerical values recited herein may vary within a certain range, for example, depending on the instruments or equipment, measurement conditions, and procedure used by those skilled in the art, and so long as they are within a range that allows the objective of the invention to be accomplished, they may encompass a deviation of approximately 10%, for example.

All patents and references explicitly cited herein are incorporated by reference into this specification in its entirety.

The present invention will be further illustrated by the Examples below, but it is not to be construed as being limited thereto.

EXAMPLES

[Example 1] Preparation of a Genetically-Engineered Humanized Bispecific Monoclonal Antibody (Antibody Emicizumab)

For structural analysis of Emicizumab isomers (antibody variants and isoforms), antibody Emicizumab was produced in a large amount by the method described below. CHO cells into which a gene encoding Emicizumab was introduced were cultured as Emicizumab producing cells in a commercially available basal medium (basal medium for culturing animal cells). Culture was conducted under conditions giving environment generally suitable for culturing CHO cells.

Expressed antibody was purified by combination of standard column chromatography, such as affinity chromatography, ion-exchange chromatography, hydrophobic chromatography, etc.

[Example 2] Separation of Q-CDR-Clipped Variants and Protected Disulfide Isoforms (Cation Exchange High Performance Liquid Chromatography)

Figure 1B:
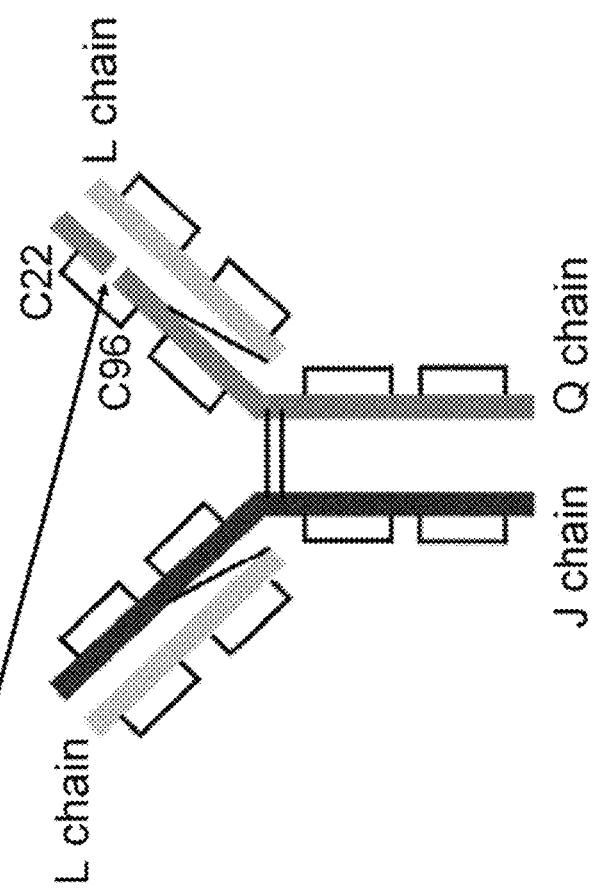
FIG. 1B is a diagram showing the molecular structure of Q-CDR-Clipped Variants. The number and the alphabet letter just under it in the diagram indicate the position of an amino acid residue counted from the N-terminus of the Emicizumab Q chain and an amino acid residue (one-letter code) at that position, respectively.
Figure 2A:
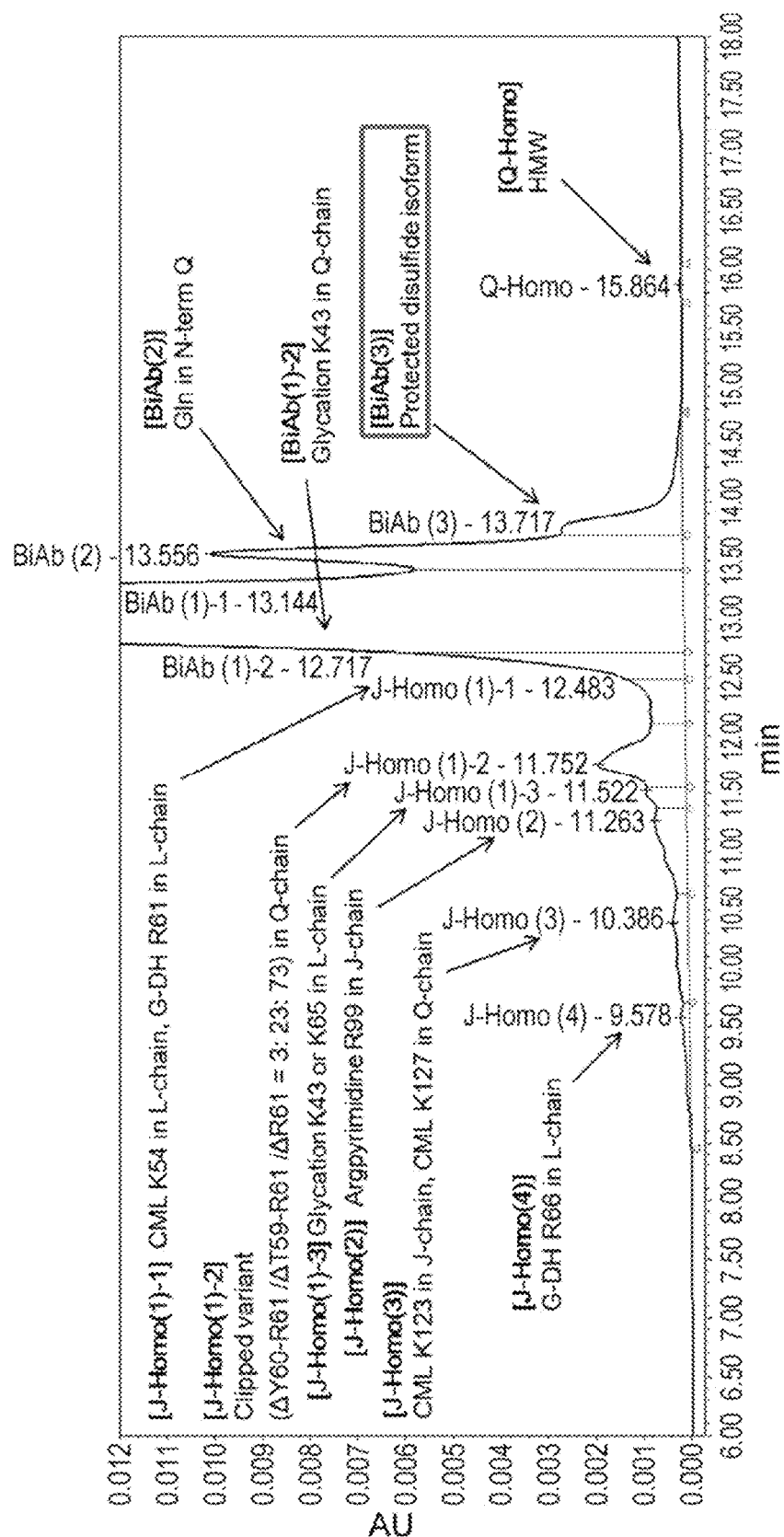
FIG. 2A shows the results of separation of Emicizumab drug substance by CE-HPLC. The peak marked with a thick-bordered box indicates Protected Disulfide Isoforms.
Figures 2B, 2C:
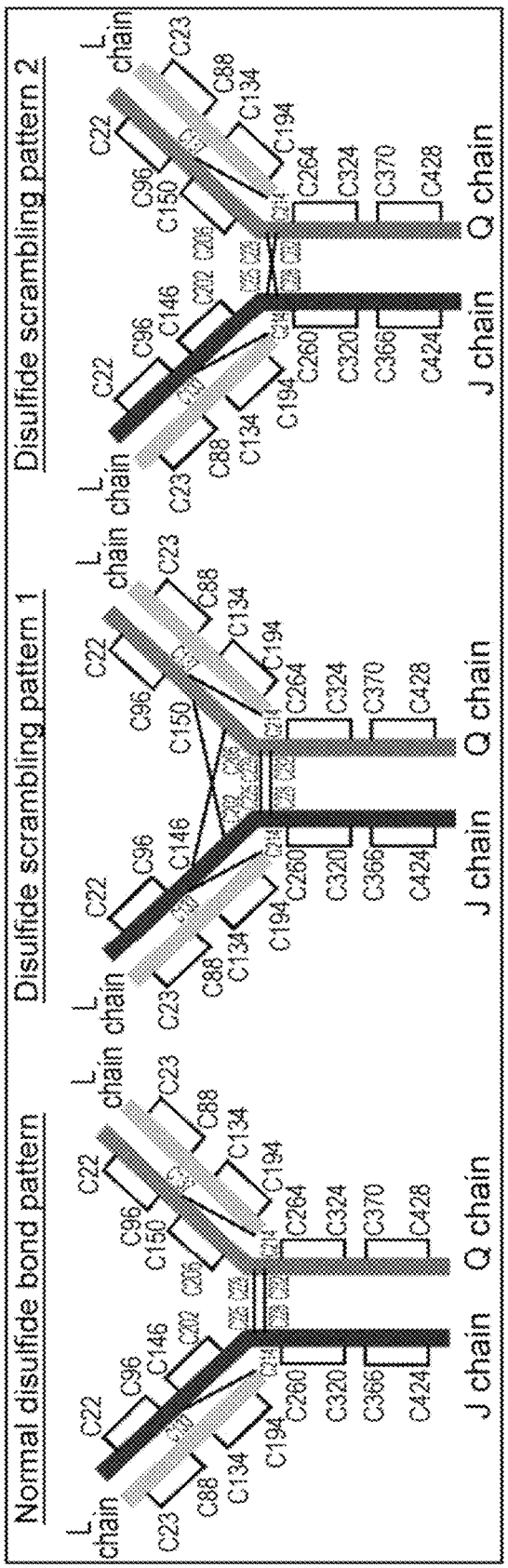
FIG. 2B is a diagram showing the molecular structure of Protected Disulfide Isoforms. The number and the alphabet letter C on the left of it in the diagram indicate the position of an amino acid residue counted from the N-terminus of the Emicizumab Q chain and a cysteine residue at that position, respectively.
FIG. 2C shows the content rate of Protected Disulfide Isoforms in the Emicizumab drug substance. The content rates under various conditions (culture conditions for antibody-producing cells) are shown by the mean values (Mean) and their standard deviation (Std Dev) for the percentage of area (area %) of the peak of Protected Disulfide Isoforms in the CE-HPLC separation results, represented in FIG. 2A.

The sample solution, prepared by diluting a specimen to analyze with mobile phase solution A (composition thereof is described below), was poured into a cation exchange column (ProPac WCX-10: particle diameter, 10 μm; inner diameter, 4.0 mm, length, 250 mm). Then, separation was carried out by liquid chromatography (column temperature: 30+/−5° C., measurement wavelength: 280 nm, flow rate: 1.0 mL/min) using an acidic mobile phase (mobile phase solution A containing 9.6 mmol/L Tris, 6.0 mmol/L piperazine, 11.0 mmol/L imidazole buffer (pH 6.0)) and an alkaline mobile phase (mobile phase solution B containing 9.6 mmol/L Tris, 6.0 mmol/L piperazine, 11.0 mmol/L imidazole, and 150 mmol/L sodium chloride (pH 9.9)). As a result, it was confirmed that Q-CDR-Clipped Variants and Protected Disulfide Isoforms were separated in more acidic and alkaline regions, respectively, as compared with the main peak corresponding to Emicizumab (FIG. 1A and FIG. 2A).

[Example 3] Separation of Protected Disulfide Isoforms (IdeS Digestion, Partial Reduction, Reverse Phase High Performance Liquid Chromatography)

Specimens were diluted using phosphate buffer, digested with IdeS protease and PNGase-F, and then partially reduced with DTT in Tris buffer solution containing no denaturant. The sample diluted using TFA solution was poured into the reverse phase high performance liquid chromatography column and separated. As a result, it was found that the main component of Emicizumab is separated on a chromatograph in the state where the disulfide bonds between the heavy and light chains are reduced, whereas Protected Disulfide Isoforms are detected with unique peaks representing the state where the disulfide bonds between the heavy chains remain not reduced (FIG. 3B and FIG. 3D).

[Example 4] Separation of Protected Disulfide Isoforms (IdeS Digestion, Denaturation, Reverse Phase High Performance Liquid Chromatography)

Specimens were diluted with a buffer, digested with IdeS protease and PNGase-F, and then proteins were denatured using a denaturation buffer. After that, the sample diluted using TFA solution was poured into the reverse phase high-performance liquid chromatography column and separated. As a result, it was found that the F(ab')2 portion of Protected Disulfide Isoforms is separated after a longer retention time than the main component of Emicizumab (FIG. 4C and FIG. 4D).

[Example 5] Separation of Protected Disulfide Isoforms (IdeS Digestion, Reverse Phase High Performance Liquid Chromatography)

Specimens were diluted using a buffer, and digested with IdeS protease and PNGase-F. The sample diluted using TFA solution was separated by reverse phase high performance liquid chromatography. As a result, it was found that the F(ab')2 portion of Protected Disulfide Isoforms is separated after a longer retention time than the main component of Emicizumab (FIG. 4A and FIG. 4B).

[Example 6] Evaluation of Biological Activity of Q-CDR-Clipped Variants and Protected Disulfide Isoforms Chromogenic Assay The amount of activated blood coagulation factor X (FXa), produced through reaction of Emicizumab in the presence of FIXa and FX in a reaction field where phospholipid was supplied, was quantitatively measured using a specific chromogenic substrate. Specifically, Emicizumab solutions diluted at various concentrations were prepared by adding a solution (TBSB) containing Tris-hydroxymethyl aminomethane, sodium chloride, and BSA to a sample. Each diluted solution was added to its respective well in a 96-well microplate, a coagulation factor solution containing FIXa, FX, calcium chloride, magnesium chloride, phospholipid, and TBSB was added thereto, and, after shaking, the plate was left for 30 minutes. Ethylene diamine tetraacetic acid solution was added to each well, the plate was shaken, and a chromogenic substrate solution was added to each well (N-benzoyl-L-isoleucyl-L-glutamyl-glycyl-L-arginine-p-nitroaniline hydrochloride and its methyl ester). After shaking, the plate was left for 35 minutes. After one to two minutes of shaking, absorbance (Abs) at 405 nm was measured for each well using a plate reader. Based on the absorbance values obtained from standard solutions and sample solutions at various concentrations, specific activity of the samples relative to the standard solutions were determined from a regression curve generated using 4-parameter-parallel-lines-logistics analysis program. As a result, Q-CDR-Clipped Variants exhibited 18+/−1%, Protected Disulfide Isoforms exhibited 8+/−0% of biological activity relative to the Emicizumab standard solution.

Clotting Assay

In this assay, the time until clotting due to fibrin formation was measured based on changes in turbidity as indicator, in a system reconstituting endogenous coagulation activation mechanism using factor VIII deficient human plasma. Specifically, a solution containing Tris-hydroxymethyl aminomethane, sodium chloride, and BSA was added to the sample to prepare Emicizumab solutions diluted at various concentrations. Using an automatic blood coagulation measuring device, the diluted solutions were added with factor VIII deficient plasma and incubated, then were added with APTT reagent and incubated, and lastly were added with calcium chloride solution and measured to determine the clotting time. The specific activity of the samples relative to the standard substance was calculated by parallel line assay. As a result, Q-CDR-Clipped Variants exhibited 18+/−1%, Protected Disulfide Isoforms exhibited 16+/−1% of biological activity relative to the Emicizumab standard solution.

[Example 7] Assessment of Effect of Culture Parameters on the Ratio of Q-CDR-Clipped Variants Initial Culture Medium Plant-derived hydrolyzates, amino acids, and such were added and dissolved into commercially available basal medium. The mixture was then sterilized by filtration.

Feed Medium

Glucose, amino acids, and such were added and dissolved into commercially available basal medium. The mixture was then sterilized by filtration.

Cells

Emicizumab producing CHO cells (DXB-11 strain) comprising a gene encoding Emicizumab incorporated therein were used.

Culture Method

Production medium (+/−10% to the standard concentration) was poured into a 1 L-scale cell culture device and the above-described CHO cell strain was seeded thereto to give 2 to 6×$10^5$ cells/mL. Cell culture was started at the temperature of 36 to 38° C., dissolved oxygen concentration of 40%, initial pH of 7.20. Starting from day 1 to 3 of culture, feed medium (+/−10% to the standard concentration) was added at a constant flow rate, and on day 3 of culture, pH was shifted to 6.70-7.10. Culture was continued for 13 to 15 days.

Culture was conducted under a total of 56 conditions, according to the experimental plan designed based on a central composite design including 12 central points (6 factors: concentration of the production medium, concentration of the feed medium, initial cell density, temperature, time to start adding the feed medium, pH after shifting). For all conditions, culture medium was sampled on day 13, 14, and 15 of culture (a total of 168 samples) and centrifuged (at 3000 rpm for 5 minutes). Supernatant was Protein-A purified, and then was used for measuring the ratio of Q-CDR-Clipped Variants.

Analytical Method

Viable cell number and viable cell ratio were measured by trypan blue staining. Q-CDR-Clipped Variants were detected as a peak by cation exchange high-performance liquid chromatography using a cation column (ProPac WCX-10).

Results

Figure 5:
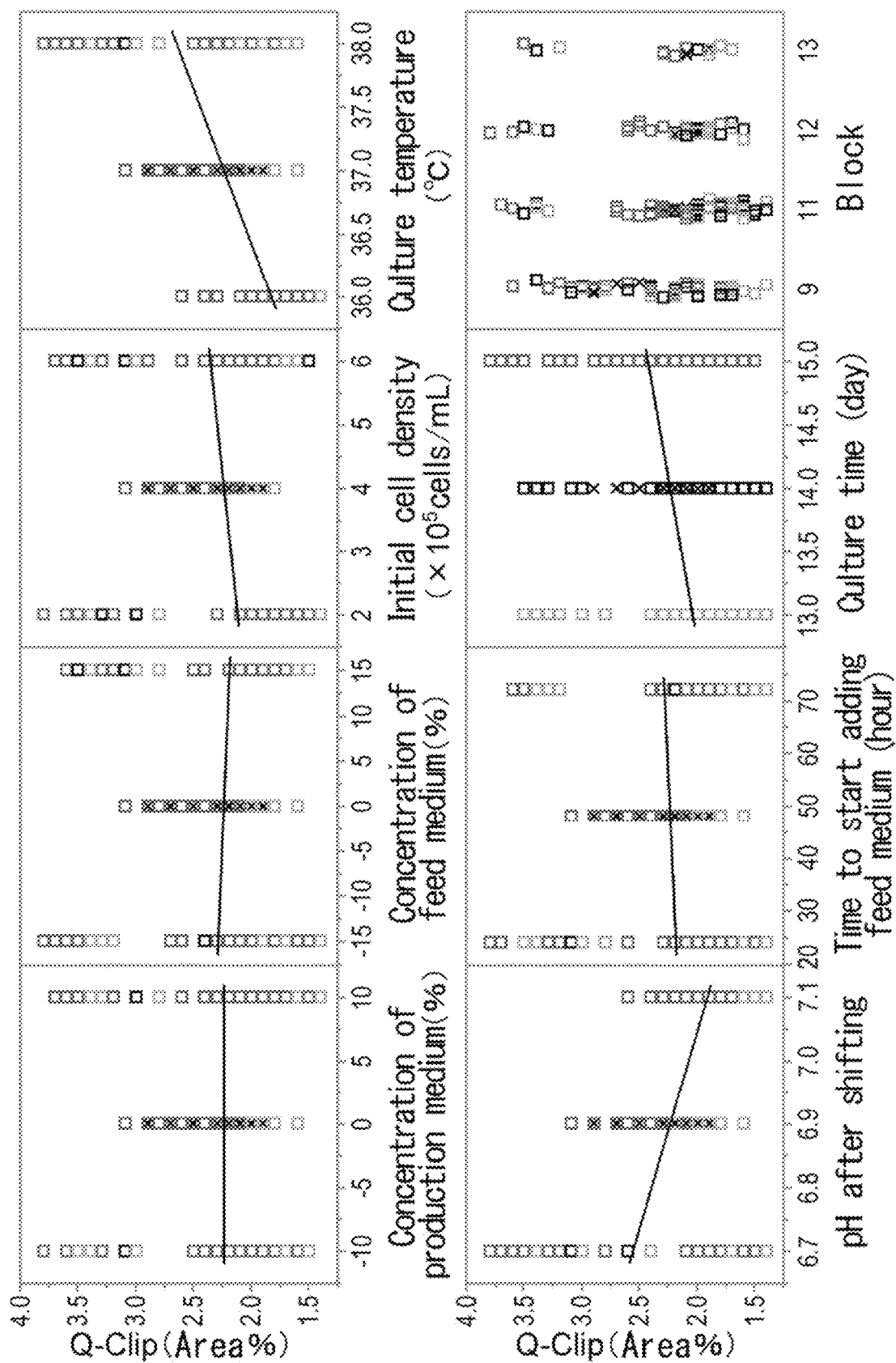
FIG. 5 shows the content rate of Q-CDR-Clipped Variants in culture supernatant of Emicizumab-producing CHO cells cultured under various culture conditions. Samples of culture supernatant purified using Protein A was used to measure the content rate of Q-CDR-Clipped Variants. The vertical axis indicates Q-CDR-Clipped Variant content rate (peak area %) and the horizontal axis indicates various culture conditions.
Figure 6:
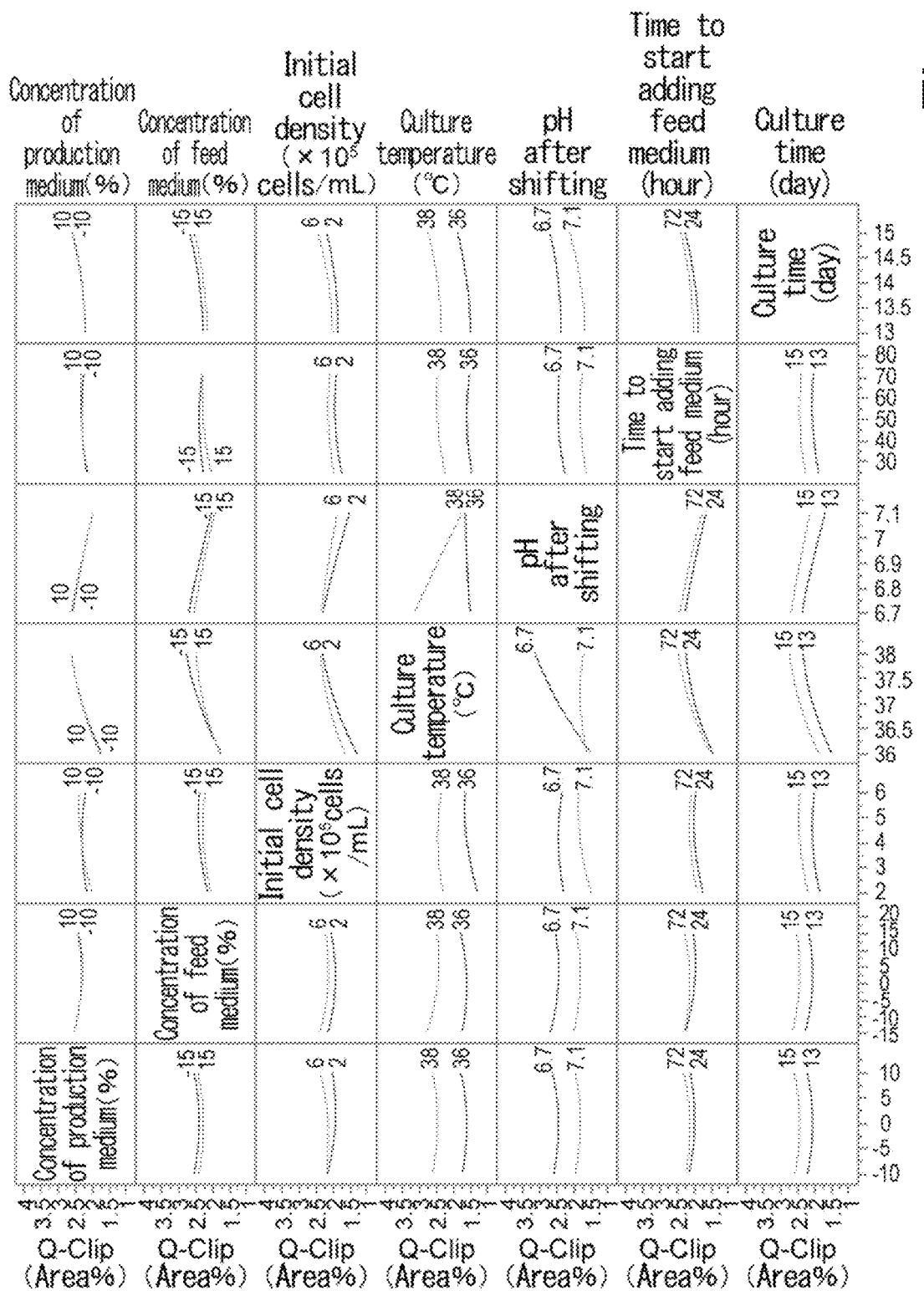
FIG. 6 shows the content rate of Q-CDR-Clipped Variants in culture supernatant of Emicizumab-producing CHO cells cultured under various culture conditions. Samples of culture supernatant purified using Protein A was used to measure the content rate of Q-CDR-Clipped Variants. The vertical axis indicates Q-CDR-Clipped Variant content rate (peak area %) and the horizontal axis indicates various culture conditions.

Results are shown in FIG. 5 and FIG. 6. The ratio of Q-CDR-Clipped Variants was affected by both temperature and pH after shifting. Within the range tested (temperature of from 36 to 38° C. and pH after shifting from 6.70 to 7.10), the ratio of Q-CDR-Clipped Variants was reduced more in culturing at 36° C. and culturing at shifted pH of 7.10. There was an interaction between temperature and pH after shifting (shifted pH). It was found that the ratio of Q-CDR-Clipped Variants can be reduced even under the culturing condition at 38° C., when the shifted pH was lowered to 6.70.

Q-CDR-Clipped Variants were successfully controlled to 4% or less, by controlling culture temperature to 36-38° C. and pH on or after day 3 of culture to 6.70-7.10.

[Example 8] Removal of Q-CDR-Clipped Variants by Cation Exchange Chromatography

Utilizing the difference in electrostatic property of Q-CDR-Clipped Variants and antibody Emicizumab, a method for separating these was established. An example is described below.

Figure 7:
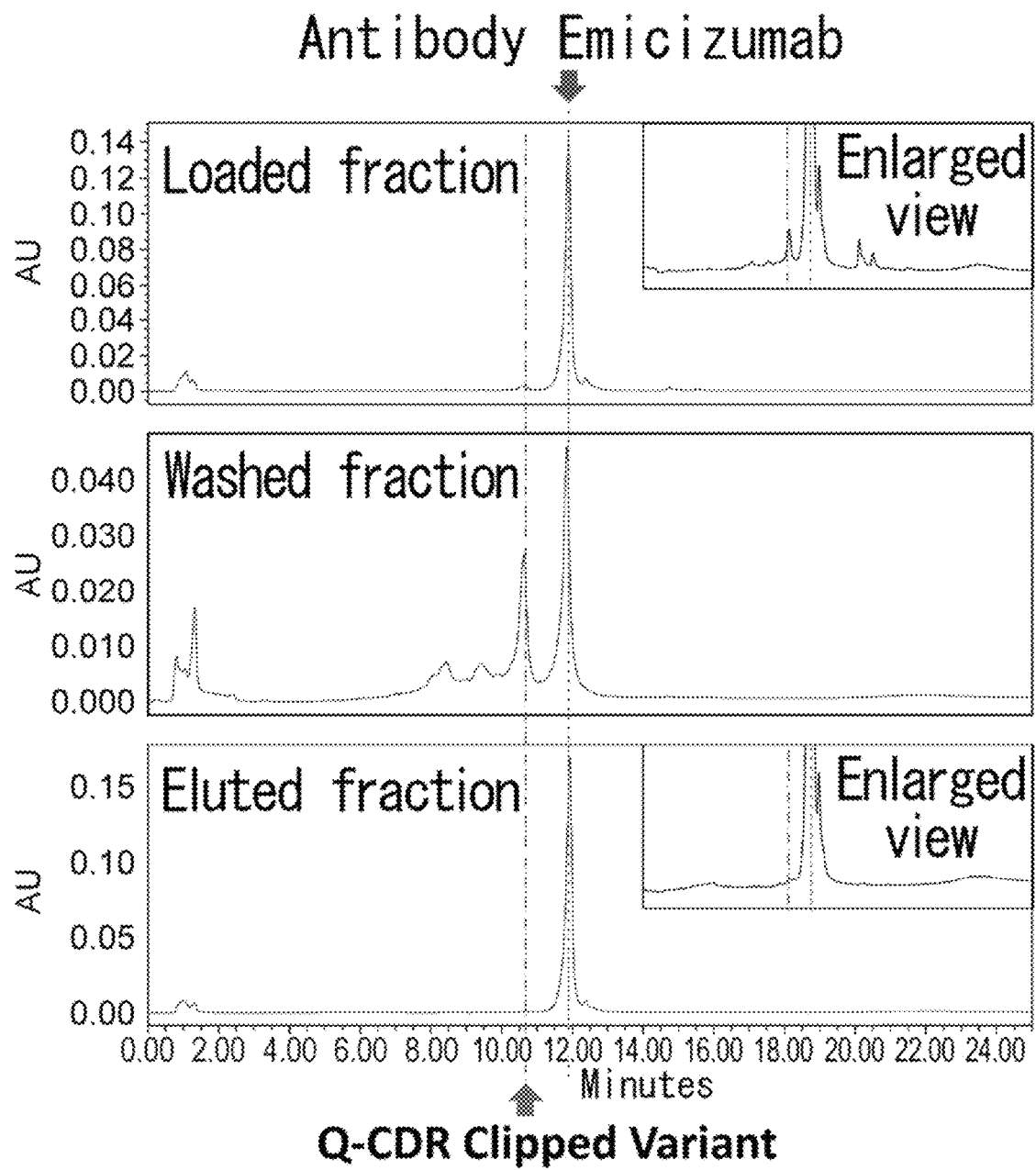
FIG. 7 shows the results of CE-HPLC analysis on each fraction of a solution of antibody Emicizumab containing Q-CDR-Clipped Variants, the fraction being obtained during purification including the steps in the Bind & Elute mode of cation exchange chromatography (CEX). "Loaded fraction" shows the results of the CE-HPLC analysis on the antibody solution loaded onto the cation exchange column. "Washed fraction" shows the results of the CE-HPLC analysis on the column-adsorbed fraction obtained after passing a pH 7.2 phosphate buffer containing 25 mmol/L sodium chloride (washed). "Eluted fraction" shows the results of the CE-HPLC analysis on the column-adsorbed fraction obtained after passing a pH 6.5 phosphate buffer containing 100 mmol/L sodium chloride. Compared with the loaded fraction and the washed fraction, the peak of Q-CDR-Clipped Variant on the more acidic side than the peak of antibody Emicizumab was found disappeared in the eluted fraction.

A column was filled with Capto SP ImpRes (GE) or a permissible substitute therefor as a cation exchange resin and equilibrated. The column was loaded with a solution of antibody Emicizumab containing Q-CDR-Clipped Variants to let them both absorbed. After loading, the column was washed with a phosphate buffer solution containing sodium chloride, and then, only the variants on acidic side including Q-CDR-Clipped Variants were specifically eluted so that they were separated and removed from antibody Emicizumab. In order to show how well the removal went, the washed fraction, the eluted fraction, and the loaded fraction before separation were CE-HPLC analyzed (FIG. 7).

The conditions of the loading, washing, and eluting were as shown below.

Loading: a Tris-hydrochloric acid buffer solution containing antibody Emicizumab adjusted at pH 5.0 was loaded on the condition of 33 g of antibody Emicizumab per 1 L of resin.
Washing: a phosphate buffer solution containing 25 mmol/L sodium chloride adjusted at pH 7.2 was passed through the 3.5 CV column at room temperature.
Eluting: a phosphate buffer solution containing 100 mmol/L sodium chloride adjusted at pH 6.5 was passed through the 6.5 CV column at room temperature.

[Example 9] Analysis on Molecular Structure of the Protected Disulfide Isoforms

Antibody preparations for Emicizumab and a Protected Disulfide Isoform were prepared (antibody at a concentration of 7.54 mg/mL, 150 mmol/L arginine, 20 mmol/L histidine-aspartic acid, pH 6.0). SAXS measurement was carried out using line-collimated X-ray beam (Cu Kα, λ=0.1542 nm) generated with the SAXSess mc2 system (Anton Paar, Graz, Austria). Temperature for measurement was set at 25° C. Two-dimensional imaging plates were used for the detection. Exposure time for the X-ray beam was set to 30 minutes. The two-dimensional scattered intensity was transformed to a single-dimensional scattered intensity $I(q)$, on the SAXSQuant software (Anton Paar). Here, q is a scattering vector and is defined as $q=(4\pi/\lambda)\sin(\theta/2)$ ($\theta$ is a scattering angle). Scattering curves were normalized against scattered intensity at $q=0$ for the beam transmitted through the beam stopper, and then were processed for blank correction (with buffer and capillary) and optical system (desmearing) correction. Guinier plotting was carried out on the corrected scattering curves under the conditions satisfying $q \times Rg < 1.3$, to obtain radius of gyration, Rg (nm); however, when there was a drop of scattered intensity in a small angle side, data for the range of q corresponding thereto was excluded in carrying out Guinier plotting, so as to avoid effects by interparticle repulsion. In a system assuming that there was no interparticle interaction (structure factor $S(q)=1$), scattered intensity $I(q)$ is given as a Fourier transform of pair distance distribution function $p(r)$. By applying the indirect Fourier transform method (NPL 9) to the corrected scattering curves, $p(r)$ for the particles were obtained. The maximum dimension Dmax (nm) was obtained from the x-intercept of $p(r)$. The measurement was carried out three times for each of Emicizumab antibody preparation (Main) and the Protected Disulfide Isoform antibody preparation (BiAb3).

As a result, the Protected Disulfide Isoform had the average Rg value of 4.8 nm or less (the value 0.3 nm or more smaller than that of Emicizumab) and the average Dmax value of 16.5 nm or less (the value 1.4 nm or more smaller than that of Emicizumab), and exhibited 6% or more smaller average Rg value and 7.5% or more smaller average Dmax value as compared to Emcizumab. It is reported that the Dmax values of IgG4 antibody molecules, the same subclass of antibodies as Emicizumab, correspond to the distance between the tips of the two Fab domains (NPL 10); therefore, it is considered that the distance between the tips of the two Fab domains of the Protected Disulfide Isoform was shortened, thereby giving smaller values of Rg, which represents a distance from the center of mass of a molecule. Based on the above, it was confirmed that the Protected Disulfide Isoform takes the molecular structure having a shorter distance between the N termini of the J-chain/Q-chain than Emicizumab (FIGS. 8A to D). For bispecific antibodies for mediating interaction between two types of antigens, the distance between the Fab domains should be of crucial importance in determining inter-antigen interactions in view of the three-dimensional structure. Therefore, how to control the percentage of such isoforms in a pharmaceutical composition is an important task, not only for Emicizumab but, generally for antibody pharmaceuticals comprising a bispecific antibody.

[Example 10] Molecular Structure Analysis by HDX-MS (Hydrogen-Deuterium eXchange Mass Spectrometry)

Antibody preparations for Emicizumab and for each of the Protected Disulfide Isoforms were prepared (antibody at a concentration of 1 mg/mL, 150 mmol/L arginine, 20 mmol/L histidine-aspartic acid, pH 6.0) and HDX-MS measurement (measurements at deuterium exchange times 30 s, 60 s, 120 s, 240 s, 480 s, 960 s, 1920 s, and 3840 s) was carried out using the HDX-MS device (Orbitrap Fusion Lumos (Thermo Fisher Scientific), UltiMate30000RSLCnano (Thermo Fisher Scientific) with HDX-PAL (LEAP Technologies)).

Figure 9A:
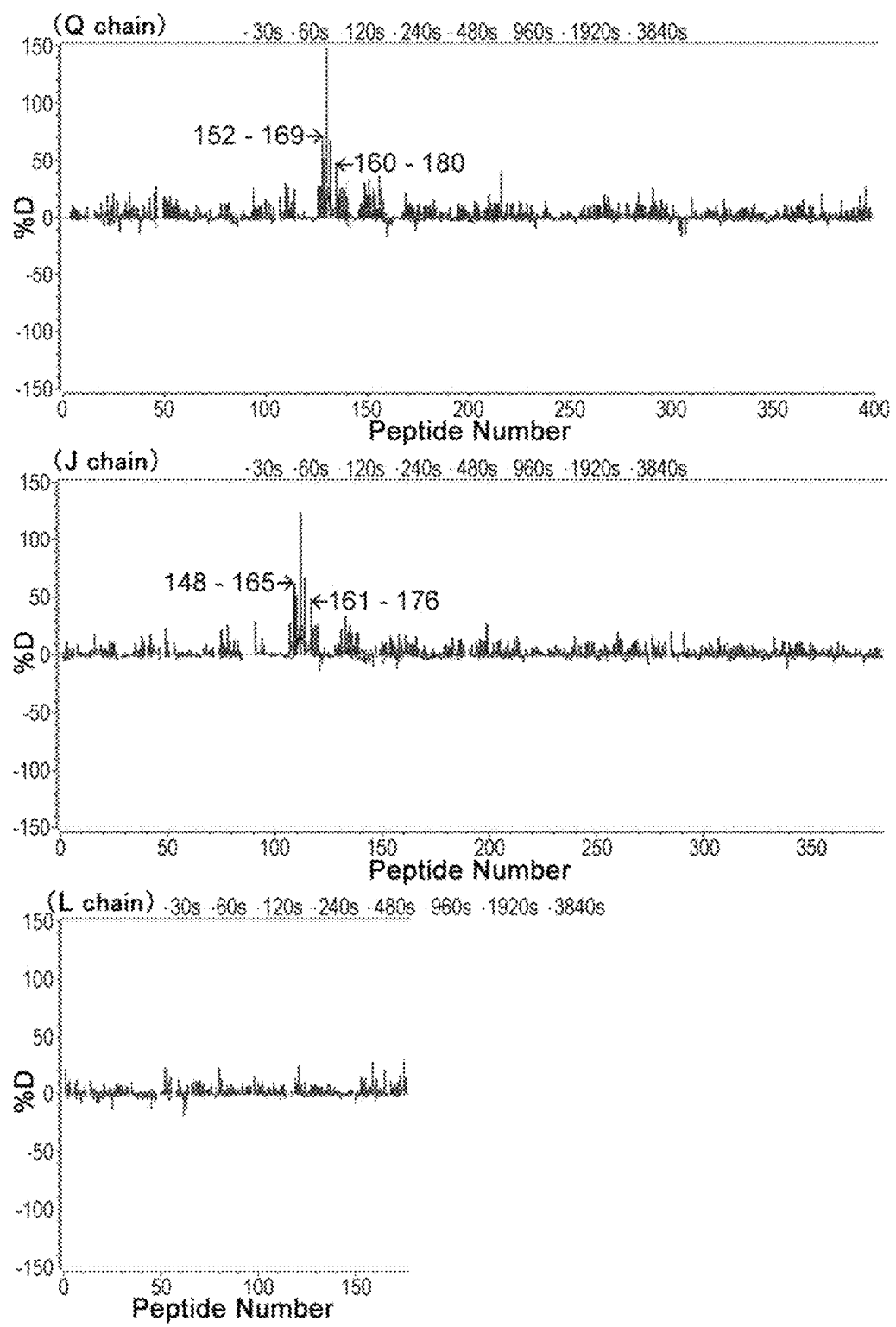
FIG. 9A shows residual plot of Emicizumab (main component in cation exchange high performance liquid chromatography) and the Protected Disulfide Isoforms on deuterium exchange rate (% D) in the HDX-MS measurement (deuterium exchange times 30 s, 60 s, 120 s, 240 s, 480 s, 960 s, 1920 s, and 3840 s). Each bar in the graph indicates the sum of the differences in the results from each deuterium exchange time for the Q chain, J chain, and L chain.
Figure 9B:
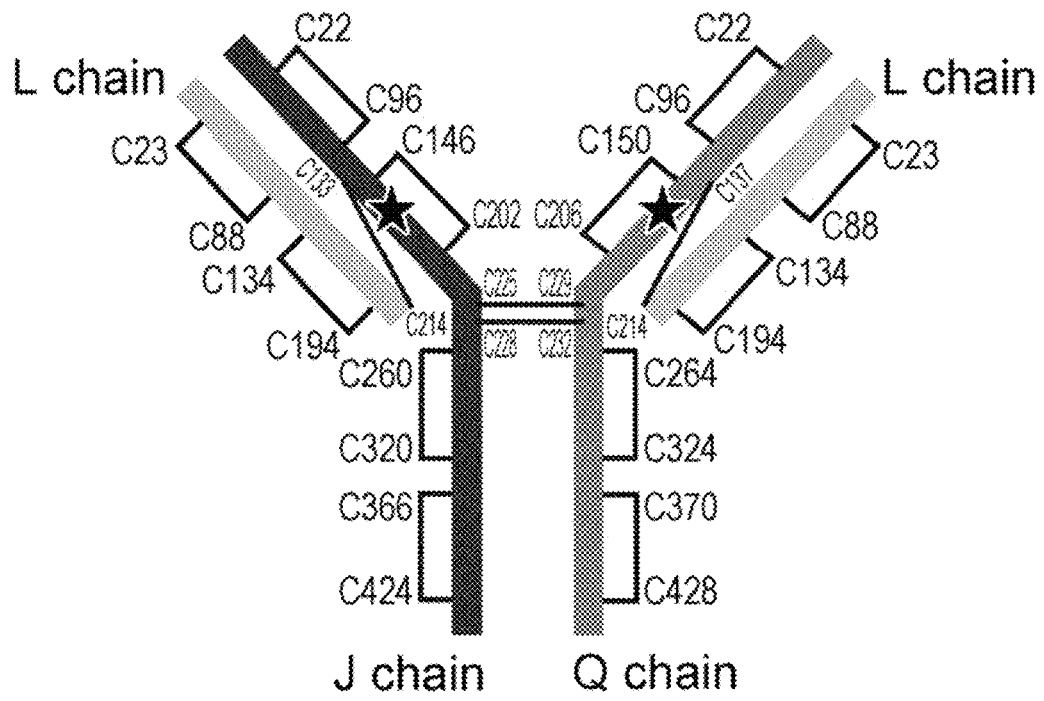
FIG. 9B shows the parts for which difference in molecular structure in the Protected Disulfide Isoforms from Emicizumab was suggested by the HDX-MS measurement. Difference in molecular structure in the Protected Disulfide Isoforms from Emicizumab was notable in the peptide comprising the amino acid residues from position 146 according to EU numbering of the Q chain to position 174 according to EU numbering of the Q chain (the $152^{nd}$ position to the $180^{th}$ position from the N terminus side of SEQ ID NO: 10) and the peptide comprising the amino acid residues from position 146 according to EU numbering of the J chain to position 174 according to EU numbering of the J chain (the $148^{th}$ position to the $176^{th}$ position from the N terminus side of SEQ ID NO: 11). See the parts indicated with stars.

As a result, prominent difference in deuterium exchange rate (% D) in the HDX-MS measurement was observed in the peptide comprising the amino acid residues from position 146 according to EU numbering of the Q chain to position 174 according to EU numbering of the Q chain (the $152^{nd}$ position to the $180^{th}$ position from the N terminus side of SEQ ID NO: 10) and the peptide comprising the amino acid residues from position 146 according to EU numbering of the J chain to position 174 according to EU numbering of the J chain (the $148^{th}$ position to the $176^{th}$ position from the N terminus side of SEQ ID NO: 11). On the basis of this result, it was confirmed that the Protected Disulfide Isoforms have a different structure in these regions as compared with Emicizumab (FIG. 9A and FIG. 9B).

INDUSTRIAL APPLICABILITY

The antibody variants and isoforms of the present invention have extremely reduced FVIII mimetic activity as compared with Emicizumab; therefore, the pharmaceutical compositions of the present invention comprising Emicizumab and having lowered content ratio for such antibody variants and isoforms are useful as a means for treating hemophilia. The methods for analyzing the antibody variants and isoforms of the present invention are useful for evaluating quality of Emicizumab preparations, and also are useful in development of Emicizumab preparations with a lowered content ratio for the antibody variants and isoforms or in development of methods for suppressing formation of the antibody variants and isoforms.

---

The invention claimed is:

1. A purified variant of Emicizumab, wherein the variant is identical to Emicizumab except for modifications consisting of, in a heavy chain variable region that corresponds to SEQ ID NO: 13:
   (1) the heavy chain variable region has a deletion of either (a) or (b):
      (a) Arg at position 61; or
      (b) Tyr-Tyr-Arg at positions 59-61,
   and
   (2) the heavy chain variable region is split into two fragments:
      (i) an N-terminal fragment with a C-terminus that is either Tyr at position 60 or Thr at position 58, and
      (ii) a C-terminal fragment with an N-terminus that is Arg at position 62,
   wherein the two fragments are linked by a disulfide bond, and wherein all position numbers are based on numbering in SEQ ID NO: 13.

2. A method for determining whether a variant of Emicizumab is present in a sample containing Emicizumab, the method comprising:
   using a purified variant of Emicizumab as a reference standard for a chromatography column by subjecting the purified variant to a chromatography process on the chromatography column, thereby identifying the position where a peak corresponding to the variant elutes from the chromatography column,
      wherein the variant is identical to Emicizumab except for modifications consisting of, in a heavy chain variable region that corresponds to SEQ ID NO: 13:
         (1) the heavy chain variable region has a deletion of either (a) or (b):
            (a) Arg at position 61; or
            (b) Tyr-Tyr-Arg at positions 59-61,
         and
         (2) the heavy chain variable region is split into two fragments, linked by a disulfide bond:
            (i) an N-terminal fragment with a C-terminus that is either Tyr at position 60 or Thr at position 58, and
            (ii) a C-terminal fragment with an N-terminus that is Arg at position 62,
         wherein all position numbers are based on numbering in SEQ ID NO: 13, and
      wherein the chromatography process comprises ion exchange chromatography or separation based on charge; and
   subjecting the sample to the chromatography process on the chromatography column, to determine whether a peak at the position identified as corresponding to the variant appears, as an indication that a variant identical to the purified variant is present in the sample.

3. A method for purifying Emicizumab from a sample containing Emicizumab and an antibody variant, wherein the variant is identical to Emicizumab except for modifications consisting of, in a heavy chain variable region that corresponds to SEQ ID NO: 13:
   (1) heavy chain variable region has a deletion of either (a) or (b):
      (a) Arg at position 61, or
      (b) Tyr-Tyr-Arg at positions 59-61;
   and
   (2) the heavy chain variable region is split into two fragments:
      (i) an N-terminal fragment with a C-terminus that is either Tyr at position 60 or Thr at position 58, and
      (ii) a C-terminal fragment with an N-terminus that is Arg at position 62,
   wherein the two fragments are linked by a disulfide bond, and wherein all position numbers are based on numbering in SEQ ID NO: 13,
   the method comprising:
      (A) applying a purified preparation of the antibody variant to an ion exchange chromatographic column as a reference standard to identify the position where the antibody variant elutes from the column compared to the position where Emicizumab elutes from the column;
      (B) subjecting the sample to chromatography on the column to separate a fraction or fractions corresponding to the position where Emicizumab elutes from the column from a fraction or fractions corresponding to the position where the antibody variant elutes from the column; and
      (C) collecting a fraction or fractions containing Emicizumab from the column, wherein the collected fraction or fractions contain a higher ratio of Emicizumab to the antibody variant than did the sample prior to (B).

4. The method of claim 3, wherein the column utilizes cation exchange chromatography.

5. The method of claim 2, further comprising conducting quantitative analysis to analyze the ratio of the variant to total antibody molecules in the sample.

6. The method of claim 2, wherein the chromatography process comprises ion exchange chromatography.

7. The method of claim 2, wherein the chromatography process comprises separation based on charge.

* * * * *

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: Heavy chain variable region CDR1

<400> SEQUENCE: 1

Tyr Tyr Asp Ile Gln
1               5

<210> SEQ ID NO 2
<211> LENGTH: 17
<212> TYPE: PRT
<213> ORGANISM: Artificial Sequence
<220> FEATURE:
<223> OTHER INFORMATION: Heavy chain variable region CDR2

<400> SEQUENCE: 2

Ser Ile Ser Pro Ser Gly Gln Ser Thr Tyr Tyr Arg Arg Glu Val Lys
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: Heavy chain variable region CDR3

<400> SEQUENCE: 3

Arg Thr Gly Arg Glu Tyr Gly Gly Gly Trp Tyr Phe Asp Tyr
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Heavy chain variable region CDR1

<400> SEQUENCE: 4
```

```
Asp Asn Asn Met Asp
1               5

<210> SEQ ID NO 5
<211> LENGTH: 17
<212> TYPE: PRT
<213> ORGANISM: Artificial Sequence
<220> FEATURE:
<223> OTHER INFORMATION: Heavy chain variable region CDR2

<400> SEQUENCE: 5

Asp Ile Asn Thr Arg Ser Gly Gly Ser Ile Tyr Asn Glu Glu Phe Gln
1               5                   10                  15

Asp

<210> SEQ ID NO 6
<211> LENGTH: 10
<212> TYPE: PRT
<213> ORGANISM: Artificial Sequence
<220> FEATURE:
<223> OTHER INFORMATION: Heavy chain variable region CDR3

<400> SEQUENCE: 6

Arg Lys Ser Tyr Gly Tyr Tyr Leu Asp Glu
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Light chain variable region CDR1

<400> SEQUENCE: 7

Lys Ala Ser Arg Asn Ile Glu Arg Gln Leu Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Light chain variable region CDR2

<400> SEQUENCE: 8

Gln Ala Ser Arg Lys Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Light chain variable region CDR3

<400> SEQUENCE: 9

Gln Gln Tyr Ser Asp Pro Pro Leu Thr
1               5

<210> SEQ ID NO 10
<211> LENGTH: 448
<212> TYPE: PRT
<213> ORGANISM: Artificial Sequence
<220> FEATURE:
<223> OTHER INFORMATION: Heavy chain

<400> SEQUENCE: 10
```

```
Gln Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Ser Tyr Tyr
             20                  25                  30
Asp Ile Gln Trp Val Arg Gln Ala Pro Gly Lys Gly Leu Glu Trp Val
         35                  40                  45
Ser Ser Ile Ser Pro Ser Gly Gln Ser Thr Tyr Tyr Arg Arg Glu Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Arg Thr Gly Arg Glu Tyr Gly Gly Trp Tyr Phe Asp Tyr
             100                 105                 110
Trp Gly Gln Gly Thr Leu Val Thr Val Ser Ser Ala Ser Thr Lys Gly
         115                 120                 125
Pro Ser Val Phe Pro Leu Ala Pro Cys Ser Arg Ser Thr Ser Glu Ser
         130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                 165                 170                 175
Pro Ala Val Leu Gln Ser Ser Gly Leu Tyr Ser Leu Ser Ser Val Val
             180                 185                 190
Thr Val Pro Ser Ser Ser Leu Gly Thr Gln Thr Tyr Thr Cys Asn Val
             195                 200                 205
Asp His Lys Pro Ser Asn Thr Lys Val Asp Lys Arg Val Glu Ser Lys
         210                 215                 220
Tyr Gly Pro Pro Cys Pro Pro Cys Pro Ala Pro Glu Phe Leu Gly Gly
225                 230                 235                 240
Pro Ser Val Phe Leu Phe Pro Pro Lys Pro Lys Asp Thr Leu Met Ile
                 245                 250                 255
Ser Arg Thr Pro Glu Val Thr Cys Val Val Asp Val Ser Gln Glu
             260                 265                 270
Asp Pro Glu Val Gln Phe Asn Trp Tyr Val Asp Gly Val Glu Val His
         275                 280                 285
Asn Ala Lys Thr Lys Pro Arg Glu Glu Gln Tyr Asn Ser Thr Tyr Arg
 290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                 325                 330                 335
Lys Thr Ile Ser Lys Ala Lys Gly Gln Pro Arg Glu Pro Gln Val Tyr
             340                 345                 350
Thr Leu Pro Pro Ser Gln Lys Glu Met Thr Lys Asn Gln Val Ser Leu
             355                 360                 365
Thr Cys Leu Val Lys Gly Phe Tyr Pro Ser Asp Ile Ala Val Glu Trp
 370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                 405                 410                 415
```

```
Lys Ser Arg Trp Gln Glu Gly Asn Val Phe Ser Cys Ser Val Met His
            420                 425                 430

Glu Ala Leu His Asn Arg Tyr Thr Gln Lys Ser Leu Ser Leu Ser Pro
        435                 440                 445

<210> SEQ ID NO 11
<211> LENGTH: 444
<212> TYPE: PRT
<213> ORGANISM: Artificial Sequence
<220> FEATURE:
<223> OTHER INFORMATION: Heavy chain

<400> SEQUENCE: 11

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335
```

```
Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Glu Ser Leu Ser Leu Ser Pro
        435                 440

<210> SEQ ID NO 12
<211> LENGTH: 214
<212> TYPE: PRT
<213> ORGANISM: Artificial Sequence
<220> FEATURE:
<223> OTHER INFORMATION: Light chain

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 123
<212> TYPE: PRT
<213> ORGANISM: Artificial Sequence
<220> FEATURE:
```

<223> OTHER INFORMATION: Heavy chain variable region

<400> SEQUENCE: 13

Gln Val Gln Leu Val Glu Ser Gly Gly Gly Leu Val Gln Pro Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Gly Trp Tyr Phe Asp Tyr
            100                 105                 110

Trp Gly Gln Gly Thr Leu Val Thr Val Ser Ser
        115                 120

<210> SEQ ID NO 14
<211> LENGTH: 119
<212> TYPE: PRT
<213> ORGANISM: Artificial Sequence
<220> FEATURE:
<223> OTHER INFORMATION: Heavy chain variable region

<400> SEQUENCE: 14

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser
        115

<210> SEQ ID NO 15
<211> LENGTH: 107
<212> TYPE: PRT
<213> ORGANISM: Artificial Sequence
<220> FEATURE:
<223> OTHER INFORMATION: Light chain variable region

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile

```
                35                    40                   45
Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys
            100             105
```